United States Patent
Lipford et al.

(10) Patent No.: US 7,410,975 B2
(45) Date of Patent: Aug. 12, 2008

(54) SMALL MOLECULE TOLL-LIKE RECEPTOR (TLR) ANTAGONISTS

(75) Inventors: Grayson B. Lipford, Watertown, MA (US); Alexandra Forsbach, Ratingen (DE); Charles Zepp, Hardwick, MA (US)

(73) Assignees: Coley Pharmaceutical Group, Inc., Wellesley, MA (US); Coley Pharmaceutical GmbH, Langenfeld (DE)

( * ) Notice: Subject to any disclaimer, the term of this patent is extended or adjusted under 35 U.S.C. 154(b) by 270 days.

(21) Appl. No.: 10/872,196

(22) Filed: Jun. 18, 2004

(65) Prior Publication Data

US 2005/0119273 A1      Jun. 2, 2005

Related U.S. Application Data

(60) Provisional application No. 60/556,007, filed on Mar. 23, 2004, provisional application No. 60/480,588, filed on Jun. 20, 2003.

(51) Int. Cl.
- A61K 31/517 (2006.01)
- C07D 239/72 (2006.01)
- C07D 239/93 (2006.01)
- C07D 239/94 (2006.01)

(52) U.S. Cl. ............ 514/266.2; 514/266.4; 544/284; 544/293

(58) Field of Classification Search .......... 514/266.2, 514/266.4; 544/284, 293
See application file for complete search history.

(56) References Cited

U.S. PATENT DOCUMENTS

| | | | |
|---|---|---|---|
| 4,766,211 A * | 8/1988 | Zink et al. ............... 544/58.6 |
| 5,436,233 A * | 7/1995 | Lee et al. .................. 514/63 |
| 5,663,153 A | 9/1997 | Hutcherson et al. |
| 5,723,335 A | 3/1998 | Hutcherson et al. |
| 5,939,421 A | 8/1999 | Palanki et al. |
| 6,194,388 B1 | 2/2001 | Krieg et al. |
| 6,207,646 B1 | 3/2001 | Krieg et al. |
| 6,214,806 B1 | 4/2001 | Krieg et al. |
| 6,218,371 B1 | 4/2001 | Krieg et al. |
| 6,221,882 B1 | 4/2001 | Macfarlane |
| 6,239,116 B1 | 5/2001 | Krieg et al. |
| 6,339,068 B1 | 1/2002 | Krieg et al. |
| 6,399,630 B1 | 6/2002 | Macfarlane |
| 6,406,705 B1 | 6/2002 | Davis et al. |
| 6,429,199 B1 | 8/2002 | Krieg et al. |
| 6,479,504 B1 | 11/2002 | Macfarlane et al. |
| 6,521,637 B2 | 2/2003 | Macfarlane |
| 6,653,292 B1 | 11/2003 | Krieg et al. |
| 6,727,230 B1 | 4/2004 | Hutcherson et al. |
| 6,821,957 B2 | 11/2004 | Krieg et al. |
| 6,943,240 B2 | 9/2005 | Bauer et al. |
| 6,949,520 B1 | 9/2005 | Hartmann et al. |
| 7,001,890 B1 | 2/2006 | Wagner et al. |
| 2001/0044416 A1 | 11/2001 | McCluskie et al. |
| 2002/0064515 A1 | 5/2002 | Krieg et al. |
| 2002/0091097 A1 | 7/2002 | Bratzler et al. |
| 2002/0156033 A1 | 10/2002 | Bratzler et al. |
| 2002/0164341 A1 | 11/2002 | Davis et al. |
| 2002/0165178 A1 | 11/2002 | Schetter et al. |
| 2002/0198165 A1 | 12/2002 | Bratzler et al. |
| 2003/0026782 A1 | 2/2003 | Krieg et al. |
| 2003/0026801 A1 | 2/2003 | Weiner et al. |
| 2003/0050261 A1 | 3/2003 | Krieg et al. |
| 2003/0050263 A1 | 3/2003 | Krieg et al. |
| 2003/0050268 A1 | 3/2003 | Krieg et al. |
| 2003/0055014 A1 | 3/2003 | Bratzler |
| 2003/0087848 A1 | 5/2003 | Bratzler et al. |
| 2003/0091599 A1 | 5/2003 | Davis et al. |
| 2003/0100527 A1 | 5/2003 | Krieg et al. |
| 2003/0104523 A1 | 6/2003 | Bauer et al. |
| 2003/0139364 A1 | 7/2003 | Krieg et al. |
| 2003/0148316 A1 | 8/2003 | Lipford et al. |
| 2003/0148976 A1 | 8/2003 | Krieg et al. |
| 2003/0166001 A1 | 9/2003 | Lipford |
| 2003/0181406 A1 | 9/2003 | Schetter et al. |
| 2003/0191079 A1 | 10/2003 | Krieg et al. |

(Continued)

FOREIGN PATENT DOCUMENTS

EP     1 229 025 A1    8/2002

(Continued)

OTHER PUBLICATIONS

Aderounmu AF, In vitro assessment of the antimalarial activity of chloroquine and its major metabolites. Ann Trop Med Parasitol. Dec. 1984;78(6):581-5.

(Continued)

*Primary Examiner*—James O. Wilson
*Assistant Examiner*—Tamthom N Truong
(74) *Attorney, Agent, or Firm*—Wolf, Greenfield & Sacks, PC; Gregg C. Benson

(57) ABSTRACT

The invention provides methods and compositions useful for modulating signaling through Toll-like receptors. The methods involve contacting a TLR-expressing cell with a small molecule having a core structure including at least two rings. Certain of the compounds are 4-primary amino quinolines. Many of the compounds and methods are useful specifically for inhibiting immune stimulation involving at least one of TLR9, TLR8, TLR7, and TLR3. The methods may have use in the treatment of autoimmunity, inflammation, allergy, asthma, graft rejection, graft versus host disease, infection, sepsis, cancer, and immunodeficiency.

9 Claims, 5 Drawing Sheets

U.S. PATENT DOCUMENTS

| | | |
|---|---|---|
| 2003/0212026 A1 | 11/2003 | Krieg et al. |
| 2003/0224010 A1 | 12/2003 | Davis et al. |
| 2003/0232074 A1 | 12/2003 | Lipford et al. |
| 2004/0009949 A1 | 1/2004 | Krieg |
| 2004/0030118 A1 | 2/2004 | Wagner et al. |
| 2004/0053880 A1 | 3/2004 | Krieg |
| 2004/0067905 A1 | 4/2004 | Krieg |
| 2004/0087534 A1 | 5/2004 | Krieg et al. |
| 2004/0087538 A1 | 5/2004 | Krieg et al. |
| 2004/0092472 A1 | 5/2004 | Krieg |
| 2004/0106568 A1 | 6/2004 | Krieg et al. |
| 2004/0131628 A1 | 7/2004 | Bratzler et al. |
| 2004/0132685 A1 | 7/2004 | Krieg et al. |
| 2004/0142469 A1 | 7/2004 | Krieg et al. |
| 2004/0143112 A1 | 7/2004 | Krieg et al. |
| 2004/0147468 A1 | 7/2004 | Krieg et al. |
| 2004/0152649 A1 | 8/2004 | Krieg |
| 2004/0152656 A1 | 8/2004 | Krieg et al. |
| 2004/0152657 A1 | 8/2004 | Krieg et al. |
| 2004/0162258 A1 | 8/2004 | Krieg et al. |
| 2004/0162262 A1 | 8/2004 | Krieg et al. |
| 2004/0167089 A1 | 8/2004 | Krieg et al. |
| 2004/0171150 A1 | 9/2004 | Krieg et al. |
| 2004/0171571 A1 | 9/2004 | Krieg et al. |
| 2004/0181045 A1 | 9/2004 | Krieg et al. |
| 2004/0198680 A1 | 10/2004 | Krieg |
| 2004/0198688 A1 | 10/2004 | Krieg et al. |
| 2004/0229835 A1 | 11/2004 | Krieg et al. |
| 2004/0234512 A1 | 11/2004 | Wagner et al. |
| 2004/0235770 A1 | 11/2004 | Davis et al. |
| 2004/0235774 A1 | 11/2004 | Bratzler et al. |
| 2004/0235777 A1 | 11/2004 | Wagner et al. |
| 2004/0235778 A1 | 11/2004 | Wagner et al. |
| 2004/0266719 A1 | 12/2004 | McCluskie et al. |
| 2005/0004061 A1 | 1/2005 | Krieg et al. |
| 2005/0004062 A1 | 1/2005 | Krieg et al. |
| 2005/0009774 A1 | 1/2005 | Krieg et al. |
| 2005/0032734 A1 | 2/2005 | Davis et al. |
| 2005/0032736 A1 | 2/2005 | Krieg et al. |
| 2005/0037403 A1 | 2/2005 | Krieg et al. |
| 2005/0037985 A1 | 2/2005 | Krieg et al. |
| 2005/0042203 A1 | 2/2005 | Davis et al. |
| 2005/0043529 A1 | 2/2005 | Davis et al. |
| 2005/0049215 A1 | 3/2005 | Krieg et al. |
| 2005/0049216 A1 | 3/2005 | Krieg et al. |
| 2005/0054601 A1 | 3/2005 | Wagner et al. |
| 2005/0054602 A1 | 3/2005 | Krieg et al. |
| 2005/0059619 A1 | 3/2005 | Krieg et al. |
| 2005/0059625 A1 | 3/2005 | Krieg et al. |
| 2005/0070491 A1 | 3/2005 | Krieg et al. |
| 2005/0075302 A1 | 4/2005 | Hutcherson et al. |
| 2005/0100983 A1 | 5/2005 | Bauer et al. |
| 2005/0101554 A1 | 5/2005 | Krieg et al. |
| 2005/0101557 A1 | 5/2005 | Krieg et al. |
| 2005/0119273 A1 | 6/2005 | Lipford et al. |
| 2005/0123523 A1 | 6/2005 | Krieg et al. |
| 2005/0130911 A1 | 6/2005 | Uhlmann et al. |
| 2005/0148537 A1 | 7/2005 | Krieg et al. |
| 2005/0169888 A1 | 8/2005 | Hartman et al. |
| 2005/0171047 A1 | 8/2005 | Krieg et al. |
| 2005/0181422 A1 | 8/2005 | Bauer et al. |
| 2005/0182017 A1 | 8/2005 | Krieg |
| 2005/0197314 A1 | 9/2005 | Krieg et al. |
| 2005/0215501 A1 | 9/2005 | Lipford et al. |
| 2005/0233995 A1 | 10/2005 | Krieg et al. |
| 2005/0233999 A1 | 10/2005 | Krieg et al. |
| 2005/0239732 A1 | 10/2005 | Krieg et al. |
| 2005/0239733 A1 | 10/2005 | Jurk et al. |
| 2005/0239734 A1 | 10/2005 | Uhlmann et al. |
| 2005/0239736 A1 | 10/2005 | Krieg et al. |
| 2005/0244379 A1 | 11/2005 | Krieg et al. |
| 2005/0244380 A1 | 11/2005 | Krieg et al. |
| 2005/0245477 A1 | 11/2005 | Krieg et al. |
| 2005/0250726 A1 | 11/2005 | Krieg et al. |
| 2005/0256073 A1 | 11/2005 | Lipford et al. |
| 2005/0267064 A1 | 12/2005 | Krieg et al. |
| 2005/0277604 A1 | 12/2005 | Krieg et al. |
| 2005/0277609 A1 | 12/2005 | Krieg et al. |
| 2006/0003955 A1 | 1/2006 | Krieg et al. |
| 2006/0003962 A1 | 1/2006 | Ahluwalia et al. |
| 2006/0019916 A1 | 1/2006 | Krieg et al. |
| 2006/0019923 A1 | 1/2006 | Davis et al. |
| 2006/0058251 A1 | 3/2006 | Krieg et al. |
| 2006/0089326 A1 | 4/2006 | Krieg et al. |
| 2006/0094683 A1 | 5/2006 | Krieg et al. |
| 2006/0140875 A1 | 6/2006 | Krieg et al. |
| 2006/0154890 A1 | 7/2006 | Bratzler et al. |
| 2006/0172966 A1 | 8/2006 | Lipford et al. |
| 2006/0188913 A1 | 8/2006 | Krieg et al. |
| 2006/0211639 A1 | 9/2006 | Bratzler et al. |
| 2006/0211644 A1 | 9/2006 | Krieg et al. |
| 2006/0229271 A1 | 10/2006 | Krieg et al. |
| 2006/0241076 A1 | 10/2006 | Uhlmann et al. |
| 2006/0246035 A1 | 11/2006 | Ahluwalia et al. |
| 2006/0286070 A1 | 12/2006 | Hartmann et al. |
| 2006/0287263 A1 | 12/2006 | Davis et al. |
| 2007/0009482 A9 | 1/2007 | Krieg et al. |
| 2007/0010470 A9 | 1/2007 | Krieg et al. |
| 2007/0037767 A1 | 2/2007 | Bratzler et al. |
| 2007/0065467 A1 | 3/2007 | Krieg et al. |
| 2007/0066553 A1 | 3/2007 | Krieg et al. |
| 2007/0066554 A1 | 3/2007 | Krieg et al. |
| 2007/0078104 A1 | 4/2007 | Krieg et al. |
| 2007/0129320 A9 | 6/2007 | Davis et al. |
| 2007/0142315 A1 | 6/2007 | Forsbach et al. |
| 2007/0184465 A1 | 8/2007 | Wagner et al. |
| 2007/0202128 A1 | 8/2007 | Krieg et al. |
| 2007/0224210 A1 | 9/2007 | Krieg et al. |
| 2007/0232622 A1 | 10/2007 | Lipford et al. |

FOREIGN PATENT DOCUMENTS

| | | |
|---|---|---|
| WO | WO 98/29397 A1 | 7/1998 |
| WO | WO 00/15645 A1 | 3/2000 |
| WO | WO 02/062767 A1 | 8/2002 |

OTHER PUBLICATIONS

Ansari AM et al., Metabolites of chloroquine: some observations on desethychloroquine and N-acetyldesethylchloroquine. J Pharm Sci. Jul. 1994;83(7):1040-2.

De Vries PJ et al., Single-dose pharmacokinetics of chloroquine and its main metabolite in healthy volunteers. Drug Invest. 1994; 8:143-9.

Hemmi et al., Small anti-viral compounds activate immune cells via the TLR7 MyD88-dependent signaling pathway. Nat Immunol. Feb. 2002;3(2):196-200.

Jurk et al., Human TLR7 or TLR8 independently confer responsiveness to the antiviral compound R-848. Nat Immunol. Jun. 2002;3(6):499.

Manzel L et al., Antagonism of immunostimulatory CpG-oligodeoxynucleotides by 4-aminoquinolines and other weak bases: mechanistic studies. J Pharmacol Exp Ther. Dec. 1999;291(3):1337-47.

Strekowski L et al., Synthesis and activity of substituted 2-phenylquinolin-4-amines, antagonists of immunostimulatory CpG-oligodeoxynucleotides. J. Med Chem Mar. 27, 2003;46(7):1242-9.

* cited by examiner

SMALL MOLECULE TOLL-LIKE RECEPTOR (TLR) ANTAGONISTS

RELATED APPLICATIONS

This application claims priority under 35 U.S.C. 119(e) to U.S. provisional patent application Ser. No. 60/556,007, filed Mar. 23, 2004, and U.S. provisional patent application Ser. No. 60/480,588, filed Jun. 20, 2003, the entire contents of both of which are incorporated herein by reference.

FIELD OF THE INVENTION

The invention relates to generally to the field of immunology. More particularly, the invention relates to compositions and methods for altering immune function. More specifically, the invention relates to compositions and methods for affecting immune stimulation mediated through Toll-like receptor (TLR) molecules.

BACKGROUND OF THE INVENTION

Stimulation of the immune system, which includes stimulation of either or both innate immunity and adaptive immunity, is a complex phenomenon that can result in either protective or adverse physiologic outcomes for the host. In recent years there has been increased interest in the mechanisms underlying innate immunity, which is believed to initiate and support adaptive immunity. This interest has been fueled in part by the recent discovery of a family of highly conserved pattern recognition receptor proteins known as Toll-like receptors (TLRs) believed to be involved in innate immunity as receptors for pathogen-associated molecular patterns (PAMPs). Compositions and methods useful for modulating innate immunity are therefore of great interest, as they may affect therapeutic approaches to conditions involving autoimmunity, inflammation, allergy, asthma, graft rejection, graft versus host disease (GvHD), infection, cancer, and immunodeficiency.

Recently there have been a number of reports describing the immunostimulatory effect of certain types of nucleic acid molecules, including CpG nucleic acids and double-stranded RNA. Of note, it was recently reported that Toll-like receptor 9 (TLR9) recognizes bacterial DNA and CpG DNA. Hemmi H et al. (2000) *Nature* 408:740-5; Bauer S et al. (2001) *Proc Natl Acad Sci USA* 98:9237-42. It was also recently reported that immune complexes containing IgG and nucleic acid can stimulate TLR9 and participate in B-cell activation in certain autoimmune diseases. Leadbetter E A et al. (2002) *Nature* 416:595-8.

Chlroroquines have been recognized as useful not only as anti-malarial agents but also as anti-inflammatory agents. Although its mechanism of action is not well understood, chloroquine has been used effectively in the treatment of various autoimmune diseases, including rheumatoid arthritis (RA) and systemic lupus erythematosus (SLE). For a review, see Wallace D J (1996) *Lupus* 5 Suppl 1:S59-64. Recently Macfarlane and colleagues described a number of small molecule analogs and derivatives of chloroquine (4-aminoquinoline) and quinacrine (9-aminoacridine) which reportedly inhibit stimulation of the immune system. U.S. Pat. No. 6,221,882; U.S. Pat. No. 6,479,504; U.S. Pat. No. 6,521,637; PCT published application PCT/US00/16723 (WO 00/76982); and PCT published application PCT/US98/13820 (WO 99/01154). Macfarlane and colleagues report these small molecule inhibitors of the immune response, even when used at nanomolar concentrations, can block the action of immunostimulatory DNA. U.S. Pat. No. 6,221,882 B1. Macfarlane and coworkers studied a large number of compounds by varying substituents on a limited number of 4-aminoquinoline and 9-aminoacridine core structures related to chloroquine and quinacrine.

SUMMARY OF THE INVENTION

The present invention is based, in part, on the discovery by the applicants that a number of small molecules, some previously known but distinct from those described by Macfarlane et al. and by Tobe et al., can alter TLR-mediated immunostimulatory signaling. Many of the compounds inhibit TLR signaling and are useful as inhibitors of immune stimulation. Compositions and methods described herein are useful for inhibiting immune stimulation in vitro and in vivo. Such compositions and methods thus will find use in a number of clinical applications, including as pharmaceutical agents and methods for treating conditions involving unwanted immune activity, including inflammatory and autoimmune disorders. The compositions of the invention can also be used in methods for the preparation of medicaments for use in the treatment of conditions involving unwanted immune activity, including a variety of inflammatory and autoimmune disorders.

It was surprisingly discovered that molecules having similar substituents but different core structures compared to those related to chloroquine and quinacrine described by Macfarlane et al., are potent immunomodulatory small molecules. Without being bound to any theory or mechanism, it is believed that the small molecules described by the present invention affect immune stimulation via interaction with a TLR. More particularly, it is believed that many of the small molecules described by the present invention inhibit immune stimulation via TLR antagonism. In particular, it is believed that many of the small molecules described by the present invention inhibit immune stimulation via TLR9 antagonism.

The invention in certain aspects provides methods useful for altering TLR-mediated signaling. The methods of the invention are useful whenever it is desirable to alter TLR-mediated signaling in response to a suitable TLR ligand or TLR signaling agonist. For example, the methods can be used to treat any of a variety of conditions involving autoimmunity, inflammation, allergy, asthma, graft rejection, graft-versus-host disease (GvHD), infection, sepsis, cancer, and immunodeficiency. Generally, methods useful in the treatment of conditions involving autoimmunity, inflammation, allergy, asthma, graft rejection, and GvHD will employ small molecules that inhibit TLR-mediated signaling in response to a suitable TLR ligand or TLR signaling agonist. Generally, methods useful in the treatment of conditions involving infection, cancer, and immunodeficiency will employ small molecules that augment TLR-mediated signaling in response to a suitable TLR ligand. In some instances the methods can be used to inhibit or promote TLR-mediated signaling in response to a TLR ligand or TLR signaling agonist. In some instances the methods can be used to inhibit TLR-mediated immunostimulatory signaling in response to a TLR ligand or TLR signaling agonist. In some instances the methods can be used to inhibit or promote TLR-mediated immunostimulation in a subject. In some instances the methods can be used to inhibit TLR-mediated immunostimulation in a subject. In some instances the methods can be used to inhibit an immunostimulatory nucleic acid-associated response in a subject.

The invention in certain aspects provides novel small molecule compositions useful for altering TLR-mediated signaling. The compositions of the invention are useful whenever it is desirable to alter TLR-mediated signaling in response to a suitable TLR ligand or TLR signaling agonist. For example, the small molecules can be used in methods to treat any of a variety of conditions involving autoimmunity, inflammation, allergy, asthma, graft rejection, GvHD, infection, sepsis, cancer, and immunodeficiency. Generally, methods useful in the treatment of conditions involving autoimmunity, inflammation, allergy, asthma, graft rejection, and GvHD will employ small molecules that inhibit TLR-mediated signaling in response to a suitable TLR ligand or TLR signaling agonist. Generally, methods useful in the treatment of conditions involving infection, cancer, and immunodeficiency will employ small molecules that augment TLR-mediated signaling in response to a suitable TLR ligand. In some instances the molecules can be used in a method to inhibit or promote TLR-mediated signaling in response to a TLR ligand or TLR signaling agonist. In some instances the small molecules can be used in a method to inhibit TLR-mediated immunostimulatory signaling in response to a TLR ligand or TLR signaling agonist. In some instances the small molecules can be used in a method to inhibit or promote TLR-mediated immunostimulation in a subject. In some instances the small molecules can be used in a method to inhibit TLR-mediated immunostimulation in a subject. In some instances the small molecules can be used to inhibit an immunostimulatory nucleic acid-associated response in a subject.

As a feature of the present invention, the methods of the invention can be combined with administration of additional agents to achieve synergistic effect on TLR-mediated immunostimulation. More specifically, whereas the agents described herein have been discovered to affect TLRs directly and thus directly affect TLR-bearing cells, e.g., antigen-presenting cells (APCs), such agents can be used in conjunction with additional agents which affect non-APC immune cells, e.g., T lymphocytes (T cells). Such an approach effectively introduces an immunomodulatory intervention at two levels: innate immunity and acquired immunity. Since innate immunity is believed to initiate and support acquired immunity, the combination intervention is synergistic.

In one aspect of the invention, a method of affecting TLR-mediated signaling in response to a TLR ligand is provided. The method according to this aspect involves contacting a cell expressing a TLR with an effective amount of a compound of Formula I

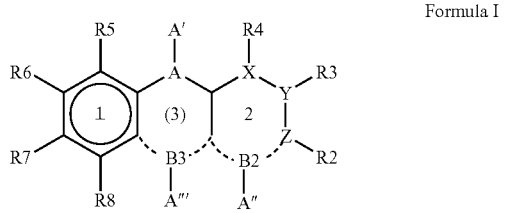

Formula I wherein 2 is a five- to seven-membered homocyclic or heterocyclic ring, wherein each of X, Y, and Z is independently chosen from a carbon atom (C), a nitrogen atom (N), an oxygen atom (O), and a sulfur atom (S), and wherein B2 optionally includes at least one atom selected from C, N, O, and S; wherein 1 and 2 are optionally bridged by B3 to form a five- to seven-membered ring (3), wherein B3 optionally includes at least one atom selected from C, N, O, and S, and wherein when A is carbon, (3) is not pyridine; wherein 2 optionally includes an unsaturated bond; wherein (1) optionally includes an unsaturated bond; wherein R2, when present, is a hydrogen atom, a substituted or unsubstituted lower alkyl, aryl, aralkyl, heterocyclic, or alkylheterocyclic group, optionally linked to Z via N, O, or S; wherein R3, R4, R5, R6, R7, and R8, when present, are each independently a hydrogen atom, a halogen atom, a substituted or unsubstituted lower alkyl, aryl, aralkyl, heterocyclic, or alkylheterocyclic group, each optionally linked via N, O, or S; wherein A is an atom selected from C, N, O, and S; wherein each of A', A", and A'" independently is R9, —NR9R10, —OR9, or —CR9R10, wherein R9 is a hydrogen atom, hydroxyl, substituted or unsubstituted lower alkyl, aryl, aralkyl, heterocyclic, or alkylheterocyclic group, and wherein R10 is optionally absent or is a hydrogen atom, lower alkyl, aryl, aralkyl, heterocyclic, or alkylheterocyclic group, to inhibit or promote TLR-mediated signaling in response to a ligand for the TLR.

In one aspect of the invention, a method of inhibiting TLR-mediated immunostimulatory signaling is provided. The method according to this aspect of the invention involves contacting a cell expressing a TLR with an effective amount of a compound of Formula I, as provided above, to inhibit TLR-mediated immunostimulatory signaling in response to a ligand for the TLR.

In one aspect the invention provides a method of affecting TLR-mediated immunostimulation in a subject. The method according to this aspect of the invention involves administering to a subject having or at risk of developing TLR-mediated immunostimulation an effective amount of a compound of Formula I, as provided above, to inhibit or promote TLR-mediated immunostimulation in the subject.

The invention in one aspect provides a method of inhibiting TLR-mediated immunostimulation in a subject. The method according to this aspect of the invention involves administering to a subject having or at risk of developing TLR-mediated immunostimulation an effective amount of a compound of Formula I, as provided above, to inhibit TLR-mediated immunostimulation in the subject.

In one aspect the invention provides a method of inhibiting an immunostimulatory nucleic acid-associated response in a subject. The method according to this aspect of the invention involves administering to a subject in need of such treatment an effective amount of a compound of Formula I, as provided above, to inhibit an immunostimulatory nucleic acid-associated response in the subject.

In one embodiment the subject is otherwise free of symptoms calling for treatment with a compound of Formula I.

In one embodiment according to any of the foregoing aspects of the invention, A is nitrogen and (3) is a five-membered ring. In one embodiment the compound is Formula II

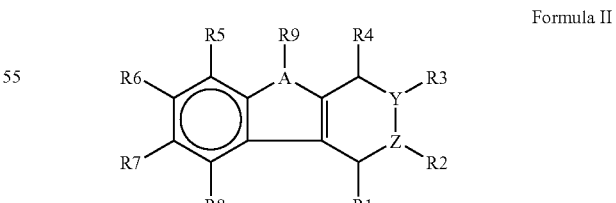

Formula II wherein A is chosen from C and N; and R1 is a hydrogen atom, a halogen atom, a substituted or unsubstituted lower alkyl, aryl, aralkyl, heterocyclic, or alkylheterocyclic group, each optionally linked via N, O, or S. In various specific embodiments the compound is any one of compounds 455, 470, 564, 568, 593, 607, 612-614, 619-621, 636, 685, 875, 878, 890, 904, 918, 939, 944, 1039, 1050, 1132, 1241, and 1243 listed in Table 5 below.

In one embodiment according to any of the foregoing aspects of the invention, A is nitrogen, (3) is a six-membered ring, and B3 is one atom selected from C, N, O, and S. In one embodiment A is nitrogen, 3 is a six-membered ring, and B3 is S. In one embodiment the compound is Formula III

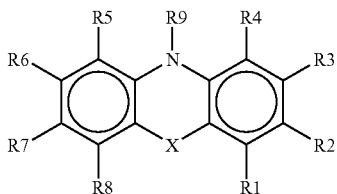

Formula III wherein R1 is a hydrogen atom, a halogen atom, a substituted or unsubstituted lower alkyl, aryl, aralkyl, heterocyclic, or alkylheterocyclic group, each optionally linked via N, O, or S, and wherein X is chosen from N, O, and S. In certain embodiments X is S. In various specific embodiments the compound is any one of compounds 53, 64, 125, 149, 313, 399, 529, 576, 693, 797, 840, and 842 listed in Table 6 below.

In one embodiment according to any of the foregoing aspects of the invention, A is carbon, (1) is a six-membered ring, and B3 is C or S. In one embodiment the compound is Formula IV

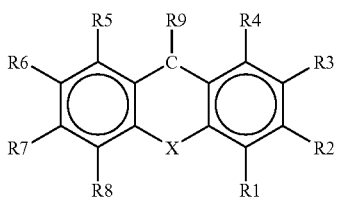

Formula IV wherein X is C or S and R1 is a hydrogen atom, a halogen atom, a substituted or unsubstituted lower alkyl, aryl, aralkyl, heterocyclic, or alkylheterocyclic group, each optionally linked via N, O, or S. In various specific embodiments the compound is any one of compounds 43, 294, 340, 346, 348, 413, 491, 917, 1015, 1042, 1158, 1287, and 1337 listed in Table 7 below.

In one embodiment according to any of the foregoing aspects of the invention, A is nitrogen, (1) is a seven-membered ring, and B3 includes two carbon atoms. In one embodiment the compound is Formula V

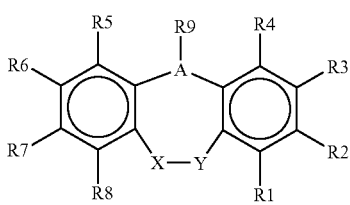

Formula V wherein X and Y are each independently C, N, O, or S; and R1 is a hydrogen atom, a halogen atom, a substituted or unsubstituted lower alkyl, aryl, aralkyl, heterocyclic, or alkylheterocyclic group, each optionally linked via N, O, or S. In various specific embodiments the compound is any one of compounds 72, 74, 99, 109, 343, 488, 1013, and 1352 listed in Table 8 below.

In one embodiment according to any of the foregoing aspects of the invention, 1 and 2 are unbridged by B3, A is carbon, and A' is —OR9. In one embodiment the compound is Formula VI

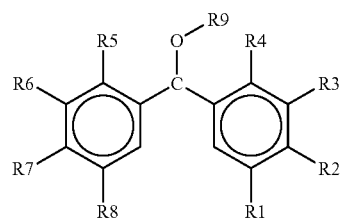

Formula VI wherein R1 is a hydrogen atom, a halogen atom, a substituted or unsubstituted lower alkyl, aryl, aralkyl, heterocyclic, or alkylheterocyclic group, each optionally linked via N, O, or S; and R9 is a substituted or unsubstituted lower alkyl, aryl, aralkyl, heterocyclic, or alkylheterocyclic group. In some embodiments R9 and R4 are united to form a lactone. In various specific embodiments the compound is any one of compounds 65, 229, 239, 306, 386, 707, 793, 957, 970, 974, 1161, and 1308 listed in Table 9 below.

In one embodiment according to any of the foregoing aspects of the invention, 1 and 2 are unbridged by B3, A is carbon, and A' is —NR9R10. In one embodiment the compound is Formula VII

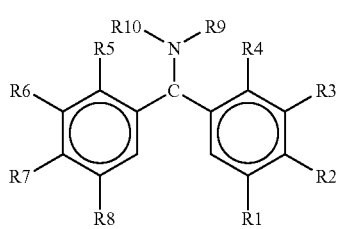

Formula VII wherein R1 is a hydrogen atom, a halogen atom, a substituted or unsubstituted lower alkyl, aryl, aralkyl, heterocyclic, or alkylheterocyclic group, each optionally linked via N, O, or S. In various specific embodiments the compound is any one of compounds 133, 267, 312, 457, and 510 listed in Table 10 below.

In one embodiment according to any of the foregoing aspects of the invention, 1 and 2 are unbridged by B3, A is carbon, and A' is CR9R10. In one embodiment the compound is Formula VIII

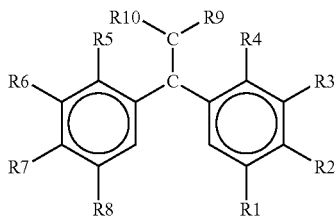

Formula VIII wherein R1 is a hydrogen atom, a halogen atom, a substituted or unsubstituted lower alkyl, aryl, aralkyl, heterocyclic, or alkylheterocyclic group, each optionally linked via N, O, or S.

In various specific embodiments the compound is any one of compounds 93, 108, 138, 144, 267, 270, 308, 381, 560, 778, 799, 822, 833, 884, 965, and 1187 listed in Table 11 below.

In one aspect the invention provides a method of affecting TLR-mediated signaling in response to a TLR ligand. The method according to this aspect of the invention involves contacting a cell expressing a TLR with an effective amount of a compound of Formula IX

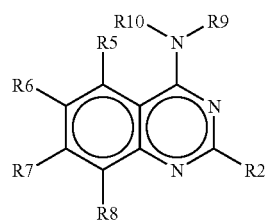

Formula IX wherein R2 is a substituted or unsubstituted lower alkyl, aryl, aralkyl, heterocyclic, or alkylheterocyclic group, each optionally linked via N, O, or S; wherein R5, R6, R7, and R8 are each independently a hydrogen atom, a halogen atom, a substituted or unsubstituted lower alkyl, aryl, aralkyl, heterocyclic, or alkylheterocyclic group, each optionally linked via N, O, or S; wherein R9 is a hydrogen atom, substituted or unsubstituted lower alkyl, aryl, aralkyl, heterocyclic, or alkylheterocyclic group; and wherein R10 is a hydrogen atom, lower alkyl, aryl, aralkyl, heterocyclic, or alkylheterocyclic group, to inhibit or promote TLR-mediated signaling in response to a ligand for the TLR. In various specific embodiments the compound is any one of compounds 751, 858, 2000, and 2001 listed in Table 12 below.

In one aspect of the invention, a method of inhibiting TLR-mediated immunostimulatory signaling is provided. The method according to this aspect of the invention involves contacting a cell expressing a TLR with an effective amount of a compound of Formula IX, as provided above, to inhibit TLR-mediated immunostimulatory signaling in response to a ligand for the TLR.

In one aspect the invention provides a method of affecting TLR-mediated immunostimulation in a subject. The method according to this aspect of the invention involves administering to a subject having or at risk of developing TLR-mediated immunostimulation an effective amount of a compound of Formula IX, as provided above, to inhibit or promote TLR-mediated immunostimulation in the subject.

The invention in one aspect provides a method of inhibiting TLR-mediated immunostimulation in a subject. The method according to this aspect of the invention involves administering to a subject having or at risk of developing TLR-mediated immunostimulation an effective amount of a compound of Formula IX, as provided above, to inhibit TLR-mediated immunostimulation in the subject.

In one aspect the invention provides a method of inhibiting an immunostimulatory nucleic acid-associated response in a subject. The method according to this aspect of the invention involves administering to a subject in need of such treatment an effective amount of a compound of Formula IX, as provided above, to inhibit an immunostimulatory nucleic acid-associated response in the subject.

In one embodiment the subject is otherwise free of symptoms calling for treatment with a compound of Formula IX.

In one aspect the invention provides a method of affecting TLR-mediated signaling in response to a TLR ligand. The method according to this aspect of the invention involves contacting a cell expressing a TLR with an effective amount of a compound of Formula X

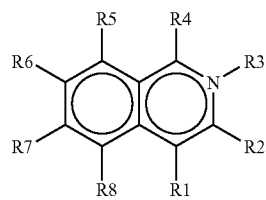

Formula X wherein each of R1, R2, R3, R4, R5, R6, R7, and R8 is independently a hydrogen atom, a halogen atom, a substituted or unsubstituted lower alkyl, aryl, aralkyl, heterocyclic, or alkylheterocyclic group, each optionally linked via N, O, or S, to inhibit or promote TLR-mediated signaling in response to a ligand for the TLR. In various specific embodiments the compound is any one of compounds 431, 583, 586, 792, and 830 listed in Table 13 below.

In one aspect of the invention, a method of inhibiting TLR-mediated immunostimulatory signaling is provided. The method according to this aspect of the invention involves contacting a cell expressing a TLR with an effective amount of a compound of Formula X, as provided above, to inhibit TLR-mediated immunostimulatory signaling in response to a ligand for the TLR.

In one aspect the invention provides a method of affecting TLR-mediated immunostimulation in a subject. The method according to this aspect of the invention involves administering to a subject having or at risk of developing TLR-mediated immunostimulation an effective amount of a compound of Formula X, as provided above, to inhibit or promote TLR-mediated immunostimulation in the subject.

The invention in one aspect provides a method of inhibiting TLR-mediated immunostimulation in a subject. The method according to this aspect of the invention involves administering to a subject having or at risk of developing TLR-mediated immunostimulation an effective amount of a compound of Formula X, as provided above, to inhibit TLR-mediated immunostimulation in the subject.

In one aspect the invention provides a method of inhibiting an immunostimulatory nucleic acid-associated response in a subject. The method according to this aspect of the invention involves administering to a subject in need of such treatment an effective amount of a compound of Formula X, as provided above, to inhibit an immunostimulatory nucleic acid-associated response in the subject.

In one embodiment the subject is otherwise free of symptoms calling for treatment with a compound of Formula X.

In one aspect the invention provides a method of affecting TLR-mediated signaling in response to a TLR ligand. The method according to this aspect of the invention involves contacting a cell expressing a TLR with an effective amount of a compound of Formula XI

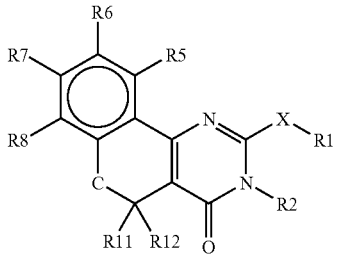

Formula XI wherein each of R1, R2, R5, R6, R7, R8, R11, and R12 is a hydrogen atom, a halogen atom, a substituted or unsubstituted lower alkyl, aryl, aralkyl, heterocyclic, or alkylheterocyclic group, each optionally linked via N, O, or S; and X is C, N, O, or S, to inhibit or promote TLR-mediated signaling in response to a ligand for the TLR. In some embodiments R2 includes a cycloalkyl, benzyl or phenyl group. In some embodiments X is N. In some embodiments R11 and R12 are linked as a spiro group in a five- or six-membered ring. In various specific embodiments the compound is any one of compounds 891, 926, 1137, 1213, 1248, 1320, and 1322 listed in Table 14 below.

In one aspect of the invention, a method of inhibiting TLR-mediated immunostimulatory signaling is provided. The method according to this aspect of the invention involves contacting a cell expressing a TLR with an effective amount of a compound of Formula XI, as provided above, to inhibit TLR-mediated immunostimulatory signaling in response to a ligand for the TLR.

In one aspect the invention provides a method of affecting TLR-mediated immunostimulation in a subject. The method according to this aspect of the invention involves administering to a subject having or at risk of developing TLR-mediated immunostimulation an effective amount of a compound of Formula XI, as provided above, to inhibit or promote TLR-mediated immunostimulation in the subject.

The invention in one aspect provides a method of inhibiting TLR-mediated immunostimulation in a subject. The method according to this aspect of the invention involves administering to a subject having or at risk of developing TLR-mediated immunostimulation an effective amount of a compound of Formula XI, as provided above, to inhibit TLR-mediated immunostimulation in the subject.

In one aspect the invention provides a method of inhibiting an immunostimulatory nucleic acid-associated response in a subject. The method according to this aspect of the invention involves administering to a subject in need of such treatment an effective amount of a compound of Formula XI, as provided above, to inhibit an immunostimulatory nucleic acid-associated response in the subject.

In one embodiment the subject is otherwise free of symptoms calling for treatment with a compound of Formula XI.

In one aspect the invention provides a method of affecting TLR-mediated signaling in response to a TLR ligand. The method according to this aspect of the invention involves contacting a cell expressing a TLR with an effective amount of a compound of Formula XII

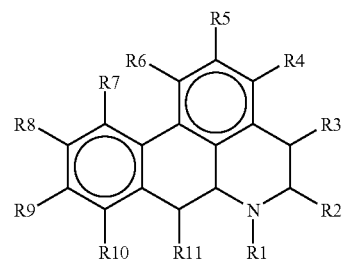

Formula XII wherein R1, R2, R3, R4, R5, R6, R7, R8, R9, R10, and R11 are each independently a hydrogen atom, a halogen atom, a substituted or unsubstituted lower alkyl, aryl, aralkyl, heterocyclic, or alkylheterocyclic group, each optionally linked via N, O, or S, to inhibit or promote TLR-mediated signaling in response to a ligand for the TLR. In various specific embodiments the compound is any one of compounds 101, 600, and 609 listed in Table 15 below.

In one aspect of the invention, a method of inhibiting TLR-mediated immunostimulatory signaling is provided. The method according to this aspect of the invention involves contacting a cell expressing a TLR with an effective amount of a compound of Formula XII, as provided above, to inhibit TLR-mediated immunostimulatory signaling in response to a ligand for the TLR.

In one aspect the invention provides a method of affecting TLR-mediated immunostimulation in a subject. The method according to this aspect of the invention involves administering to a subject having or at risk of developing TLR-mediated immunostimulation an effective amount of a compound of Formula XII, as provided above, to inhibit or promote TLR-mediated immunostimulation in the subject.

The invention in one aspect provides a method of inhibiting TLR-mediated immunostimulation in a subject. The method according to this aspect of the invention involves administering to a subject having or at risk of developing TLR-mediated immunostimulation an effective amount of a compound of Formula XII, as provided above, to inhibit TLR-mediated immunostimulation in the subject.

In one aspect the invention provides a method of inhibiting an immunostimulatory nucleic acid-associated response in a subject. The method according to this aspect of the invention involves administering to a subject in need of such treatment an effective amount of a compound of Formula XII, as provided above, to inhibit an immunostimulatory nucleic acid-associated response in the subject.

In one embodiment the subject is otherwise free of symptoms calling for treatment with a compound of Formula XII.

In one aspect the invention provides a method of affecting TLR-mediated signaling in response to a TLR ligand. The method according to this aspect of the invention involves contacting a cell expressing a TLR with an effective amount of a compound of Formula XIII

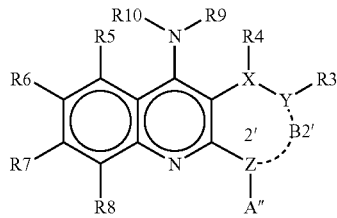

Formula XIII wherein 2' is a five- to seven-membered heterocyclic ring, wherein each of X, Y, and Z is independently chosen from C, N, O, and S, and wherein B2' optionally includes at least one atom selected from C, N, O, and S; wherein 2' optionally includes an unsaturated bond; wherein R4, R5, R6, R7, and R8 are each independently a hydrogen atom, a halogen atom, a substituted or unsubstituted lower alkyl, aryl, aralkyl, heterocyclic, or alkylheterocyclic group, each optionally linked via N, O, or S; wherein R9 is a hydrogen atom, substituted or unsubstituted lower alkyl, aryl, aralkyl, heterocyclic, or alkylheterocyclic group; wherein R10 is a hydrogen atom, lower alkyl, aryl, aralkyl, heterocyclic, or alkylheterocyclic group; and wherein A" is hydrogen, a substituted or unsubstituted lower alkyl, aryl, aralkyl, heterocyclic, or alkylheterocyclic group, to inhibit or promote TLR-mediated signaling in response to a ligand for the TLR. In various specific embodiments the compound is any one of compounds 990, 1003, 1091, 1142, 1185, 1212, 1217, 1224, 1244, and 1334 listed in Table 16 below.

In one aspect of the invention, a method of inhibiting TLR-mediated immunostimulatory signaling is provided. The method according to this aspect of the invention involves contacting a cell expressing a TLR with an effective amount of a compound of Formula XIII, as provided above, to inhibit TLR-mediated immunostimulatory signaling in response to a ligand for the TLR.

In one aspect the invention provides a method of affecting TLR-mediated immunostimulation in a subject. The method according to this aspect of the invention involves administering to a subject having or at risk of developing TLR-mediated immunostimulation an effective amount of a compound of Formula XIII, as provided above, to inhibit or promote TLR-mediated immunostimulation in the subject.

The invention in one aspect provides a method of inhibiting TLR-mediated immunostimulation in a subject. The method according to this aspect of the invention involves administering to a subject having or at risk of developing TLR-mediated immunostimulation an effective amount of a compound of Formula XIII, as provided above, to inhibit TLR-mediated immunostimulation in the subject.

In one aspect the invention provides a method of inhibiting an immunostimulatory nucleic acid-associated response in a subject. The method according to this aspect of the invention involves administering to a subject in need of such treatment an effective amount of a compound of Formula XIII, as provided above, to inhibit an immunostimulatory nucleic acid-associated response in the subject.

In each of the foregoing aspects involving a compound of Formula XIII, in one embodiment A" is a substituted alkyl group selected from the group consisting of a cyclic amino group, an alkylamino group, a dialkylamino group, furyl, phenyl, thienyl, azabicyclooctyl, azabicycloheptyl, and any combination thereof. In one embodiment the cyclic amino group is a piperazino group, a piperidino group, a pyrrolidino group, an imidazolyl group, a pyridyl group, or a morpholino group.

In one embodiment the subject is otherwise free of symptoms calling for treatment with a compound of Formula XIII.

In one aspect the invention provides a method of affecting TLR-mediated signaling in response to a TLR ligand. The method according to this aspect of the invention involves contacting a cell expressing a TLR with an effective amount of a compound of Formula XIV or Formula XV

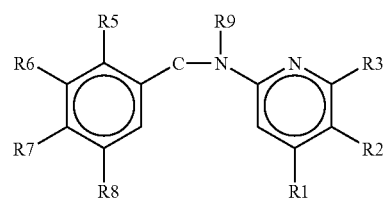

Formula XIV

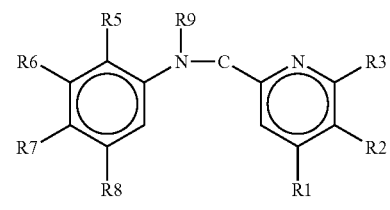

Formula XV wherein R1, R2, R3, R5, R6, R7, and R8 are each independently a hydrogen atom, a halogen atom, a substituted or unsubstituted lower alkyl, aryl, aralkyl, heterocyclic, or alkylheterocyclic group, each optionally linked via N, O, or S; and wherein R9 is a hydrogen atom, substituted or unsubstituted lower alkyl, aryl, aralkyl, heterocyclic, or alkylheterocyclic group, to inhibit or promote TLR-mediated signaling in response to a ligand for the TLR. In various specific embodiments the compound is any one of compounds 807, 1163, and 1367 listed in Table 17 below.

In one aspect of the invention, a method of inhibiting TLR-mediated immunostimulatory signaling is provided. The method according to this aspect of the invention involves contacting a cell expressing a TLR with an effective amount of a compound of Formula XIV or Formula XV, as provided above, to inhibit TLR-mediated immunostimulatory signaling in response to a ligand for the TLR.

In one aspect the invention provides a method of affecting TLR-mediated immunostimulation in a subject. The method according to this aspect of the invention involves administering to a subject having or at risk of developing TLR-mediated immunostimulation an effective amount of a compound of Formula XIV or Formula XV, as provided above, to inhibit or promote TLR-mediated immunostimulation in the subject.

The invention in one aspect provides a method of inhibiting TLR-mediated immunostimulation in a subject. The method according to this aspect of the invention involves administering to a subject having or at risk of developing TLR-mediated immunostimulation an effective amount of a compound of Formula XIV or Formula XV, as provided above, to inhibit TLR-mediated immunostimulation in the subject.

In one aspect the invention provides a method of inhibiting an immunostimulatory nucleic acid-associated response in a subject. The method according to this aspect of the invention involves administering to a subject in need of such treatment an effective amount of a compound of Formula XIV or Formula XV, as provided above, to inhibit an immunostimulatory nucleic acid-associated response in the subject.

In one embodiment the subject is otherwise free of symptoms calling for treatment with a compound of Formula XIV or Formula XV.

In each of the foregoing aspects of the invention, in some embodiments R2 is a substituted or unsubstituted phenyl, naphthyl, phenanthryl, styryl, azabicyclooctane, or azabicycloheptane group. In some embodiments R2 is a phenyl, naphthyl, phenanthryl, styryl, azabicyclooctane, or azabicycloheptane group substituted with one or more substituent groups selected from the group consisting of an alkyl group, an alkoxy group, an alkoxyalkyl group, an ester group, an alkylamino group, a dialkylamino group, a cyclic amino group, a halogen atom, and any combination thereof. In some embodiments R2 is a phenyl, naphthyl, phenanthryl, styryl, azabicyclooctane, or azabicycloheptane group substituted with one or more substituent groups selected from the group consisting of an alkylamino group, a dialkylamino group, and a cyclic amino group. In some embodiments the cyclic amino group is a piperazino group, a piperidino group, a pyrrolidino group, an imidazolyl group, a pyridyl group, or a morpholino group.

In each of the foregoing aspects of the invention, in some embodiments R9 is a substituted alkyl group selected from the group consisting of a cyclic amino group, an alkylamino group, a dialkylamino group, furyl, phenyl, thienyl, azabicyclooctyl, azabicycloheptyl, and any combination thereof. In some embodiments the cyclic amino group is a piperazino group, a piperidino group, a pyrrolidino group, an imidazolyl group, a pyridyl group, or a morpholino group.

In the foregoing aspects of the invention, in some embodiments each of R4 and R5 is hydrogen atom. In some embodiments each of R5 and R8 is a hydrogen atom. In some embodiments each of R4, R5, and R8 is a hydrogen atom. In some embodiments R10 is a hydrogen atom.

In each of the foregoing aspects of the invention, in one embodiment the TLR is TLR9. In one embodiment the ligand for the TLR is an immunostimulatory nucleic acid. In one embodiment the immunostimulatory nucleic acid is a CpG nucleic acid.

In each of the foregoing aspects of the invention, in one embodiment the TLR is TLR8. In one embodiment the ligand for the TLR is a natural ligand for TLR8. In one embodiment the ligand for the TLR is resiquimod (R848).

In each of the foregoing aspects of the invention, in one embodiment the TLR is TLR7. In one embodiment the ligand for the TLR is a natural ligand for TLR7. In one embodiment the ligand for the TLR is R848.

In each of the foregoing aspects of the invention, in one embodiment the TLR is TLR3. In one embodiment the ligand for the TLR is a double stranded RNA. In one embodiment the ligand for the TLR is poly(I:C).

The present invention is based, in part, on the appreciation by the applicants of a potential connection between the antimalarial activity of known metabolites of chloroquine and the biological activity of related small molecules with respect to inhibition of TLR9. For chloroquine, the major metabolites are mono de-ethylated chloroquine and bis de-ethylated chloroquine.

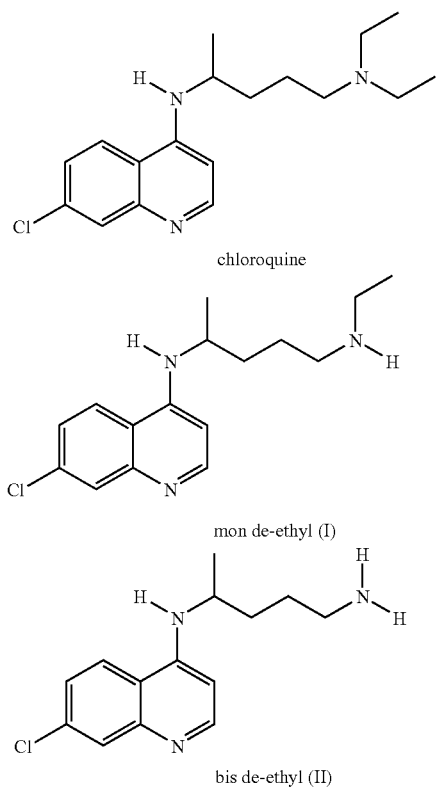

chloroquine mon de-ethyl (I)

bis de-ethyl (II)

The half life of mono de-ethylchloroquine in humans is 1.5 times longer than that of chloroquine (649 hrs versus 432 hrs). de Vries P J et al. (1994) *Drug Invest* 8:143-9. Data for bis de-ethylchloroquine is not available. In addition, the major metabolites of hydroxychloroquine are de-ethylhydroxychloroquine, mono de-ethylchloroquine, and bis de-ethylchloroquine. In the treatment of malaria the potency of chloroquine and mono de-ethylchloroquine against *Plasmodium falciparum* are about equal whereas bis de-ethylchloroquine is about half as active. Aderounmu A F (1984) *Ann Trop Med Parasitol.* 78(6):581-5. Also since the side chain is chiral, R and S chloroquine have differing activities with the (S)-(+)-mono de-ethylchloroquine being preferentially produced. Ansari A M et al. (1994) *J Pharm Sci.* 83(7):1040-2. It was thus hypothesized by the applicants that both chloroquine and hydroxychloroquine derive a substantial portion of their efficacy from the long lived de-ethyl metabolite and that this relationship may carry over to the binding to TLR9.

It turns out that chloroquine, hydroxychloroquine, mono de-ethylchloroquine, and bis de-ethylchloroquine have been examined by Macfarlane. The IC50 of these compounds by his assay were: chloroquine, $1.1 \times 10^{-7}$M; hydroxychloroquine, $4.1 \times 10^{-7}$M; mono de-ethylchloroquine, $7.08 \times 10^{-7}$M; and bis de-ethylchloroquine, $18.6 \times 10^{-7}$M. So by this data the loss of one ethyl group from chloroquine reduced the potency by about 7-fold and the loss of both ethyl groups reduced the potency by about 18-fold.

The present invention in certain aspects is related to compositions and methods involving certain 4-primary amino quinoline compounds which are useful for inhibiting TLR9 signaling and immune activation. In certain aspects the present invention is also related to compositions and methods involving certain quinazoline compounds, some of which are structurally related to the 4-primary amino quinoline compounds of the invention, which are also useful for inhibiting TLR9 signaling and immune activation.

It was surprisingly discovered according to the invention that the 4-primary amino quinoline compounds and the quinazoline compounds of the invention are highly and similarly active as inhibitors of TLR9 signaling activity. It was also surprisingly discovered according to the instant invention that despite their high degree of structural and biological similarity, the quinazoline molecules exhibit a significantly improved toxicity profile in vivo compared with the quinoline compounds.

In one aspect the invention provides novel substituted 4-primary amino quinoline compositions having a structural Formula XVI

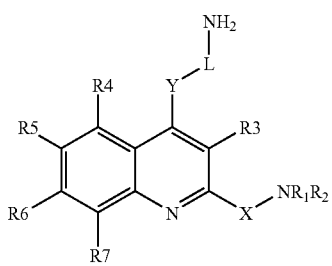

Formula XVI wherein

X is absent or is an aryl, alkyl, heterocyclic, or styryl group;

$R_1$ and $R_2$ are each independently a hydrogen atom or a substituted or unsubstituted alkyl, alkenyl, or aryl group, wherein $R_1$ and $R_2$ optionally are combined to form a heterocycle;

$R_3$ is a hydrogen atom, a halogen atom, or an alkyl, alkenyl, aryl, heterocyclic, nitro, cyano, carboxy, ester, ketone, amino, amido, hydroxy, alkoxy, mercapto, thio, sulfoxide, sulfone, or sulfonamido group, wherein $R_1$ and $R_3$ optionally are combined to form a heterocycle;

Y is absent or is an oxygen atom, a sulfur atom, $CR_8R_9$, or $NR_{10}$, where $R_8$, $R_9$, and $R_{10}$ are each independently a hydrogen atom or a substituted or unsubstituted alkyl, alkenyl, or aryl group;

L is an alkyl or alkenyl group containing from 1 to 10 carbons or is an aryl group; and $R_4$, $R_5$, $R_6$, and $R_7$ are each independently a hydrogen atom, a halogen atom, or an alkyl, alkenyl, aryl, heterocyclic, nitro, cyano, carboxy, ester, ketone, amino, amido, hydroxy, alkoxy, mercapto, thio, sulfoxide, sulfone, or sulfonamido group, wherein any pair of $R_4$, $R_5$, $R_6$, and $R_7$ which are adjacent one another optionally are combined to form a heterocycle or a carbocycle, and pharmaceutically acceptable hydrates and salts thereof.

In one embodiment $R_5$ and $R_6$ are each independently a halogen atom or an alkoxy group. In one embodiment $R_5$ and $R_6$ are each independently a chlorine atom or a methoxy group.

In one embodiment X is absent or is an aryl group;

$NR_1R_2$ is a heterocyclic amine or is $NR_8(CH_2)_nNR_9R_{10}$, wherein n is an integer from 2 to 6, inclusive, and $R_8$, $R_9$, and $R_{10}$ are each independently a hydrogen atom or an alkyl group;

$R_3$ is a hydrogen atom;

Y is an aryl group or is $NR_{11}$ where $R_{11}$ is a hydrogen atom or an aryl or alkyl group;

L is absent or is a $C_2$-$C_6$ alkyl group; and $R_4$, $R_5$, $R_6$, and $R_7$ are each independently a hydrogen atom, a halogen atom, or an alkoxy group.

In one embodiment X is absent or is an aryl group;

$NR_1R_2$ is a substituted or unsubstituted piperazino or morpholino group or is $NR_8(CH_2)_nNR_9R_{10}$, wherein n is an integer from 2 to 6, inclusive, $R_8$ is a hydrogen atom, and $R_9$ and $R_{10}$ are each independently an alkyl group;

$R_3$ is a hydrogen atom;

Y is NH;

L is a $C_2$-$C_6$ alkyl group; and $R_4$, $R_5$, $R_6$, and $R_7$ are each independently a hydrogen atom, a halogen atom, or an alkoxy group.

In one embodiment X is a phenyl group;

$NR_1R_2$ is

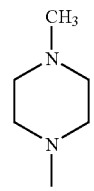

attached to a para position of the phenyl group X;

Y is NH;

L is —$(CH_2)_n$— where n is an integer between 2 and 6, inclusive; and each of $R_3$, $R_4$, $R_5$, $R_6$, and $R_7$ is a hydrogen atom.

In each of the foregoing embodiments, the composition is optionally in the form of a pharmaceutically acceptable hydrate or salt.

In one aspect the invention provides a method for inhibiting signaling by a TLR. The method according to this aspect of the invention involves contacting a cell expressing a functional TLR with an effective amount of a substituted 4-primary amino quinoline composition having structural Formula XVII

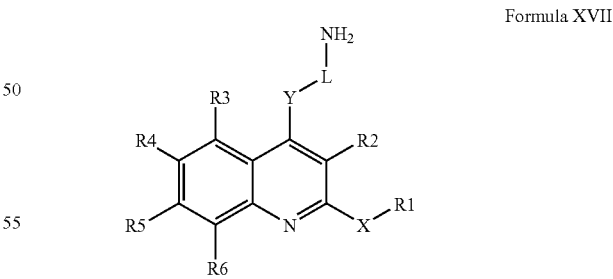

Formula XVII wherein

X is absent or is a nitrogen, oxygen, or sulfur atom or an SO or $SO_2$ group;

$R_1$ is a hydrogen atom or a substituted or unsubstituted aryl, alkyl, heterocyclic or styryl group;

$R_2$ is a hydrogen atom, a halogen atom, or an alkyl, alkenyl, aryl, heterocyclic, nitro, cyano, carboxy, ester, ketone, amino, amido, hydroxy, alkoxy, mercapto, thio, sulfoxide, sulfone, or sulfonamido group, wherein $R_1$ and $R_2$ optionally are combined to form a heterocycle or carbocycle;

Y is absent or is an oxygen atom, a sulfur atom, $CR_7R_8$, or $NR_9$, where $R_7$, $R_8$, and $R_9$ are each independently a hydrogen atom or a substituted or unsubstituted alkyl, alkenyl, or aryl group;

L is absent or is an alkyl or alkenyl group containing from 1 to 10 carbons or is an aryl group; and $R_3$, $R_4$, $R_5$, and $R_6$ are each independently a hydrogen atom, a halogen atom, or an alkyl, alkenyl, aryl, heterocyclic, nitro, cyano, carboxy, ester, ketone, amino, amido, hydroxy, alkoxy, mercapto, thio, sulfoxide, sulfone, or sulfonamido group, wherein any pair of $R_3$, $R_4$, $R_5$, and $R_6$ which are adjacent one another optionally are combined to form a heterocycle or a carbocycle, and pharmaceutically acceptable hydrates and salts thereof, to inhibit signaling by the TLR.

In one aspect the invention provides a method for inhibiting signaling by a TLR. The method according to this aspect of the invention involves contacting an immune cell expressing a functional TLR with (a) an effective amount of a TLR signal agonist to stimulate signaling by the TLR in absence of a substituted 4-primary amino quinoline composition, and (b) an effective amount of a substituted 4-primary amino quinoline composition having structural Formula XVII, as defined above, to inhibit signaling by the TLR in response to the TLR signal agonist compared with the signaling by the TLR in response to the TLR signal agonist in absence of the substituted 4-primary amino quinoline composition.

In one embodiment the TLR is TLR9 and the TLR signal agonist is a TLR9 signal agonist. The TLR signal agonist in one embodiment is CpG DNA, which can be an oligodeoxynucleotide (ODN).

In one embodiment the TLR signal agonist is an immune complex. In one embodiment the TLR signal agonist is an immune complex that includes a nucleic acid. In one embodiment the TLR signal agonist is an immune complex that includes a nucleic acid that is self-DNA. In one embodiment the TLR signal agonist is an immune complex that includes a nucleic acid that is self-RNA.

In one aspect the invention provides a method for inhibiting an immune response to an antigenic substance. The method according to this aspect of the invention involves contacting an immune cell expressing a functional Toll-like receptor with (a) an effective amount of an antigenic substance to stimulate an immune response to the antigenic substance in absence of a substituted 4-primary amino quinoline composition, and (b) an effective amount of a substituted 4-primary amino quinoline composition having structural Formula XVII, as defined above, to inhibit an immune response to the antigenic substance compared with the immune response to the antigenic substance in absence of the substituted 4-primary amino quinoline composition.

In one embodiment the immune response is an innate immune response. In one embodiment the immune response includes an adaptive immune response.

In one aspect of the invention, a method of treating an autoimmune disorder in a subject is provided. The method according to this aspect of the invention involves the step of administering to a subject having an autoimmune disorder an effective amount of a substituted 4-primary amino quinoline composition having structural Formula XVII, as defined above, to treat the autoimmune disorder. In one embodiment the autoimmune disorder is chosen from systemic lupus erythematosus, rheumatoid arthritis, inflammatory bowel disease, Sjögren's syndrome, polymyositis, vasculitis, Wegener's granulomatosis, sarcoidosis, ankylosing spondylitis, Reiter's syndrome, psoriatic arthritis, and Behçet's syndrome. In one particular embodiment the autoimmune disease is systemic lupus erythematosus. In one particular embodiment the autoimmune disease is rheumatoid arthritis. In one embodiment the subject is a human. In one embodiment the autoimmune disorder is an immune complex associated disease.

In one aspect the invention provides novel quinazoline compositions of the invention having a structural Formula XVIII

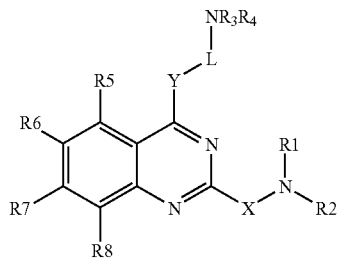

Formula XVIII wherein

X is absent or is an aryl, alkyl, heterocyclic or styryl group, provided that if X is a phenyl group, $NR_1R_2$ is part if a heterocycle or is a diamine;

$R_1$ and $R_2$ are each independently a hydrogen atom or an alkyl, alkenyl, or aryl group, wherein $R_1$ and $R_2$ optionally are combined to form a heterocycle;

Y is an oxygen atom, a sulfur atom, $CR_9R_{10}$, or $NR_{11}$, where $R_9$, $R_{10}$, and $R_{11}$ are each independently a hydrogen atom or an alkyl, alkenyl, or aryl group, wherein any one of $R_9$, $R_{10}$, and $R_{11}$ optionally is combined with $R_3$ or $R_4$ to form a substituted or unsubstituted heterocycle;

L is an alkyl or alkenyl group containing from 1 to 10 carbons or is an aryl group;

$R_3$ and $R_4$ are each independently a hydrogen atom or an alkyl, alkenyl, or aryl group, wherein $R_3$ and $R_4$ optionally are combined to form a heterocycle; and $R_5$, $R_6$, $R_7$, and $R_8$ are each independently a hydrogen atom, a halogen atom, or an alkyl, alkenyl, aryl, heterocyclic, nitro, cyano, carboxy, ester, ketone, amino, amido, hydroxy, alkoxy, mercapto, thio, sulfoxide, sulfone, or sulfonamido group, wherein any pair of $R_5$, $R_6$, $R_7$, and $R_8$ which are adjacent one another optionally are combined to form a heterocycle or a carbocycle, and pharmaceutically acceptable hydrates and salts thereof.

In one embodiment $R_6$ and $R_7$ are each independently a halogen atom or an alkoxy group.

In one embodiment $R_6$ and $R_7$ are each independently a chlorine atom or a methoxy group.

In one embodiment X is absent or is an aryl group;

$NR_1R_2$ is a heterocyclic amine or $NR_{13}(CH_2)_nNR_{14}R_{15}$, wherein n is an integer from 2 to 6, inclusive, and $R_{13}$, $R_{14}$, and $R_{15}$ are each independently a hydrogen atom or an alkyl group;

Y is an aryl group or is $NR_{12}$ where $R_{12}$ is a hydrogen atom or an aryl or alkyl group;

L is absent or is a $C_2$-$C_6$ alkyl group;

$R_3$ and $R_4$ are each independently a hydrogen atom or an alkyl group, wherein $R_3$ and $R_4$ optionally are combined to form a heterocycle; and $R_5$, $R_6$, $R_7$, and $R_8$ are each independently a hydrogen atom, a halogen atom, or an alkoxy group.

In one embodiment X is absent or is an aryl group;

$NR_1R_2$ is a substituted or unsubstituted piperazino or morpholino group or is $NR_{13}(CH_2)_nNR_{14}R_{15}$, wherein n is an integer from 2 to 6, inclusive, $R_{13}$ is a hydrogen atom, and $R_{14}$ and $R_{15}$ are each independently an alkyl group;

Y is NH;

L is a $C_2$-$C_6$ alkyl group;

$R_3$ and $R_4$ are each independently a hydrogen atom or an alkyl group, wherein $R_3$ and $R_4$ optionally are combined to form a heterocycle; and $R_5$, $R_6$, $R_7$, and $R_8$ are each independently a hydrogen atom, a halogen atom, or an alkoxy group.

In one embodiment X is an aryl group;

$NR_1R_2$ is substituted or unsubstituted piperazino or morpholino group;

Y is NH;

L is a $C_2$-$C_6$ alkyl group;

$R_3$ and $R_4$ are each independently a methyl or ethyl group or $R_3$ and $R_4$ optionally are combined to form a morpholino group; and $R_5$, $R_6$, $R_7$, and $R_8$ are each independently a hydrogen atom, a halogen atom, or an alkoxy group.

In one embodiment X is a phenyl group;

$NR_1R_2$ is N-methylpiperazine;

Y is NH;

L is —$CH_2CH_2$—;

$R_3$ and $R_4$ are each a methyl group; and $R_5$, $R_6$, $R_7$, and $R_8$ are each a hydrogen atom.

In one embodiment X is a phenyl group;

$NR_1R_2$ is N-methylpiperazine;

Y is NH;

L is —$CH_2CH_2$—;

$R_3$ and $R_4$ are combined as a morpholino group; and $R_5$, $R_6$, $R_7$, and $R_8$ are each a hydrogen atom.

In one embodiment X is absent;

$NR_1R_2$ is a substituted or unsubstituted piperazino or morpholino group;

Y is NH;

L is a $C_2$-$C_6$ alkyl group;

$R_3$ and $R_4$ are each independently a methyl or ethyl group or $R_3$ and $R_4$ optionally are combined to form a morpholino group; and $R_5$, $R_6$, $R_7$, and $R_8$ are each independently a hydrogen atom, a halogen atom, or an alkoxy group.

In one embodiment X is absent;

$NR_1R_2$ is N-methylpiperazine;

Y is NH;

L is —$CH_2CH_2$—;

$R_3$ and $R_4$ are each a methyl group;

$R_6$ and $R_7$ are each a methoxy group; and $R_5$ and $R_9$ are each a hydrogen atom.

In one embodiment X is absent;

$NR_1R_2$ is N-phenylpiperazine;

Y is NH;

L is —$CH_2CH_2$—;

$R_3$ and $R_4$ are each a methyl group;

$R_6$ and $R_7$ are each a methoxy group; and $R_5$ and $R_8$ are each a hydrogen atom.

In one embodiment X is absent;

$NR_1R_2$ is N-methylpiperazine;

Y is NH;

L is —$CH_2CH_2$;

$R_3$ and $R_4$ are combined as a morpholino group;

$R_6$ and $R_7$ are each a methoxy group; and $R_5$ and $R_8$ are each a hydrogen atom.

In each of the foregoing embodiments, the composition is optionally in the form of a pharmaceutically acceptable hydrate or salt.

In one aspect the invention provides a method for inhibiting signaling by a TLR. The method according to this aspect of the invention involves contacting a cell expressing a functional TLR with an effective amount of quinazoline composition having structural Formula XIX

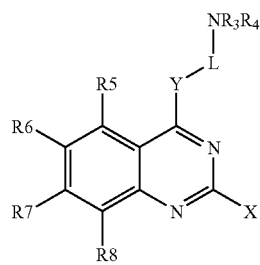

Formula XIX wherein

X is a substituted or unsubstituted aryl, alkyl, heterocyclic or styryl group, optionally attached to the quinazoline by a nitrogen, oxygen, or sulfur atom or by a SO or $SO_2$ group;

Y is absent or is an oxygen atom, a sulfur atom, $CR_9R_{10}$, or $NR_{11}$, where $R_9$, $R_{10}$, and $R_{11}$ are each independently a hydrogen atom or an alkyl, alkenyl, or aryl group, wherein any one of $R_9$, $R_{10}$, and $R_{11}$ optionally is combined with $R_3$ or $R_4$ to form a heterocycle;

L is absent or is a hydrogen atom, an alkyl or alkenyl group containing from 1 to 10 carbons, or an aryl group;

$R_3$ and $R_4$ are each independently a hydrogen atom or an alkyl, alkenyl, or aryl group, wherein $R_3$ and $R_4$ optionally are combined to form a heterocycle; and $R_5$, $R_6$, $R_7$, and $R_8$ are each independently a hydrogen atom, a halogen atom, or an alkyl, alkenyl, aryl, heterocyclic, nitro, cyano, carboxy, ester, ketone, amino, amido, hydroxy, alkoxy, mercapto, thio, sulfoxide, sulfone, or sulfonamido group, wherein any pair of $R_5$, $R_6$, $R_7$, and $R_8$ which are adjacent one another optionally are combined to form a heterocycle or a carbocycle, and pharmaceutically acceptable hydrates and salts thereof, to inhibit signaling by the TLR.

In one aspect the invention provides a method for inhibiting signaling by a TLR. The method according to this aspect of the invention involves contacting an immune cell expressing a functional TLR with (a) an effective amount of a TLR signal agonist to stimulate signaling by the TLR in absence of a quinazoline composition, and (b) an effective amount of a quinazoline composition having structural Formula XIX, as defined above, to inhibit signaling by the TLR in response to the TLR signal agonist compared with the signaling by the TLR in response to the TLR signal agonist in absence of the quinazoline composition.

In one embodiment the TLR is TLR9 and the TLR signal agonist is a TLR9 signal agonist. The TLR signal agonist in one embodiment is CpG DNA, which can be an oligodeoxynucleotide (ODN).

In one embodiment the TLR signal agonist is an immune complex that includes a nucleic acid.

In one aspect the invention provides a method for inhibiting an immune response to an antigenic substance. The method according to this aspect of the invention involves contacting an immune cell expressing a functional Toll-like receptor with (a) an effective amount of an antigenic substance to stimulate an immune response to the antigenic substance in absence of a quinazoline composition, and (b) an effective amount of a quinazoline composition having structural Formula XIX, as defined above, to inhibit an immune response to the antigenic substance compared with the immune response to the antigenic substance in absence of the quinazoline composition.

In one embodiment the immune response is an innate immune response. In one embodiment the immune response includes an adaptive immune response.

In one aspect of the invention, a method of treating an autoimmune disorder in a subject is provided. The method according to this aspect of the invention involves the step of administering to a subject having an autoimmune disorder an effective amount of a quinazoline composition having structural Formula XIX, as defined above, to treat the autoimmune disorder. In one embodiment the autoimmune disorder is chosen from systemic lupus erythematosus, rheumatoid arthritis, inflammatory bowel disease, Sjögren's syndrome, polymyositis, vasculitis, Wegener's granulomatosis, sarcoidosis, ankylosing spondylitis, Reiter's syndrome, psoriatic arthritis, and Behçet's syndrome. In one particular embodiment the autoimmune disease is systemic lupus erythematosus. In one particular embodiment the autoimmune disease is rheumatoid arthritis. In one embodiment the subject is a human. In one embodiment the autoimmune disorder is an immune complex associated disease, as described above.

BRIEF DESCRIPTION OF THE DRAWINGS

FIG. 2 is a pair of graphs depicting results of an in vivo toxicity assay in mice for specific quinoline and quinazoline compounds.

DETAILED DESCRIPTION OF THE INVENTION

Figure 1:
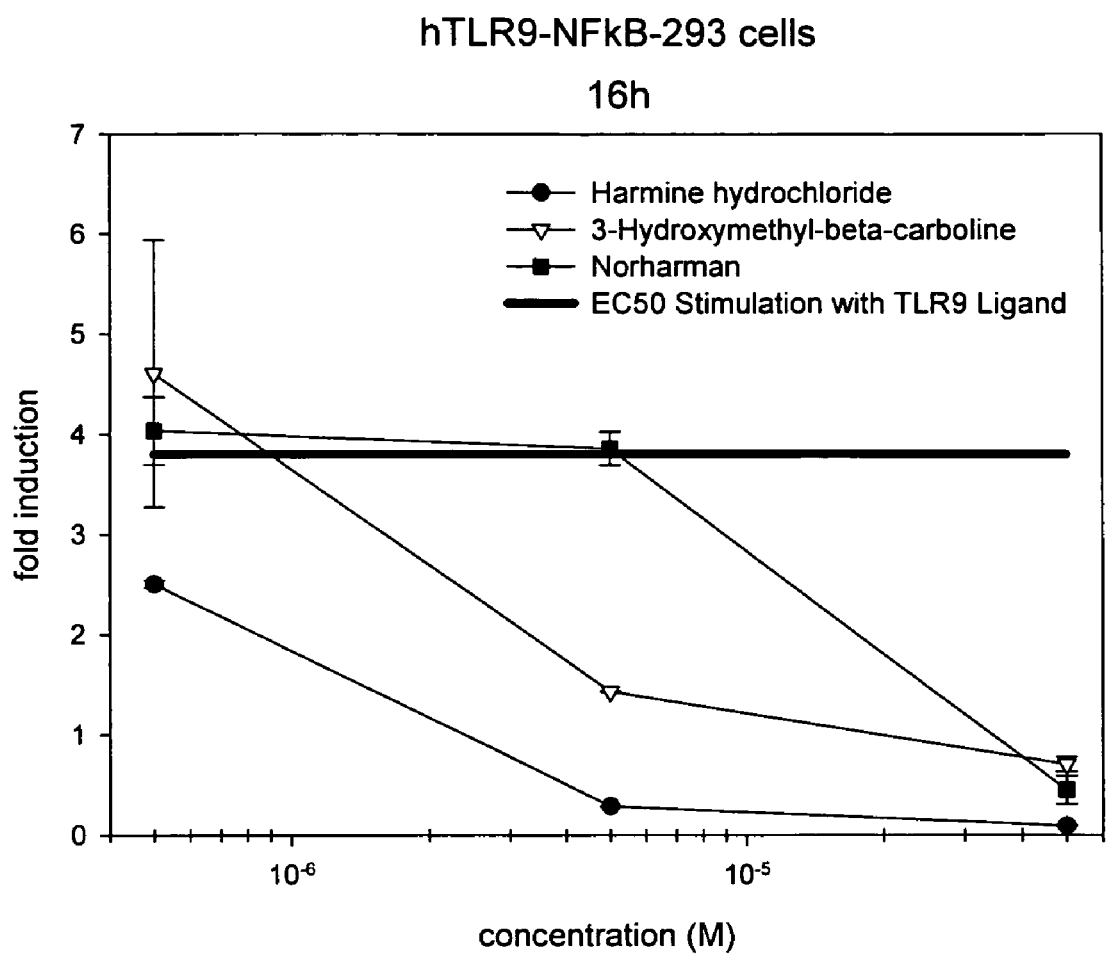
FIG. 1 is a graph depicting the concentration-dependent inhibition of TLR9 signaling in response to CpG ODN 2006 (5'-TCGTCGTTTTGTCGTTTTGTCGTT-3'; SEQ ID NO:1) by compounds 613 (harmine hydrochloride), 878 (3-hydroxymethyl-beta-carboline, and 470 (norharman), molecules representative of compounds of Formula II.

The present invention provides novel compositions and methods for inhibiting immune responses, including immune responses involved in clinical disorders characterized as autoimmune disorders and immune complex associated diseases. In addition to the novel compositions disclosed herein, which include 4-primary amino quinolines and structurally similar quinazolines, the invention also provides methods for use of previously known compositions within these and other classes of compounds in inhibiting immune responses, including immune responses involved in clinical disorders characterized as autoimmune disorders and immune complex associated diseases.

The present invention is based in part on discoveries made by the applicants arising from screening a library of small molecule compounds in an in vitro assay of TLR9 signaling in response to immunostimulatory CpG oligodeoxynucleotides (ODN). It was observed that certain of the small molecules in the library were effective in altering TLR9 signaling in response to CpG ODN. Based on the initial screening results, additional compounds were selected for additional screening. Importantly, the small molecules so identified were distinct from those described by Macfarlane and colleagues.

It has now been discovered according to the present invention that certain small molecules characterized by certain minimum features are able to modulate TLR signaling, e.g., in the presence of or in response to a PAMP or other TLR ligand. Some of the small molecules are potent inhibitors of TLR signaling and thus can be used to inhibit TLR-mediated immunostimulation. The minimal features for many, but not all, of the small molecules can be summarized as follows: a core structure including at least two rings, which can be fused or unfused, wherein at least one of the rings contains a nitrogen atom and/or has a side chain that contains a nitrogen atom. Certain of the molecules are effective even without presence of a nitrogen atom.

It has been observed that fused three-ring structures such as quinacrine are typically an order of magnitude more potent as inhibitors of TLR-mediated immunostimulation than are fused two-ring structures such as chloroquine. For example, quinacrine is reported to have an $EC_{50}$ of about 8 nM, where $EC_{50}$ is the concentration required for half-maximal inhibition of CpG-ODN effect on thymidine uptake by WEHI 231 B-cells in the presence of anti-surface IgM. U.S. Pat. No. 6,479,504 B1. It has now also been discovered according to the present invention that fused two-ring core structures to which are attached a nitrogen-containing ring substituent can be as potent as fused three-ring structures such as quinacrine. In particular, such compounds can exhibit $EC_{50}$ in the low nanomolar range. In certain embodiments the nitrogen-containing ring substituent is a $C_2$-$C_6$ alkyl group terminated by a tertiary amine, such as methylethylamine, diethyl amine, dimethyl amine, or a ring containing at least one nitrogen.

Without meaning to be bound to any particular theory or mechanism, it is the belief of the instant inventors that both the ring-containing core structure and the side chain substituents contribute to affinity and efficacy. It is believed that molecules with high affinity core structure and low affinity substituents can be as effective as molecules with low affinity core structure and high affinity substituents.

Over many years there have been observations that certain common classes of drugs used for purposes other than affecting the immune system in fact have side effects that include immune suppression. For example, the phenothiazine chlorpromazine has been reported to inhibit messenger RNA expression for interleukin 2 (IL-2), tumor necrosis factor alpha (TNF-α), and gamma interferon (IFN-γ). Schleuning M J et al. (1989) *Eur J Immunol* 19:1491-6. In a separate study, chlorpromazine was reported to depress contact hypersensitivity to dinitrochlorobenzene in guinea-pigs. Descotes J et al. (1982) *J Neuroimmunol* 2:21-5. Yet another study reported that acute, high dose administration of the tricyclic antidepressant drug imipramine inhibits lipopolysaccharide (LPS)-induced increases in TNF-α but has little or no effect on LPS-induced interleukin 1 beta (IL-1β) or interleukin 10 (IL-10). Dredge K et al. (1999) *Int J Immunopharm* 21:663-73.

Histamine is a widely recognized mediator of immediate hypersensitivity and inflammation, which are principally mast cell- and basophil-mediated immune phenomena. The pleiotropic effects of histamine are mediated through three types of membrane-associated histamine receptor, histamine H1 receptor (H1R), histamine H2 receptor (H2R), and histamine H3 receptor (H3R). Pharmacologic inhibitors for these receptors are known and include pyrilamine and tripelennamine (H1R); cimetidine, famotidine, and ranitidine (H2R); and thioperamide and clobenpropit (H3R). Recently it was reported that signaling through H1R augments T-cell and B-cell antigen receptor-mediated responses. Banu Y et al. (1999)*J Exp Med* 189:673-82. T cells and B cells derived from H1R-deficient (H1R$^{-/-}$) mice were reported to have normal responses to LPS. Banu et al. also reported that administration of the H2R-specific antagonist famotidine further depressed T-cell and B-cell antigen receptor-mediated responses in H1R$^{-/-}$ mice. Jutel and coworkers recently reported that in their study of T cells, the Th1 subset of CD4+ T cells preferentially express H1R, while Th2 cells preferentially express H2R. They also reported that histamine enhances Th1-type responses by triggering H1R, and that H1R$^{-/-}$ mice have suppressed levels of the Th1 cytokine IFN-γ and increased levels of the Th2 cytokines IL-4 and IL-13. Jutel M et al. (2001) *Nature* 413:420-5.

In contrast, with respect to dendritic cells (DC), Mazzoni and others have reported that histamine inhibits IL-12 production and stimulates IL-10 secretion in LPS-stimulated monocyte-derived DC, resulting in a shift from a Th1- to a Th2-polarized immune response. Mazzoni A et al. (2001) *J Clin Invest* 108:1865; Caron G et al. (2001) *J Immunol* 166: 6000-6. Recently Mazzoni et al. also reported their observation that histamine, acting through H2R, inhibits release of type I IFN and TNF-α by plasmacytoid DC (pDC), the principal producers of IFN-α, in response to exposure to CpG ODN or live influenza virus. Mazzoni A et al. (2003) *J Immunol* 170:2269-73. Finally, it was recently reported that histamine, acting through H2R on monocyte/macrophages, suppresses NADPH oxidase, a key enzyme in oxygen radical formation, resulting in protection of natural killer (NK) cells and T cells against oxygen radical-induced dysfunction and apoptosis. Hellstrand K (2002) *Semin Oncol* 29(3 Suppl 7):35-40.

Definitions

Unless otherwise defined, all technical and scientific terms used herein have the same meaning as commonly understood by one of ordinary skill in the art to which this invention belongs.

As used herein, the term "adaptive immune response" refers to any type of antigen-specific immune response. Adaptive immune responses, which are also known in the art as specific immune responses, involve lymphocytes are also characterized by immunological memory, whereby response to a second or subsequent exposure to antigen is more vigorous than the response to a first exposure to the antigen. The term adaptive immune response encompasses both humoral (antibody) immunity and cell-mediated (cellular) immunity.

As used herein, "allergy" refers to acquired hypersensitivity to a substance (allergen). Allergic conditions include eczema, allergic rhinitis or coryza, hay fever, asthma, urticaria (hives) and food allergies, and other atopic conditions.

As used herein, the term "antigenic substance" refers to any substance that induces an adaptive (specific) immune response. An antigen typically is any substance that can be specifically bound by a T-cell antigen receptor, antibody, or B-cell antigen receptor. Antigenic substances include, without limitation, peptides, proteins, carbohydrates, lipids, phospholipids, nucleic acids, autacoids, and hormones. Antigenic substances further specifically include antigens that are classified as allergens, cancer antigens, and microbial antigens.

As used herein, "asthma" refers to a disorder of the respiratory system characterized by inflammation, narrowing of the airways and increased reactivity of the airways to inhaled agents. Asthma is frequently, although not exclusively associated with atopic or allergic symptoms. For example, asthma can be precipitated by exposure to an allergen, exposure to cold air, respiratory infection, and exertion.

As used herein, the terms "autoimmune disease" and, equivalently, "autoimmune disorder" and "autoimmunity", refer to immunologically mediated acute or chronic injury to a tissue or organ derived from the host. The terms encompass both cellular and antibody-mediated autoimmune phenomena, as well as organ-specific and organ-nonspecific autoimmunity. Autoimmune diseases include insulin-dependent diabetes mellitus, rheumatoid arthritis, systemic lupus erythematosus, multiple sclerosis, atherosclerosis, and inflammatory bowel disease. Autoimmune diseases also include, without limitation, ankylosing spondylitis, autoimmune hemolytic anemia, Behçet's syndrome, Goodpasture's syndrome, Graves' disease, Guillain-Bárre syndrome, Hashimoto's thyroiditis, idiopathic thrombocytopenia, myasthenia gravis, pernicious anemia, polyarteritis nodosa, polymyositis/dermatomyositis, primary biliary sclerosis, psoriasis, sarcoidosis, sclerosing cholangitis, Sjögren's syndrome, systemic sclerosis (scleroderma and CREST syndrome), Takayasu's arteritis, temporal arteritis, and Wegener's granulomatosis. Autoimmune diseases also include certain immune complex-associated diseases.

As used herein, the terms "cancer" and, equivalently, "tumor" refer to a condition in which abnormally replicating cells of host origin are present in a detectable amount in a subject. The cancer can be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric (stomach) cancer; intraepithelial neoplasms; leukemias; lymphomas; liver cancer; lung cancer (e.g., small cell and non-small cell); melanoma; neuroblastomas; oral cancer; ovarian cancer; pancreatic cancer; prostate cancer; rectal cancer; renal (kidney) cancer; sarcomas; skin cancer; testicular cancer; thyroid cancer; as well as other carcinomas and sarcomas. Cancers can be primary or metastatic.

As used herein, the term "CpG DNA" refers to an immunostimulatory nucleic acid which contains a cytosine-guanine (CG) dinucleotide, the C residue of which is unmethylated. The effects of CpG nucleic acids on immune modulation have been described extensively in U.S. patents such as U.S. Pat. Nos. 6,194,388; 6,207,646; 6,239,116; and 6,218,371, and published international patent applications, such as WO98/37919, WO98/40100, WO98/52581, and WO99/56755. The entire contents of each of these patents and published patent applications is hereby incorporated by reference. The entire immunostimulatory nucleic acid can be unmethylated or portions may be unmethylated but at least the C of the 5'-CG-3' must be unmethylated.

CpG DNA includes both naturally occurring immunostimulatory nucleic acids, as found in bacterial DNA and plasmids, as well as synthetic oligodeoxynucleotides (ODN).

In one embodiment the CpG DNA is a CpG ODN that has a base sequence provided by 5'-TCGTCGTTTTGTCGTTTTGTCGTT-3' (ODN 2006; SEQ ID NO:1).

CpG ODN have been further classified by structure and function into at least the following three classes or types, all of which are intended to be encompassed within the term CpG DNA as used herein: B-class CpG ODN such as ODN 2006 include the originally described immunostimulatory CpG ODN and characteristically activate B cells and NK cells but do not induce or only weakly induce expression of type I interferon (e.g., IFN-α). A-class CpG ODN, described in published PCT international application WO 01/22990, incorporate a CpG motif, include a chimeric phosphodiester/phosphorothioate backbone, and characteristically activate NK cells and induce plasmacytoid dendritic cells to express large amounts of IFN-α but do not activate or only weakly activate B cells. An example of an A-class CpG ODN is 5'-G*G*G_G_G_A_C_G_A_T_C_G_T_C_G*G*G*G*G-3' (ODN 2216, SEQ ID NO:2), wherein "*" represents phosphorothioate and "_" represents phosphodiester. C-class CpG ODN incorporate a CpG, include a wholly phosphorothioate backbone, include a GC-rich palindromic or nearly-palindromic region, and are capable of both activating B cells and inducing expression of IFN-α. C-class CpG ODN have been described, for example, in published U.S. patent application 2003/0148976. An example of a C-class CpG ODN is 5'-TCGTCGTTTTCGGCGCGCGCCG-3' (ODN 2395; SEQ ID NO:3). For a review of the various classes of CpG ODN, see also Vollmer J et al. (2004) *Eur J Immunol* 34:251-62.

As used herein, "cytokine" refers to any of a number of soluble proteins or glycoproteins that act on immune cells through specific receptors to affect the state of activation and function of the immune cells. Cytokines include interferons, interleukins, tumor necrosis factor, transforming growth factor beta, colony-stimulating factors (CSFs), chemokines, as well as others. Various cytokines affect innate immunity, acquired immunity, or both. Cytokines specifically include, without limitation, IFN-α, IFN-β, IFN-γ, IL-1, IL-2, IL-3, IL-4, IL-5, IL-6, IL-9, IL-10, IL-12, IL-13, IL-18, TNF-α, TGF-β, granulocyte colony-stimulating factor (G-CSF), and granulocyte-macrophage colony-stimulating factor (GM-CSF). Chemokines specifically include, without limitation, IL-8, IP-10, I-TAC, RANTES, MIP-1α, MIP-1β, Gro-α, Gro-β, Gro-γ, MCP-1, MCP-2, and MCP-3.

Most mature $CD4^+$ T helper cells can be categorized into one of two cytokine-associated, cross-regulatory subsets or phenotypes: Th1 or Th2. Th1 cells are associated with IL-2, IL-3, IFN, GM-CSF and high levels of TNF-α. Th2 cells are associated with IL-3, IL-4, IL-5, IL-6, IL-9, IL-10, IL-13, GM-CSF and low levels of TNF-α. The Th1 subset promotes both cell-mediated immunity and humoral immunity that is characterized by immunoglobulin class switching to IgG2a in mice. Th1 responses can also be associated with delayed-type hypersensitivity and autoimmune disease. The Th2 subset induces primarily humoral immunity and induces immunoglobulin class switching to IgE and IgG1 in mice. The antibody isotypes associated with Th1 responses generally have good neutralizing and opsonizing capabilities, whereas those associated with Th2 responses are associated more with allergic responses.

Several factors have been shown to influence commitment to Th1 or Th2 profiles. The best characterized regulators are cytokines. IL-12 and IFN-γ are positive Th1 and negative Th2 regulators. IL-12 promotes IFN-γ production, and IFN-γ provides positive feedback for IL-12. IL-4 and IL-10 appear to be required for the establishment of the Th2 cytokine profile and to down-regulate Th1 cytokine production; the effects of IL-4 are in some cases dominant over those of IL-12. IL-13 was shown to inhibit expression of inflammatory cytokines, including IL-12 and TNF-α by LPS-induced monocytes, in a way similar to IL-4.

As used herein, "effective amount" refers to any amount that is necessary or sufficient for achieving or promoting a desired outcome. In some instances an effective amount is a therapeutically effective amount. A therapeutically effective amount is any amount that is necessary or sufficient for promoting or achieving a desired biological response in a subject. The effective amount for any particular application can vary depending on such factors as the disease or condition being treated, the particular agent being administered, the size of the subject, or the severity of the disease or condition. One of ordinary skill in the art can empirically determine the effective amount of a particular agent without necessitating undue experimentation.

As used herein, "graft rejection" refers to immunologically mediated hyperacute, acute, or chronic injury to a tissue or organ derived from a source other than the host. The term thus encompasses both cellular and antibody-mediated rejection, as well as rejection of both allografts and xenografts.

As used herein, the term "immune cell" refers to a cell belonging to the immune system. Immune cells include T lymphocytes (T cells), B lymphocytes (B cells), natural killer (NK) cells, granulocytes, neutrophils, macrophages, monocytes, dendritic cells, and specialized forms of any of the foregoing, e.g., plasmacytoid dendritic cells, plasma cells, NKT, T helper, and cytotoxic T lymphocytes (CTL).

As used herein, the term "immune complex" refers to any conjugate including an antibody and an antigen specifically bound by the antibody. In one embodiment the antigen is an autoantigen.

As used herein, the term "immune complex comprising a nucleic acid" refers to any conjugate including an antibody and a nucleic acid-containing antigen specifically bound by the antibody. The nucleic acid-containing antigen can include chromatin, ribosomes, small nuclear proteins, histones, nucleosomes, DNA, RNA, or any combination thereof. The antibody can but need not necessarily bind specifically to a nucleic acid component of the nucleic acid-containing antigen.

As used herein, the term "immune complex-associated disease" refers to any disease characterized by the production and/or tissue deposition of immune complexes, including, but not limited to systemic lupus erythematosus (SLE) and related connective tissue diseases, rheumatoid arthritis, hepatitis C- and hepatitis B-related immune complex disease (e.g., cryoglobulinemia), Behçet's syndrome, autoimmune glomerulonephritides, and vasculopathy associated with the presence of LDL/anti-LDL immune complexes.

As used herein, "immunodeficiency" refers to a disease or disorder in which the subject's immune system is not functioning in normal capacity or in which it would be useful to boost a subject's immune response for example to eliminate a tumor or cancer (e.g., tumors of the brain, lung (e.g., small cell and non-small cell), ovary, breast, prostate, colon, as well as other carcinomas and sarcomas) or an infection in a subject. The immunodeficiency can be acquired or it can be congenital.

As used herein, "immunostimulatory nucleic acid-associated response in a subject" refers to a measurable response in a subject associated with administration to the subject of an immunostimulatory nucleic acid. Such responses include, without limitation, elaboration of cytokines, chemokines, growth factors, or immunoglobulin; expression of immune cell surface activation markers; Th1/Th2 skewing; and clinical disease activity.

As used herein, the terms "infection" and, equivalently, "infectious disease" refer to a condition in which an infectious organism or agent is present in a detectable amount in the blood or in a normally sterile tissue or normally sterile compartment of a subject. Infectious organisms and agents include viruses, bacteria, fungi, and parasites. The terms encompass both acute and chronic infections, as well as sepsis.

As used herein, the term "innate immune response" refers to any type of immune response to certain pathogen-associated molecular patterns (PAMPs). Innate immunity, which is also known in the art as natural or native immunity, involves principally neutrophils, granulocytes, mononuclear phagocytes, dendritic cells, NKT cells, and NK cells. Innate immune responses can include, without limitation, type I interferon production (e.g., IFN-α), neutrophil activation, macrophage activation, phagocytosis, opsonization, complement activation, and any combination thereof.

As used herein, the term "self-DNA" refers to any DNA derived from the genome of a host subject. In one embodiment self-DNA includes complementary DNA (cDNA) derived from a host subject. Self-DNA includes intact and degraded DNA.

As used herein, the term "self-RNA" refers to any RNA derived from the genome of a host subject. In one embodiment self-RNA is a messenger RNA (mRNA) derived from a host subject. In one embodiment self-RNA includes ribosomal RNA (rRNA) derived from a host subject. Self-RNA includes intact and degraded RNA.

As used herein, the term "subject" refers to a vertebrate animal. In one embodiment the subject is a mammal. In one embodiment the subject is a human. In other embodiments the subject is a non-human vertebrate animal, including, without limitation, non-human primates, laboratory animals, livestock, domesticated animals, and non-domesticated animals.

As used herein, "subject having or at risk of developing TLR-mediated immunostimulation" refers to a subject exposed to or at risk of exposure to a PAMP or other TLR ligand.

As used herein, the terms "Toll-like receptor" and, equivalently, "TLR" refer to any member of a family of at least ten highly conserved mammalian pattern recognition receptor proteins (TLR1-TLR10) which recognize pathogen-associated molecular patterns (PAMPs) and act as key signaling elements in innate immunity. TLR polypeptides share a characteristic structure that includes an extracellular (extracytoplasmic) domain that has leucine-rich repeats, a transmembrane domain, and an intracellular (cytoplasmic) domain that is involved in TLR signaling. TLRs include but are not limited to human TLRs.

Nucleic acid and amino acid sequences for all ten currently known human TLRs are available from public databases such as GenBank. Similarly, nucleic acid and amino acid sequences for various TLRs from numerous non-human species are also available from public databases including GenBank. For example, nucleic acid and amino acid sequences for human TLR9 (hTLR9) can be found as GenBank accession numbers AF245704 (coding region spanning nucleotides 145-3243) and AAF78037, respectively. Nucleic acid and amino acid sequences for murine TLR9 (mTLR9) can be found as GenBank accession numbers AF348140 (coding region spanning nucleotides 40-3138) and AAK29625, respectively. The deduced human TLR9 protein contains 1,032 amino acids and shares an overall amino acid identity of 75.5% with mouse TLR9. Like other TLR proteins, human TLR9 contains extracellular leucine-rich repeats (LRRs) and a cytoplasmic Toll/interleukin-1R (TIR) domain. It also has a signal peptide (residues 1-25) and a transmembrane domain (residues 819-836).

Nucleic acid and amino acid sequences for human TLR8 (hTLR8) can be found as GenBank accession numbers AF245703 (coding region spanning nucleotides 49-3174) and AAF78036, respectively. Nucleic acid and amino acid sequences for murine TLR8 (mTLR8) can be found as GenBank accession numbers AY035890 (coding region spanning nucleotides 59-3157) and AAK62677, respectively.

Nucleic acid and amino acid sequences for human TLR7 (hTLR7) can be found as GenBank accession numbers AF240467 (coding region spanning nucleotides 135-3285) and AAF60188, respectively. Nucleic acid and amino acid sequences for murine TLR7 (mTLR7) can be found as GenBank accession numbers AY035889 (coding region spanning nucleotides 49-3201) and AAK62676, respectively.

Nucleic acid and amino acid sequences for human TLR3 (hTLR3) can be found as GenBank accession numbers NM_003265 (coding region spanning nucleotides 102-2816) and NP_003256, respectively. Nucleic acid and amino acid sequences for murine TLR3 (hTLR3) can be found as GenBank accession numbers AF355152 (coding region spanning nucleotides 44-2761) and AAK26117, respectively.

While hTLR1 is ubiquitously expressed, hTLR2, hTLR4 and hTLR5 are present in monocytes, polymorphonuclear phagocytes, and dendritic cells. Muzio M et al. (2000) *J Leukoc Biol* 67:450-6. Recent publications reported that hTLR1, hTLR6, hTLR7, hTLR9 and hTLR10 are present in human B cells. Human TLR7 and hTLR9 are present in plasmacytoid dendritic cells (pDCs), while myeloid dendritic cells express hTLR7 and hTLR8 but not hTLR9. Human TLR8, however, appears not to be expressed in pDCs.

As members of the pro-inflammatory interleukin-1 receptor (IL-1R) family, TLRs share homologies in their cytoplasmic domains called Toll/IL-1R homology (TIR) domains. PCT published applications PCT/US98/08979 and PCT/US01/16766. Intracellular signaling mechanisms mediated by TLRs appear generally similar, with MyD88 and tumor necrosis factor receptor-associated factor 6 (TRAF6) believed to have critical roles. Wesche H et al. (1997) *Immunity* 7:837-47; Medzhitov R et al. (1998) *Mol Cell* 2:253-8; Adachi 0 et al. (1998) *Immunity* 9:143-50; Kawai Tet al. (1999) *Immunity* 11:115-22); Cao Z et al. (1996) *Nature* 383:443-6; Lomaga M A et al. (1999) *Genes Dev* 13:1015-24. Signal transduction between MyD88 and TRAF6 is known to involve members of the serine-threonine kinase IL-1 receptor-associated kinase (IRAK) family, including at least IRAK-1 and IRAK-2. Muzio M et al. (1997) *Science* 278: 1612-5.

Briefly, MyD88 is believed to act as an adapter molecule between the TIR domain of a TLR or IL-1R and IRAK (which includes at least any one of IRAK-1, IRAK-2, IRAK-4, and IRAK-M). MyD88 includes a C-terminal Toll homology domain and an N-terminal death domain. The Toll homology domain of MyD88 binds the TIR domain of TLR or IL-1R, and the death domain of MyD88 binds the death domain of the serine kinase IRAK. IRAK interacts with TRAF6, which acts as an entryway into at least two pathways, one leading to activation of the transcription factor NF-κB and another leading to activation of Jun and Fos, members of the activator protein-1 (AP-1) transcription factor family. Activation of NF-κB involves the activation of TAK-1, a member of the MAP 3 kinase (MAPK) family, and IκB kinases. The IκB kinases phosphorylate IκB, leading to its degradation and the translocation of NF-κB to the nucleus. Activation of Jun and Fos is believed to involve MAP kinase kinases (MAPKKs) and MAP kinases ERK, p38, and JNK/SAPK. Both NF-κB and AP-1 are involved in controlling the transcription of a number of key immune response genes, including genes for various cytokines and costimulatory molecules. See Aderem A et al. (2000) *Nature* 406:782-7; Häcker H et al. (1999) *EMBO J.* 18:6973-82.

As used herein, the terms "TLR ligand" and, equivalently, "ligand for a TLR" and "TLR signaling agonist", refer to a molecule, other than a small molecule according to Formula I-XIX described herein or a 4-primary amino quinoline or quinazoline molecule according to the invention, that interacts, directly or indirectly, with a TLR through a TLR domain other than a TIR domain and induces TLR-mediated signaling. In one embodiment a TLR ligand is a natural ligand, i.e., a TLR ligand that is found in nature. In one embodiment a TLR ligand refers to a molecule other than a natural ligand of a TLR, e.g., a molecule prepared by human activity. In one embodiment the TLR is TLR9 and the TLR signal agonist is a CpG nucleic acid.

Ligands for many but not all of the TLRs have been described. For instance, it has been reported that TLR2 signals in response to peptidoglycan and lipopeptides. Yoshimura A et al. (1999) *J Immunol* 163:1-5; Brightbill H D et al. (1999) *Science* 285:732-6; Aliprantis A O et al. (1999) *Science* 285:736-9; Takeuchi 0 et al. (1999) *Immunity* 11:443-51; Underhill D M et al. (1999) *Nature* 401:811-5. TLR4 has been reported to signal in response to lipopolysaccharide (LPS). Hoshino K et al. (1999) *J Immunol* 162:3749-52; Poltorak A et al. (1998) *Science* 282:2085-8; Medzhitov R et al. (1997) *Nature* 388:394-7. Bacterial flagellin has been reported to be a natural ligand for TLR5. Hayashi F et al. (2001) *Nature* 410:1099-1103. TLR6, in conjunction with TLR2, has been reported to signal in response to proteoglycan. Ozinsky A et al. (2000) *Proc Natl Acad Sci USA* 97:13766-71; Takeuchi O et al. (2001) *Int Immunol* 13:933-40.

Recently it was reported that TLR9 is a receptor for CpG DNA. Hemmi H et al. (2000) *Nature* 408:740-5; Bauer S et al. (2001) *Proc Natl Acad Sci USA* 98:9237-42. CpG DNA, which includes bacterial DNA and synthetic DNA with CG dinucleotides in which cytosine is unmethylated, is described in greater detail elsewhere herein. Marshak-Rothstein and colleagues also recently reported their finding that TLR9 signaling can occur in certain autoimmune diseases in response to immune complexes containing IgG and chromatin. Leadbetter E A et al. (2002) *Nature* 416:595-8. Thus, in a broader sense it appears that TLR9 can signal in response to self or non-self nucleic acid, either DNA or RNA, when the nucleic acid is presented in a suitable context, e.g., as part of an immune complex.

Recently it was reported that certain imidazoquinoline compounds having antiviral activity are ligands of TLR7 and TLR8. Hemmi H et al. (2002) *Nat Immunol* 3:196-200; Jurk M et al. (2002) *Nat Immunol* 3:499. Imidazoquinolines are potent synthetic activators of immune cells with antiviral and antitumor properties. Using macrophages from wildtype and MyD88-deficient mice, Hemmi et al. recently reported that two imidazoquinolines, imiquimod and resiquimod (R848), induce tumor necrosis factor (TNF) and interleukin-12 (IL-12) and activate NF-κB only in wildtype cells, consistent with activation through a TLR. Hemmi H et al. (2002) *Nat Immunol* 3:196-200. Macrophages from mice deficient in TLR7 but not other TLRs produced no detectable cytokines in response to these imidazoquinolines. In addition, the imidazoquinolines induced dose-dependent proliferation of splenic B cells and the activation of intracellular signaling cascades in cells from wildtype but not TLR7-/- mice. Luciferase analysis established that expression of human TLR7, but not TLR2 or TLR4, in human embryonic kidney cells results in NF-κB activation in response to resiquimod. The findings of Hemmi et al. thus suggested that these imidazoquinoline compounds are non-natural ligands of TLR7 that can induce signaling through TLR7.

Recently it was reported that R848 is also a ligand for human TLR8. Jurk M et al. (2002) *Nat Immunol* 3:499.

It was recently reported that ligands of TLR3 include poly (I:C) and double-stranded RNA (dsRNA). For purposes of this invention, poly(I:C) and double-stranded RNA (dsRNA) are classified as oligonucleotide molecules. By stimulating kidney cells expressing one of a range of TLRs with poly(I:C), Alexopoulou et al. reported that only cells expressing TLR3 respond by activating NF-κB. Alexopoulou L et al. (2001) *Nature* 413: 732-8. Alexopoulou et al. also reported that wildtype cells stimulated with poly(I:C) activate NF-κB and produce inflammatory cytokines IL-6, IL-12, and TNF-α, whereas the corresponding responses of TLR3$^{-/-}$ cells were significantly impaired. In contrast, TLR3$^{-/-}$ cells responded equivalently to wildtype cells in response to lipopolysaccharide, peptidoglycan, and CpG dinucleotides. Analysis of MyD88$^{-/-}$ cells indicated that this adaptor protein is involved in dsRNA-induced production of cytokines and proliferative responses, although activation of NF-κB and MAP kinases are not affected, indicating distinct pathways for these cellular responses. Alexopoulou et al. proposed that TLR3 may have a role in host defense against viruses.

As used herein, a "cell expressing a TLR" refers to any cell which expresses, either naturally or artificially, a functional TLR. A functional TLR is a full-length TLR protein or a fragment thereof capable of inducing a signal in response to interaction with its ligand. Generally the functional TLR will include at least a TLR ligand-binding fragment of the extracellular domain of the full-length TLR and at least a fragment of a TIR domain capable of interacting with another Toll homology domain-containing polypeptide, e.g., MyD88. In various embodiments the functional TLR is a full-length TLR selected from TLR1, TLR2, TLR3, TLR4, TLR5, TLR6, TLR7, TLR8, TLR9, and TLR10.

In certain embodiments the functional TLR is naturally expressed by a cell.

In one embodiment the cell naturally expresses functional TLR and is an isolated cell from human multiple myeloma cell line RPMI 8226 (ATCC CCL-155). This cell line was established from the peripheral blood of a 61 year old man at the time of diagnosis of multiple myeloma (IgG lambda type). Matsuoka Y et al. (1967) *Proc Soc Exp Biol Med* 125:1246-50. RPMI 8226 was previously reported as responsive to CpG nucleic acids as evidenced by the induction of IL-6 protein and IL-12p40 mRNA. Takeshita F et al. (2000) *Eur J Immunol* 30:108-16; Takeshita F et al. (2000) *Eur J Immunol* 30:1967-76. Takeshita et al. used the cell line solely to study promoter constructs in order to identify transcription factor binding sites important for CpG nucleic acid signaling. It is now known that RPMI 8226 cells secrete a number of other chemokines and cytokines including IL-8, IL-10 and IP-10 in response to immunostimulatory nucleic acids. Because this cell line expresses TLR9, through which immunostimulatory nucleic acids such as for example CpG nucleic acids mediate their effects, it is a suitable cell line for use in the methods of the invention relating to CpG nucleic acids as reference and test compounds, as well as to other TLR9 ligands.

Similar to peripheral blood mononuclear cells (PBMCs), the RPMI 8226 cell line has been observed to upregulate its cell surface expression of markers such as CD71, CD86 and HLA-DR in response to CpG nucleic acid exposure. This has been observed by flow cytometric analysis of the cell line. Accordingly, the methods provided herein can be structured to use appropriately selected cell surface marker expression as a readout, in addition to or in place of chemokine or cytokine production or other readouts described elsewhere herein.

The RPMI 8226 cell line has also been found to respond to certain small molecules including imidazoquinoline compounds. For example, incubation of RPMI 8226 cells with the imidazoquinoline compound R848 (resiquimod) induces IL-8, IL-10, and IP-10 production. It has recently been reported that R848 mediates its immunostimulatory effects through TLR7 and TLR8. The ability of RPMI 8226 to respond to R848 suggests that the RPMI 8226 cell line also expresses TLR7, as previously reported for normal human B cells.

The RPMI cell line can be used in unmodified form or in a modified form. In one embodiment, the RPMI 8226 cell is transfected with a reporter construct. Preferably, the cell is stably transfected with the reporter construct. The reporter construct generally includes a promoter, a coding sequence and a polyadenylation signal. The coding sequence can include a reporter sequence selected from the group consisting of an enzyme (e.g., luciferase, alkaline phosphatase, beta-galactosidase, chloramphenicol acetyltransferase (CAT), secreted alkaline phosphatase, etc.), a bioluminescence marker (e.g., green fluorescent protein (GFP, U.S. Pat. No. 5,491,084), etc.), a surface-expressed molecule (e.g., CD25), a secreted molecule (e.g., IL-8, IL-12 p40, TNF-α, etc.), and other detectable protein products known to those of skill in the art. Preferably, the coding sequence encodes a protein having a level or an activity that is quantifiable.

In certain embodiments the functional TLR is artificially expressed (including over-expressed) by a cell, for example by introduction into the cell of an expression vector bearing a coding sequence for the functional TLR wherein the coding sequence is operably linked to a gene expression sequence. As used herein, a coding sequence and the gene expression sequence are said to be operably linked when they are covalently linked in such a way as to place the expression or transcription and/or translation of the coding sequence under the influence or control of the gene expression sequence. Two DNA sequences are said to be operably linked if induction of a promoter in the 5' gene expression sequence results in the transcription of the coding sequence and if the nature of the linkage between the two DNA sequences does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a gene expression sequence would be operably linked to a coding sequence if the gene expression sequence were capable of effecting transcription of that coding sequence such that the resulting transcript is translated into the desired protein or polypeptide.

In some embodiments a coding sequence refers to a nucleic acid sequence coding for a functional TLR. In some embodiments a coding sequence refers to a nucleic acid sequence coding for a reporter.

A cell that artificially expresses a functional TLR can be a cell that does not express the functional TLR but for the TLR expression vector. For example, human 293 fibroblasts (ATCC CRL-1573) do not express TLR3, TLR7, TLR8, or TLR9. As described in the examples below, such cells can be transiently or stably transfected with suitable expression vector (or vectors) so as to yield cells that do express TLR3, TLR7, TLR8, TLR9, or any combination thereof. Alternatively, a cell that artificially expresses a functional TLR can be a cell that expresses the functional TLR at a significantly higher level with the TLR expression vector than it does without the TLR expression vector.

For use in the methods of the instant invention, a cell that artificially expresses a functional TLR is preferably a stably transfected cell that expresses the functional TLR. Such a cell can also be stably transfected with a suitable reporter construct.

As used herein, "TLR-mediated signaling" refers to any portion of the intracellular signal transduction pathway involving interaction of a TLR with a suitable TLR ligand and engagement by the TLR of MyD88 or any aspect downstream of MyD88 engagement, described above in relation to the structure and function of the TIR domain of a TLR.

As used herein, "TLR-mediated immunostimulatory signaling" refers to TLR-mediated signaling that results in a measurable immunostimulatory response. This term applies to such signaling both in vitro and in vivo.

As used herein, "TLR-mediated immunostimulation in a subject" refers to TLR-mediated immunostimulatory signaling as it applies in vivo.

As used herein, the term "treat" as used in reference to a disorder, disease, or condition means to intervene in such disorder, disease, or condition so as to prevent or slow the development of, to prevent, slow or halt the progression of, or to eliminate the disorder, disease, or condition.

Immunostimulatory Nucleic Acids

As used herein, "immunostimulatory nucleic acid" refers to a nucleic acid molecule that, when contacted with a cell of the immune system, induces the cell of the immune system to become activated. Immune cell activation can be determined using any suitable means known to one of skill in the art, including but not limited to measurement of stimulated growth, proliferation, differentiation, migration, transcription or expression of gene products that are expressed or secreted in association with immune activation, activity of intracellular signaling pathways, and the like. Examples of markers of immune cell activation include, without limitation, secretion of cytokines (e.g., IL-6), secretion of immunoglobulin (e.g., IgG), expression of cell surface antigens (e.g., CD86), induction of cytolytic activity, and induction and nuclear translocation of transcription factors (e.g., NF-κB).

A "nucleic acid" as used herein with respect to the methods of the invention, shall refer to any polymer of two or more individual nucleoside or nucleotide units. Nucleic acids can be single- or double-stranded. Typically individual nucleoside or nucleotide units will include any one or combination of deoxyribonucleosides, ribonucleosides, deoxyribonucleotides, and ribonucleotides. The individual nucleotide or nucleoside units of the nucleic acid can be naturally occurring or not naturally occurring. For example, the individual nucleotide units can include deoxyadenosine, deoxycytidine, deoxyguanosine, thymidine, and uracil. In addition to naturally occurring 2'-deoxy and 2'-hydroxyl forms, individual nucleosides also include synthetic nucleosides having modified base moieties and/or modified sugar moieties, e.g., as described in Uhlmann E et al. (1990) Chem Rev 90:543-84. The linkages between individual nucleotide or nucleoside units can be naturally occurring or not naturally occurring. For example, the linkages can be phosphodiester, phosphorothioate, phosphorodithioate, phosphoramidate, as well as peptide linkages and other covalent linkages, known in the art, suitable for joining adjacent nucleoside or nucleotide units. Immunostimulatory nucleic acids typically range in size from 3-4 units to a few tens of units, e.g., 18-40 units, although longer nucleic acids are also contemplated by the invention.

In some embodiments the nucleic acids are oligonucleotides made up of 2 to about 100 nucleotides, and more typically 4 to about 40 nucleotides. Oligonucleotides composed exclusively of deoxyribonucleotides are termed oligodeoriboxynucleotides or, equivalently, oligodeoxynucleotides (ODN).

An immunostimulatory nucleic acid includes any of a number of different types of immunostimulatory nucleic acids, including specifically immunostimulatory CpG nucleic acids (CpG nucleic acids), including but not limited to types A, B, and C; and immunostimulatory non-CpG nucleic acids, including without limitation methylated CpG nucleic acids, T-rich nucleic acids, and poly-G nucleic acids. Certain of these various classes of immunostimulatory nucleic acids can coexist in a given nucleic acid molecule.

As used herein, the terms "CpG nucleic acid" and, equivalently, "CpG ODN" refer to an immunostimulatory nucleic acid which contains a cytosine-guanine (CG) dinucleotide, the C residue of which is unmethylated. The effects of CpG nucleic acids on immune modulation have been described extensively in U.S. patents such as U.S. Pat. Nos. 6,194,388; 6,207,646; 6,218,371; and 6,239,116, and published international patent applications, such as WO 98/37919, WO 98/40100, WO 98/52581, and WO 99/56755. The entire contents of each of these patents and published patent applications is hereby incorporated by reference. The entire immunostimulatory nucleic acid can be unmethylated or portions may be unmethylated but at least the C of the 5'-CG-3' must be unmethylated. The CpG nucleic acid sequences of the invention include those broadly described above as well as disclosed in U.S. Pat. Nos. 6,207,646 B1 and 6,239,116 B1.

In one embodiment the CpG nucleic acid has a base sequence provided by 5'-TCGTCGTTTTGTCGTTTTGTCGTT-3' (ODN 2006; SEQ ID NO:1).

CpG nucleic acids have been further classified by structure and function into at least the following three types, all of which are intended to be encompassed within the methods of the instant invention: Type B CpG nucleic acids such as ODN 2006 include the earliest described CpG nucleic acids and characteristically activate B cells but do not induce or only weakly induce expression of IFN-α. Type A CpG nucleic acids, described in published international application PCT/US00/26527 (WO 01/22990), incorporate a CpG motif, include a hybrid phosphodiester/phosphorothioate backbone, and characteristically induce plasmacytoid dendritic cells to express large amounts of IFN-α but do not activate or only weakly activate B cells. Type C oligonucleotides incorporate a CpG, include a chimeric backbone, include a GC-rich palindromic or nearly-palindromic region, and are capable of both activating B cells and inducing expression of IFN-α. These have been described, for example, in published U.S. patent application 2003/0148976.

In other embodiments of the invention, a non-CpG nucleic acid is used. A non-CpG nucleic acid is an immunostimulatory nucleic acid which either does not have a CpG motif in its sequence, or has a CpG motif which contains a methylated C residue. In some instances, the non-CpG nucleic acid may still be immunostimulatory by virtue of its having other immunostimulatory motifs such as those described herein and known in the art. In one embodiment the non-CpG nucleic acid is a methylated CpG nucleic acid. In some instances the non-CpG nucleic acid is still immunostimulatory despite methylation of the C of the CpG motif, even without having another non-CpG immunostimulatory motif described herein and known in the art.

In one embodiment the non-CpG nucleic acid is a methylated CpG nucleic acid having a base sequence provided by 5'-TZGTZGTTTTGTZGTTTTGTZGTT-3' (ODN 2117; SEQ ID NO:4, wherein Z represents 5-methylcytidine).

Non-CpG nucleic acids include T-rich immunostimulatory nucleic acids. The T-rich immunostimulatory nucleic acids include those disclosed in published PCT patent application PCT/US00/26383, the entire contents of which are incorporated herein by reference. In some embodiments, T-rich nucleic acids 24 bases in length are used. A T-rich nucleic acid is a nucleic acid which includes at least one poly T sequence and/or which has a nucleotide composition of greater than 25% T nucleotide residues. A nucleic acid having a poly-T sequence includes at least four Ts in a row, such as 5'-TTTT-3'. In some embodiments the T-rich nucleic acid includes more than one poly T sequence. In important embodiments, the T-rich nucleic acid may have 2, 3, 4, or more poly T sequences, such as ODN 2006.

Non-CpG nucleic acids also include poly-G immunostimulatory nucleic acids. A variety of references describe the immunostimulatory properties of poly-G nucleic acids. Pisetsky D S et al. (1993) Mol Biol Reports 18:217-221; Krieger M et al. (1994) Ann Rev Biochem 63:601-637; Macaya R F et al. (1993) Proc Natl Acad Sci USA 90:3745-3749; Wyatt J R et al. (1994) Proc Natl Acad Sci USA 91:1356-1360; Rando and Hogan, 1998, In Applied Antisense Oligonucleotide Technology, Krieg and Stein, eds., pp. 335-352; Kimura Y et al. (1994) J Biochem (Tokyo) 116:991-994.

The immunostimulatory nucleic acids of the invention can also be those which do not possess CpG, methylated CpG, T-rich, or poly-G motifs.

Exemplary immunostimulatory nucleic acid sequences further include but are not limited to those immunostimulatory sequences described and listed in published PCT patent application WO 01/22972.

In one aspect the invention provides novel compounds that fall within Formula VI and Formula VII as disclosed herein. These compounds include various diarylmethane TLR9 antagonists denoted herein as CMZ 203-84, CMZ 203-85, CMZ 203-88, CMZ 203-88-1, CMZ 203-89, and CMZ 203-91. Syntheses for each of these compounds are provided in Examples 12-17, respectively.

Similar to other compounds of Formula VI and Formula VII, these specific compounds were tested in vitro and found to inhibit TLR9 signaling. See Example 18. Thus compounds CMZ 203-84, CMZ 203-85, CMZ 203-88, CMZ 203-88-1, CMZ 203-89, and CMZ 203-91 are believed to be useful in the methods of the invention. More specifically, in one aspect the invention provides a method of affecting TLR-mediated signaling in response to a TLR ligand. The method includes the step of contacting a cell expressing a TLR with an effective amount of any one or combination of compounds CMZ 203-84, CMZ 203-85, CMZ 203-88, CMZ 203-88-1, CMZ 203-89, and CMZ 203-91, to inhibit or promote TLR-mediated signaling in response to a ligand for the TLR. In one aspect the the invention provides a method of inhibiting TLR-mediated signaling in response to a TLR ligand. The method includes the step of contacting a cell expressing a TLR with an effective amount of any one or combination of compounds CMZ 203-84, CMZ 203-85, CMZ 203-88, CMZ 203-88-1, CMZ 203-89, and CMZ 203-91, to inhibit TLR-mediated immunostimulatory signaling in response to a ligand for the TLR. In one aspect the invention provides a method of affecting TLR-mediated immunostimulation in a subject. The method includes the step of administering to a subject having or at risk of developing TLR-mediated immunostimulation an effective amount of any one or combination of compounds CMZ 203-84, CMZ 203-85, CMZ 203-88, CMZ 203-88-1, CMZ 203-89, and CMZ 203-91, to inhibit or promote TLR-mediated immunostimulation in the subject. In one aspect the invention provides a method of inhibiting TLR-mediated immunostimulation in a subject. The method includes the step of administering to a subject having or at risk of developing TLR-mediated immunostimulation an effective amount of any one or combination of compounds CMZ 203-84, CMZ 203-85, CMZ 203-88, CMZ 203-88-1, CMZ 203-89, and CMZ 203-91, to inhibit TLR-mediated immunostimulation in the subject. In one aspect the invention provides a method of inhibiting an immunostimulatory nucleic acid-associated response in a subject. The method according to this aspect includes the step of administering to a subject in need of such treatment an effective amount of any one or combination of compounds CMZ 203-84, CMZ 203-85, CMZ 203-88, CMZ 203-88-1, CMZ 203-89, and CMZ 203-91, to inhibit an immunostimulatory nucleic acid-associated response in the subject.

In one aspect the invention provides novel substituted 4-primary amino quinoline compositions. As described further below, these compositions and other substituted 4-primary amino quinoline compositions have been discovered to be useful in methods for inhibiting an immune response, both in vitro and in vivo, including methods for treating immune complex associated diseases and autoimmune disorders. Due to their similarity to certain known antimalarial agents, it is also believed that the novel substituted 4-primary amino quinoline compositions of the invention will also be useful for prevention and treatment of malaria, as well as for treatment of other diseases which have been described to be responsive to treatment with chloroquines.

The novel substituted 4-primary amino quinoline compositions of the invention have a structural Formula XVI

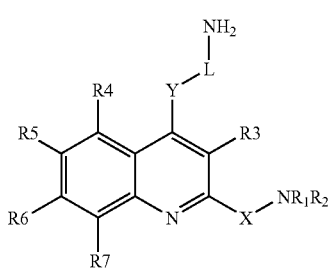

Formula XVI wherein
X is absent or is an aryl, alkyl, heterocyclic, or styryl group;
$R_1$ and $R_2$ are each independently a hydrogen atom or a substituted or unsubstituted alkyl, alkenyl, or aryl group, wherein $R_1$ and $R_2$ optionally are combined to form a heterocycle;
$R_3$ is a hydrogen atom, a halogen atom, or an alkyl, alkenyl, aryl, heterocyclic, nitro, cyano, carboxy, ester, ketone, amino, amido, hydroxy, alkoxy, mercapto, thio, sulfoxide, sulfone, or sulfonamido group, wherein $R_1$ and $R_3$ optionally are combined to form a heterocycle or a carbocycle;
Y is absent or is an oxygen atom, a sulfur atom, $CR_8R_9$, or $NR_{10}$, where $R_8$, $R_9$, and $R_{10}$ are each independently a hydrogen atom or a substituted or unsubstituted alkyl, alkenyl, or aryl group;
L is an alkyl or alkenyl group containing from 1 to 10 carbons or is an aryl group; and
$R_4$, $R_5$, $R_6$, and $R_7$ are each independently a hydrogen atom, a halogen atom, or an alkyl, alkenyl, aryl, heterocyclic, nitro, cyano, carboxy, ester, ketone, amino, amido, hydroxy, alkoxy, mercapto, thio, sulfoxide, sulfone, or sulfonamido group, wherein any pair of $R_4$, $R_5$, $R_6$, and $R_7$ which are adjacent one another optionally are combined to form a heterocycle or a carbocycle,
and pharmaceutically acceptable hydrates and salts thereof.

In one embodiment $R_5$ and $R_6$ are each independently a halogen atom or an alkoxy group. In one embodiment $R_5$ and $R_6$ are each independently a chlorine atom or a methoxy group.

In one embodiment X is absent or is an aryl group;
$NR_1R_2$ is a heterocyclic amine or is $NR_8(CH_2)_nNR_9R_{10}$, wherein n is an integer from 2 to 6, inclusive, and $R_8$, $R_9$, and $R_{10}$ are each independently a hydrogen atom or an alkyl group;
$R_3$ is a hydrogen atom;
Y is an aryl group or is $NR_{11}$ where $R_{11}$ is a hydrogen atom or an aryl or alkyl group;
L is absent or is a $C_2$-$C_6$ alkyl group; and
$R_4$, $R_5$, $R_6$, and $R_7$ are each independently a hydrogen atom, a halogen atom, or an alkoxy group.

In one embodiment X is absent or is an aryl group;
$NR_1R_2$ is a substituted or unsubstituted piperazino or morpholino group or is $NR_8(CH_2)_nNR_9R_{10}$, wherein n is an integer from 2 to 6, inclusive, $R_8$ is a hydrogen atom, and $R_9$ and $R_{10}$ are each independently an alkyl group;
$R_3$ is a hydrogen atom;
Y is NH;
L is a $C_2$-$C_6$ alkyl group; and
$R_4$, $R_5$, P6, and $R_7$ are each independently a hydrogen atom, a halogen atom, or an alkoxy group.

In one embodiment X is a phenyl group;
$NR_1R_2$ is

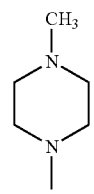

attached to a para position of the phenyl group X;
Y is NH;
L is —$(CH_2)_n$— where n is an integer between 2 and 6, inclusive; and
each of $R_3$, $R_4$, $R_5$, $R_6$, and $R_7$ is a hydrogen atom.

In each of the foregoing embodiments, the composition is optionally in the form of a pharmaceutically acceptable hydrate or salt.

Representative, non-limiting examples of substituted 4-primary amino quinoline compositions of Formula XVI of the invention are compounds 101-104, 106-109, 111, 113-116, and 118-119, presented in Table 1.

TABLE 1

Substituted 4-Primary Amino Quinoline Compositions of the Invention

| ID | X | NR₁R₂ | Y | L | R₃ | R₄ | R₅ | R₆ | R₇ |
|---|---|---|---|---|---|---|---|---|---|
| 101 | 1,4-dimethylphenyl | 4-methylpiperazin-1-yl (N-CH₃) | NH | —(CH₂)₂— | H | H | H | H | H |
| 102 | 1,4-dimethylphenyl | 4-methylpiperazin-1-yl (N-CH₃) | NH | —(CH₂)₃— | H | H | H | H | H |
| 103 | 1,3-dimethylphenyl | 4-methylpiperazin-1-yl (N-CH₃) | NH | —(CH₂)₂— | H | H | H | H | H |
| 104 | 1,4-dimethylphenyl | 4-methylpiperazin-1-yl (N-CH₃) | NH | —(CH₂)₄— | H | H | H | H | H |
| 106 | 1,4-dimethylphenyl | 4-methylpiperazin-1-yl (N-CH₃) | NH | —(CH₂)₅— | H | H | H | H | H |
| 107 | 1,4-dimethylphenyl | 4-methylpiperazin-1-yl (N-CH₃) | NH | —(CH₂)₂— | H | H | Cl | H | H |
| 108 | 4-methylbenzyl-NR₁R₂ | 4-methylpiperazin-1-yl (N-CH₃) | NH | —(CH₂)₃— | H | H | H | H | H |
| 109 | 1,4-dimethylphenyl | 4-methylpiperazin-1-yl (N-CH₃) | NH | —(CH₂)₆— | H | H | H | H | H |
| 111 | 1,2-dimethylphenyl | 4-methylpiperazin-1-yl (N-CH₃) | NH | —(CH₂)₃— | H | H | H | H | H |
| 113 | 1,2-dimethylphenyl | 1-methylpiperidinyl | NH | —(CH₂)₂— | H | H | H | H | H |
| 114 | 1,2-dimethylphenyl | N(CH₃)CH₂CH₂N(CH₃)₂ (NH) | NH | —(CH₂)₃— | H | H | H | H | H |
| 115 | 1,2-dimethylphenyl | N(CH₃)CH₂CH₂N(CH₃)₂ (NH) | NH | —(CH₂)₄— | H | H | H | H | H |
| 116 | 1,2-dimethylphenyl | N(CH₃)CH₂CH₂N(CH₃)₂ (NH) | NH | —(CH₂)₂— | H | H | H | H | H |

TABLE 1-continued

Substituted 4-Primary Amino Quinoline Compositions of the Invention

| ID | X | NR₁R₂ | Y | L | R₃ | R₄ | R₅ | R₆ | R₇ |
|----|---|-------|---|---|----|----|----|----|----|
| 118 | 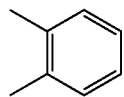 | 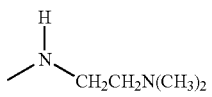 | NH | —(CH₂)₃— | H | H | H | H | H |
| 119 | 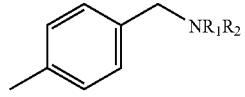 | 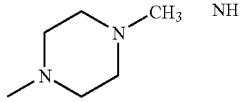 | NH | —(CH₂)₂— | H | H | H | H | H |

It has been discovered according to the invention that 4-primary amino quinoline compositions, similar to 4-secondary and 4-tertiary amino quinoline compounds, can be used to inhibit TLR9 signaling.

In one aspect the invention provides a method for inhibiting signaling by a TLR. The method according to this aspect of the invention involves contacting a cell expressing a functional TLR with an effective amount of a substituted 4-primary amino quinoline composition having structural Formula XVII

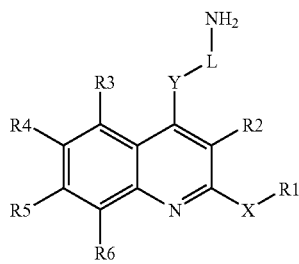

Formula XVII wherein

X is absent or is a nitrogen, oxygen, or sulfur atom or an SO or SO₂ group;

R₁ is a hydrogen atom or a substituted or unsubstituted aryl, alkyl, heterocyclic or styryl group;

R₂ is a hydrogen atom, a halogen atom, or an alkyl, alkenyl, aryl, heterocyclic, nitro, cyano, carboxy, ester, ketone, amino, amido, hydroxy, alkoxy, mercapto, thio, sulfoxide, sulfone, or sulfonamido group, wherein R₁ and R₂ optionally are combined to form a heterocycle or carbocycle;

Y is absent or is an oxygen atom, a sulfur atom, CR₇R₈, or NR₉, where R₇, R₈, and R₉ are each independently a hydrogen atom or a substituted or unsubstituted alkyl, alkenyl, or aryl group;

L is absent or is an alkyl or alkenyl group containing from 1 to 10 carbons or is an aryl group; and R₃, R₄, R₅, and R₆ are each independently a hydrogen atom, a halogen atom, or an alkyl, alkenyl, aryl, heterocyclic, nitro, cyano, carboxy, ester, ketone, amino, amido, hydroxy, alkoxy, mercapto, thio, sulfoxide, sulfone, or sulfonamido group, wherein any pair of R₃, R₄, R₅, and R₆ which are adjacent one another optionally are combined to form a heterocycle or a carbocycle, and pharmaceutically acceptable hydrates and salts thereof, to inhibit signaling by the TLR. The substituted 4-primary amino quinoline composition in this and all other aspects of the invention involving the use of a substituted 4-primary amino quinoline composition can be in the form a hydrate or pharmaceutically acceptable salt. The method according to this aspect of the invention can be performed in vitro or it can be performed in vivo. In addition, the cell expressing the functional TLR can, but need not necessarily, be an immune cell. For example, the cell expressing the functional TLR can be a cell transfected with an expression vector that directs expression of the TLR by the cell. In one embodiment the TLR is TLR9 and the method is thus a method for inhibiting intracellular signaling by TLR9.

In addition to compounds 101-104, 106-109, 111, 113-116, and 118-119, presented in Table 1, the following additional representative and non-limiting substituted 4-primary amino quinoline compounds, compounds 105, 110, 117, and 120-133, presented in Table 2 with reference to Formula XVII, can be used in the method according to this and all other aspects of the invention directed to methods involving use of substituted 4-primary amino quinoline compounds. Additional examples are presented in the Examples below.

TABLE 2
Additional Substituted 4-Primary Amino Quinoline Compositions for Use in Methods of the Invention
| ID | X | R₁ | Y | L | R₂ | R₃ | R₄ | R₅ | R₆ |
|---|---|---|---|---|---|---|---|---|---|
| 101 | absent | 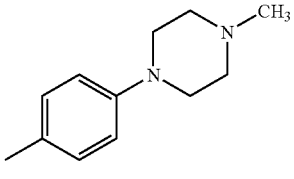 | NH | —(CH₂)₂— | H | H | H | H | H |
| 102 | absent | 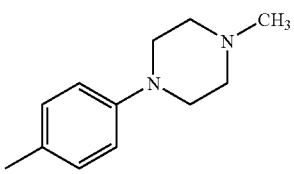 | NH | —(CH₂)₃— | H | H | H | H | H |
| 103 | absent | 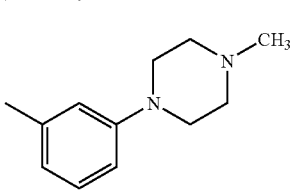 | NH | —(CH₂)₂— | H | H | H | H | H |
| 104 | absent | 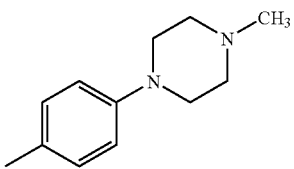 | NH | —(CH₂)₄— | H | H | H | H | H |
| 105 | absent | 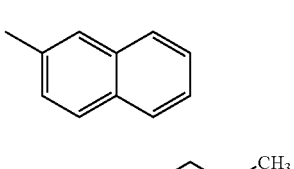 | NH | 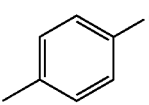 | H | H | H | H | H |
| 106 | absent | 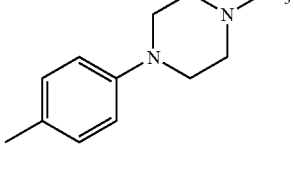 | NH | —(CH₂)₅— | H | H | H | H | H |
| 107 | absent | 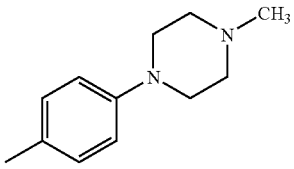 | NH | —(CH₂)₂— | H | H | Cl | H | H |
| 108 | absent | 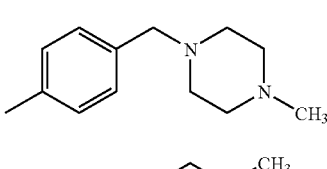 | NH | —(CH₂)₃— | H | H | H | H | H |
| 109 | absent | 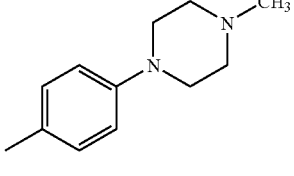 | NH | —(CH₂)₆— | H | H | H | H | H |

TABLE 2-continued

Additional Substituted 4-Primary Amino Quinoline Compositions for Use in Methods of the Invention

| ID | X | R₁ | Y | L | R₂ | R₃ | R₄ | R₅ | R₆ |
|---|---|---|---|---|---|---|---|---|---|
| 110 | absent | 6-hydroxy-2-naphthyl (methyl-substituted) | NH | —(CH₂)₂— | H | H | H | H | H |
| 111 | absent | 4-methylbenzyl-(4-methylpiperazin-1-yl) | NH | —(CH₂)₃— | H | H | H | H | H |
| 112 | absent | 6-methyl-2-naphthyl | NH | —(CH₂)₄— | H | H | H | H | H |
| 113 | absent | 4-cyclohexyl-methylphenyl | NH | —(CH₂)₂— | H | H | H | H | H |
| 114 | absent | 2-methyl-N-(2-(dimethylamino)ethyl)aniline | NH | —(CH₂)₃— | H | H | H | H | H |
| 115 | absent | 2-methyl-N-(2-(dimethylamino)ethyl)aniline | NH | —(CH₂)₄— | H | H | H | H | H |
| 116 | absent | 2-methyl-N-(2-(dimethylamino)ethyl)aniline | NH | —(CH₂)₂— | H | H | H | H | H |
| 117 | absent | (E)-propenylbenzene | NH | —(CH₂)₂— | H | H | H | H | H |
| 118 | absent | 2-methyl-N-(3-(dimethylamino)propyl)aniline | NH | —(CH₂)₃— | H | H | H | H | H |
| 119 | absent | 4-methylbenzyl-(4-methylpiperazin-1-yl) | NH | —(CH₂)₂— | H | H | H | H | H |

TABLE 2-continued

Additional Substituted 4-Primary Amino Quinoline Compositions for Use in Methods of the Invention

| ID | X | R₁ | Y | L | R₂ | R₃ | R₄ | R₅ | R₆ |
|---|---|---|---|---|---|---|---|---|---|
| 120 | absent | 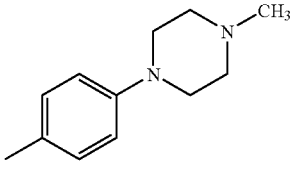 | NH | 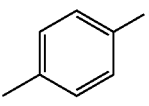 | H | H | H | H | H |
| 121 | absent | 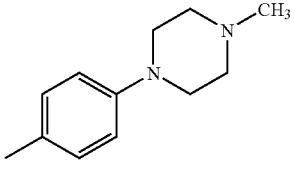 | | 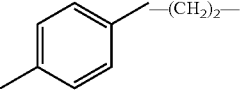 | H | H | H | H | H |
| 122 | NCH₃ | —CH₂— | absent | absent | CH₂ | H | H | H | H |
| 123 | NCH₃ | —CH₂— | absent | absent | CH₂ | H | CH₃ | H | H |
| 124 | NCH₃ | —CH₂— | absent | absent | CH₂ | H | Br | H | H |
| 125 | NCH₃ | —(CH₂)₃— | absent | absent | CH₂ | H | H | H | H |
| 126 | 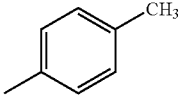 | —CH₂— | absent | absent | CH₂ | H | H | H | H |
| 127 | 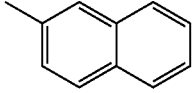 | —CH₂— | absent | absent | CH₂ | H | CH₃ | H | H |
| 128 | NCH₃ | CH₃ | absent | absent | H | H | H | H | H |
| 129 | absent | 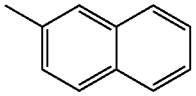 | NH | —(CH₂)₂— | H | H | Cl | H | H |
| 130 | absent | 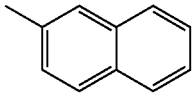 | NH | —(CH₂)₂— | H | H | Cl | H | H |
| 131 | absent |  | NCH₂CH₃ | —(CH₂)₂— | H | H | H | H | H |
| 132 | absent |  | O | —(CH₂)₂— | H | H | H | H | H |
| 133 | absent |  | S | —(CH₂)₂— | H | H | H | H | H |

In one aspect the invention provides a method for inhibiting signaling by a TLR. The method according to this aspect of the invention involves contacting an immune cell expressing a functional TLR with (a) an effective amount of a TLR signal agonist to stimulate signaling by the TLR in absence of a substituted 4-primary amino quinoline composition, and (b) an effective amount of a substituted 4-primary amino quinoline composition having structural Formula XVII, as defined above, to inhibit signaling by the TLR in response to the TLR signal agonist compared with the signaling by the TLR in response to the TLR signal agonist in absence of the substituted 4-primary amino quinoline composition. The substituted 4-primary amino quinoline composition in this aspect of the invention can be in the form a hydrate or pharmaceutically acceptable salt. The method according to this aspect of the invention can be performed in vitro or it can be performed in vivo.

Also according to this aspect of the invention, in one embodiment the TLR is TLR9 and the TLR signal agonist is a TLR9 signal agonist, and the method in one embodiment is thus a method of inhibiting intracellular signaling by TLR9 in response to a TLR9 signal agonist. The TLR signal agonist in one embodiment is CpG DNA, for example a CpG ODN such as ODN 2006. The CpG ODN can belong to any class of CpG ODN, including A-class (e.g., ODN 2216), B-class (e.g., ODN 2006), or C-class (e.g., ODN 2395).

In one embodiment the TLR signal agonist is an immune complex that includes a nucleic acid. Immune complexes that include a nucleic acid are known by those of skill in the art to include immunoglobulin complexed with nucleic acids that are either naked or, more commonly, that are associated with proteins or other non-nucleic acid components. The nucleic acids that are associated with proteins or other non-nucleic acid components can include, for example, chromatin, ribosomes, small nuclear proteins, ribonuclear proteins (RNP), histones, nucleosomal protein-DNA complexes, and nucleosomes. Examples of clinically important antibodies specific for nucleic acids and for nucleic acid-containing material include antinuclear antibodies (ANA), anti-dsDNA, anti-ss-DNA, anti-Sm, anti-RNP, anti-Ro (SS-A), anti-La (SS-B), and antihistone antibodies. Immune complexes that include a nucleic acid include, without limitation, immunoglobulin complexed with DNA, including specifically double-stranded DNA, and immunoglobulin complexed with nucleosomal material, both characteristic of systemic lupus erythematosus, and immunoglobulin complexed with RNA.

In one aspect the invention provides a method for inhibiting an immune response to an antigenic substance. The method according to this aspect of the invention involves contacting an immune cell expressing a functional Toll-like receptor with (a) an effective amount of an antigenic substance to stimulate an immune response to the antigenic substance in absence of a substituted 4-primary amino quinoline composition, and (b) an effective amount of a substituted 4-primary amino quinoline composition having structural Formula XVII, as defined above, to inhibit an immune response to the antigenic substance compared with the immune response to the antigenic substance in absence of the substituted 4-primary amino quinoline composition. The substituted 4-primary amino quinoline composition in this aspect of the invention can be in the form a hydrate or pharmaceutically acceptable salt. The method according to this aspect of the invention can be performed in vitro or it can be performed in vivo. In one embodiment the immune response is an innate immune response. In one embodiment the immune response includes an adaptive immune response.

In one embodiment the method involves contacting, in a subject, an immune cell expressing a functional Toll-like receptor with (a) an effective amount of an antigenic substance to stimulate an immune response in the subject to the antigenic substance in absence of a substituted 4-primary amino quinoline composition, and (b) an effective amount of a substituted 4-primary amino quinoline composition having structural Formula XVII, as defined above, to inhibit an immune response in the subject to the antigenic substance compared with the immune response to the antigenic substance in absence of the substituted 4-primary amino quinoline composition.

In one embodiment the step of contacting an immune cell expressing a functional Toll-like receptor with an effective amount of an antigenic substance to stimulate an immune response to the antigenic substance in absence of a substituted 4-primary amino quinoline composition involves the active step of administering an effective amount of an antigenic substance to stimulate an immune response to the antigenic substance in absence of a substituted 4-primary amino quinoline composition. The antigenic substance can be administered using any effective route or means for administering the antigenic substance to effect the contacting. By way of example, the administering can be by local or systemic injection, inhalation, oral ingestion, topical administration, mucosal administration, or any combination thereof.

In one embodiment the step of contacting an immune cell expressing a functional Toll-like receptor with an effective amount of an antigenic substance to stimulate an immune response to the antigenic substance in absence of a substituted 4-primary amino quinoline composition is passive. For example, in one embodiment the immune cell is already in contact or has already been in contact with an effective amount of an antigenic substance to stimulate an immune response to the antigenic substance, at the time of or prior to the step of contacting the immune cell expressing a functional Toll-like receptor with an effective amount of a substituted 4-primary amino quinoline composition having structural Formula XVII, as defined above, to inhibit an immune response to the antigenic substance compared with the immune response to the antigenic substance in absence of the substituted 4-primary amino quinoline composition.

The antigenic substance can be an allergen. An allergen is a substance that can induce an allergic or asthmatic response in a susceptible subject. The list of allergens is enormous and can include pollens, insect venoms, animal dander, dust, fungal spores and drugs (e.g., penicillin). Examples of natural animal and plant allergens include proteins specific to the following genera: *Canis* (*Canis familiaris*); *Dermatophagoides* (e.g., *Dermatophagoides farinae*); *Felis* (*Felis domesticus*); *Ambrosia* (*Ambrosia artemuisfolia*); *Lolium* (e.g., *Lolium perenne* or *Lolium multiflorum*); *Cryptomeria* (*Cryptomeria japonica*); *Alternaria* (*Alternaria alternata*); *Alder*; *Alnus* (*Alnus gultinosa*); *Betula* (*Betula verrucosa*); *Quercus* (*Quercus alba*); *Olea* (*Olea europa*); *Artemisia* (*Artemisia vulgaris*); *Plantago* (e.g., *Plantago lanceolata*); *Parietaria* (e.g., *Parietaria officinalis* or *Parietaria judaica*); *Blattella* (e.g., *Blattella germanica*); *Apis* (e.g., *Apis multiforum*); *Cupressus* (e.g., *Cupressus sempervirens, Cupressus arizonica*, and *Cupressus macrocarpa*); *Juniperus* (e.g., *Juniperus sabinoides, Juniperus virginiana, Juniperus communis*, and *Juniperus ashel*); *Thuya* (e.g., *Thuya orientalis*); *Chamaecyparis* (e.g., *Chamaecyparis obtusa*); *Periplaneta* (e.g., *Periplaneta americana*); *Agropyron* (e.g., *Agropyron*

*repens*); *Secale* (e.g., *Secale cereale*); *Triticum* (e.g., *Triticum aestivum*); *Dactylis* (e.g., *Dactylis glomerata*); *Festuca* (e.g., *Festuca elatior*); *Poa* (e.g., *Poa pratensis* or *Poa compressa*); *Avena* (e.g., *Avena sativa*); *Holcus* (e.g., *Holcus lanatus*); *Anthoxanthum* (e.g., *Anthoxanthum odoratum*); *Arrhenatherum* (e.g., *Arrhenatherum elatius*); *Agrostis* (e.g., *Agrostis alba*); *Phleum* (e.g., *Phleum pratense*); *Phalaris* (e.g., *Phalaris arundinacea*); *Paspalum* (e.g., *Paspalum notatum*); *Sorghum* (e.g., *Sorghum halepensis*); and *Bromus* (e.g., *Bromus inermis*). The term "allergy" refers to acquired hypersensitivity to a substance (allergen). An "allergic reaction" is the response of an immune system to an allergen in a subject allergic to the allergen. Allergic conditions include eczema, allergic rhinitis or coryza, hay fever, bronchial asthma, urticaria (hives) and food allergies, and other atopic conditions.

The antigenic substance can be an antigen that is or is derived from an infectious microbial agent, including a bacterium, a virus, a fungus, or a parasite. Examples of infectious bacteria include: *Helicobacter pyloris, Borrelia burgdorferi, Legionella pneumophilia, Mycobacteria* sps (such as. *M. tuberculosis, M. avium, M. intracellulare, M. kansasii*, and *M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidum, Treponema pertenue, Leptospira*, and *Actinomyces israelii*. Examples of infectious virus include: Retroviridae (including but not limited to human immunodeficiency virus (HIV)); Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bunyaviridae (for example, Hantaan viruses, bunya viruses, phleboviruses, and Nairo viruses); Arena viridae (hemorrhagic fever viruses); Reoviridae (e.g., reoviruses, orbiviurses, and rotaviruses); Bimaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, *cytomegalovirus* (CMV), herpes viruses); Poxyiridae (variola viruses, vaccinia viruses, pox viruses); and Iridoviridae (such as African swine fever virus); and unclassified viruses (for example, the etiological agents of spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses). Examples of infectious fungi include, but are not limited to, *Cryptococcus neoformans, Histoplasma capsulatum, Coccidioides immitis, Blastomyces dermatitidis, Chlamydia trachomatis*, and *Candida albicans*.

The antigenic substance can be a cancer antigen. A cancer antigen as used herein is a compound, such as a peptide or protein, associated with a tumor or cancer cell surface and which is capable of provoking an immune response when expressed on the surface of an antigen-presenting cell in the context of a major histocompatibility complex (MHC) molecule. Cancer antigens can be prepared from cancer cells either by preparing crude extracts of cancer cells, for example, as described in Cohen P A et al. (1994) *Cancer Res* 54:1055-8, by partially purifying the antigens, by recombinant technology, or by de novo synthesis of known antigens. Cancer antigens include but are not limited to antigens that are recombinantly expressed, an immunogenic portion thereof, or a whole tumor or cancer cell. Such antigens can be isolated or prepared recombinantly or by any other means known in the art.

The terms "cancer antigen" and "tumor antigen" are used interchangeably and refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses. Examples of tumor antigens include MAGE, MART-1/Melan-A, gp100, Dipeptidyl peptidase IV (DPPIV), adenosine deaminase-binding protein (ADAbp), cyclophilin b, Colorectal associated antigen (CRC)—C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21 ras, RCAS1, α-fetoprotein, E-cadherin, α-catenin, β-catenin and γ-catenin, p120ctn, gp100$^{Pmel\ 117}$, PRAME, NY-ESO-1, cdc27, adenomatous polyposis coli protein (APC), fodrin, Connexin 37, Ig-idiotype, p15, gp75, GM2 and GD2 gangliosides, viral products such as human papillomavirus proteins, Smad family of tumor antigens, lmp-1, P1 A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2.

Cancers or tumors and tumor antigens associated with such tumors (but not exclusively), include acute lymphoblastic leukemia (etv6; aml1; cyclophilin b), B cell lymphoma (Ig-idiotype), glioma (E-cadherin; α-catenin; β-catenin; γ-catenin; p120ctn), bladder cancer (p21ras), biliary cancer (p21ras), breast cancer (MUC family; HER2/neu; c-erbB-2), cervical carcinoma (p53; p21ras), colon carcinoma (p21ras; HER2/neu; c-erbB-2; MUC family), colorectal cancer (Colorectal associated antigen (CRC)—C017-1A/GA733; APC), choriocarcinoma (CEA), epithelial cell cancer (cyclophilin b), gastric cancer (HER2/neu; c-erbB-2; ga733 glycoprotein), hepatocellular cancer (α-fetoprotein), Hodgkins lymphoma (lmp-1; EBNA-1), lung cancer (CEA; MAGE-3; NY-ESO-1), lymphoid cell-derived leukemia (cyclophilin b), melanoma (p15 protein, gp75, oncofetal antigen, GM2 and GD2 gangliosides), myeloma (MUC family; p21ras), non-small cell lung carcinoma (HER2/neu; c-erbB-2), nasopharyngeal cancer (lmp-1; EBNA-1), ovarian cancer (MUC family; HER2/neu; c-erbB-2), prostate cancer (Prostate Specific Antigen (PSA) and its immunogenic epitopes PSA-1, PSA-2, and PSA-3; prostate-specific membrane antigen (PSMA); HER2/neu; c-erbB-2), pancreatic cancer (p21ras; MUC family; HER2/neu; c-erbB-2; ga733 glycoprotein), renal cancer (HER2/neu; c-erbB-2), squamous cell cancers of cervix and esophagus (viral products such as human papillomavirus proteins), testicular cancer (NY-ESO-1), T-cell leukemia (HTLV-1 epitopes), and melanoma (Melan-A/MART-1; cdc27; MAGE-3; p21ras; gp100$^{Pmel117}$).

In one aspect of the invention, a method of treating an autoimmune disorder in a subject is provided. The method according to this aspect of the invention involves the step of administering to a subject having an autoimmune disorder an effective amount of a substituted 4-primary amino quinoline composition having structural Formula XVII, as defined above, to treat the autoimmune disorder. The substituted 4-primary amino quinoline composition in this aspect of the invention can be in the form a hydrate or pharmaceutically acceptable salt. In one embodiment the autoimmune disorder is chosen from systemic lupus erythematosus, rheumatoid arthritis, inflammatory bowel disease, Sjögren's syndrome, polymyositis, vasculitis, Wegener's granulomatosis, sarcoidosis, ankylosing spondylitis, Reiter's syndrome, psoriatic arthritis, and Behcet's syndrome. In one particular embodiment the autoimmune disease is systemic lupus erythematosus. In one particular embodiment the autoimmune disease is rheumatoid arthritis. In one embodiment the subject is a human. The method can also be applied to animal models of any of the autoimmune disorders listed above.

In one embodiment the autoimmune disorder is an immune complex associated disease. Immune complex associated diseases specifically include, without limitation, systemic lupus erythematosus, rheumatoid arthritis, polyarteritis nodosa, poststreptococcal glomerulonephritis, cryoglobulinemia, and acute and chronic serum sickness.

The substituted 4-primary amino quinoline composition can be administered to the subject by any suitable route of administration, including, without limitation, oral and parenteral. Parenteral routes of administration include, without limitation, intravenous, intramuscular, intraperitoneal, subcutaneous, intranasal, intrapulmonary, transdermal, topical, and mucosal. Parenteral routes of administration also include direct injection into a specific tissue or other site of injection, including, for example, lymphoid tissue and a site of inflammation.

It has been discovered according to the invention that quinzoline compounds structurally similar to quinolines of the invention are unexpectedly useful in methods for inhibiting an immune response, both in vitro and in vivo, including methods for treating immune complex associated diseases and autoimmune disorders. The quinazoline compounds and their methods of use according to the invention were unexpectedly found to retain much or all of the immunoinhibitory features of corresponding quinoline compounds and their methods of use, but with the additional feature of having reduced toxicity, at least in vivo.

In one aspect the invention provides novel quinazoline compositions. As described further below, these compositions and other quinazoline compositions have been discovered to be useful in methods for inhibiting an immune response, both in vitro and in vivo, including methods for treating immune complex associated diseases and autoimmune disorders. Due to their similarity to certain known antimalarial agents, it is also believed that the novel quinazoline compositions of the invention will also be useful for prevention and treatment of malaria, as well as for treatment of other diseases which have been described to be responsive to treatment with chloroquines.

The novel quinazoline compositions of the invention have a structural Formula XVIII

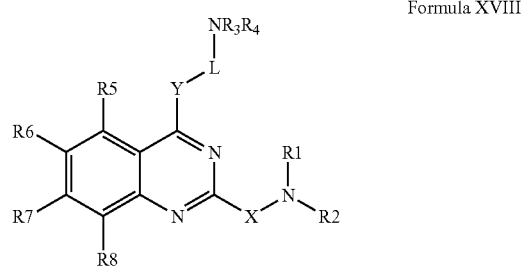

Formula XVIII wherein

X is absent or is an aryl, alkyl, heterocyclic or styryl group, provided that if X is a phenyl group, $NR_1R_2$ is part if a heterocycle or is a diamine;

$R_1$ and $R_2$ are each independently a hydrogen atom or an alkyl, alkenyl, or aryl group, wherein $R_1$ and $R_2$ optionally are combined to form a heterocycle;

Y is an oxygen atom, a sulfur atom, $CR_9$, $R_{10}$, or $NR_{11}$, where $R_9$, $R_{10}$, and $R_{11}$, are each independently a hydrogen atom or an alkyl, alkenyl, or aryl group, wherein any one of $R_9$, $R_{10}$, and $R_{11}$ optionally is combined with $R_3$ or $R_4$ to form a substituted or unsubstituted heterocycle;

L is an alkyl or alkenyl group containing from 1 to 10 carbons or is an aryl group;

$R_3$ and $R_4$ are each independently a hydrogen atom or an alkyl, alkenyl, or aryl group, wherein $R_3$ and $R_4$ optionally are combined to form a heterocycle; and $R_5$, $R_6$, $R_7$, and $R_8$ are each independently a hydrogen atom, a halogen atom, or an alkyl, alkenyl, aryl, heterocyclic, nitro, cyano, carboxy, ester, ketone, amino, amido, hydroxy, alkoxy, mercapto, thio, sulfoxide, sulfone, or sulfonamido group, wherein any pair of $R_5$, $R_6$, $R_7$, and $R_8$ which are adjacent one another optionally are combined to form a heterocycle or a carbocycle, and pharmaceutically acceptable hydrates and salts thereof.

In one embodiment $R_6$ and $R_7$ are each independently a halogen atom or an alkoxy group.

In one embodiment $R_6$ and $R_7$ are each independently a chlorine atom or a methoxy group.

In one embodiment X is absent or is an aryl group;

$NR_1R_2$ is a heterocyclic amine or $NR_{13}(CH_2)_nNR_{14}R_{15}$, wherein n is an integer from 2 to 6, inclusive, and $R_{13}$, $R_{14}$, and $R_{15}$ are each independently a hydrogen atom or an alkyl group;

Y is an aryl group or is $NR_{12}$ where $R_{12}$ is a hydrogen atom or an aryl or alkyl group;

L is absent or is a $C_2$-$C_6$ alkyl group;

$R_3$ and $R_4$ are each independently a hydrogen atom or an alkyl group, wherein $R_3$ and $R_4$ optionally are combined to form a heterocycle; and $R_5$, $R_6$, $R_7$, and $R_8$ are each independently a hydrogen atom, a halogen atom, or an alkoxy group.

In one embodiment X is absent or is an aryl group;

$NR_1R_2$ is a substituted or unsubstituted piperazino or morpholino group or is $NR_{13}(CH_2)_nNR_{14}R_{15}$, wherein n is an integer from 2 to 6, inclusive, $R_{13}$ is a hydrogen atom, and $R_{14}$ and $R_{15}$ are each independently an alkyl group;

Y is NH;

L is a $C_2$-$C_6$ alkyl group;

$R_3$ and $R_4$ are each independently a hydrogen atom or an alkyl group, wherein $R_3$ and $R_4$ optionally are combined to form a heterocycle; and $R_5$, $R_6$, $R_7$, and $R_8$ are each independently a hydrogen atom, a halogen atom, or an alkoxy group.

In one embodiment X is an aryl group;

$NR_1R_2$ is substituted or unsubstituted piperazino or morpholino group;

Y is NH;

L is a $C_2$-$C_6$ alkyl group;

$R_3$ and $R_4$ are each independently a methyl or ethyl group or $R_3$ and $R_4$ optionally are combined to form a morpholino group; and $R_5$, $R_6$, $R_7$, and $R_8$ are each independently a hydrogen atom, a halogen atom, or an alkoxy group.

In one embodiment X is a phenyl group;

$NR_1R_2$ is N-methylpiperazine;

Y is NH;

L is —$CH_2CH_2$—;

$R_3$ and $R_4$ are each a methyl group; and $R_5$, $R_6$, $R_7$, and $R_8$ are each a hydrogen atom.

In one embodiment X is a phenyl group;

$NR_1R_2$ is N-methylpiperazine;

Y is NH;

L is —$CH_2CH_2$—;

$R_3$ and $R_4$ are combined as a morpholino group; and $R_5$, $R_6$, $R_7$, and $R_8$ are each a hydrogen atom.

In one embodiment X is absent;

$NR_1R_2$ is a substituted or unsubstituted piperazino or morpholino group;

Y is NH;

L is a $C_2$-$C_6$ alkyl group;

$R_3$ and $R_4$ are each independently a methyl or ethyl group or $R_3$ and $R_4$ optionally are combined to form a morpholino group; and $R_5$, $R_6$, $R_7$, and $R_8$ are each independently a hydrogen atom, a halogen atom, or an alkoxy group.

In one embodiment X is absent;

$NR_1R_2$ is N-methylpiperazine;

Y is NH;

L is —$CH_2CH_2$—;

$R_3$ and $R_4$ are each a methyl group;

$R_6$ and $R_7$ are each a methoxy group; and $R_5$ and $R_8$ are each a hydrogen atom.

In one embodiment X is absent;

$NR_1R_2$ is N-phenylpiperazine;

Y is NH;

L is —$CH_2CH_2$—;

$R_3$ and $R_4$ are each a methyl group;

$R_6$ and $R_7$ are each a methoxy group; and $R_5$ and $R_8$ are each a hydrogen atom.

In one embodiment X is absent;

$NR_1R_2$ is N-methylpiperazine;

Y is NH;

L is —$CH_2CH_2$;

$R_3$ and $R_4$ are combined as a morpholino group;

$R_6$ and $R_7$ are each a methoxy group; and $R_5$ and $R_9$ are each a hydrogen atom.

In each of the foregoing embodiments, the composition is optionally in the form of a pharmaceutically acceptable hydrate or salt.

Representative, non-limiting examples of quinazoline compositions of Formula XVIII of the invention are compounds 201-214, presented in Table 3.

TABLE 3

Quinazoline Compositions of the Invention

| ID | X | $NR_1R_2$ | Y | L | $R_3$ | $R_4$ | $R_5$ | $R_6$ | $R_7$ | $R_8$ |
|---|---|---|---|---|---|---|---|---|---|---|
| 201 | 4-methylphenyl | N-methylpiperazine | NH | —$(CH_2)_2$— | $CH_3$ | $CH_3$ | H | H | H | H |
| 202 | 4-methylphenyl | N-methylpiperazine | NH | —$(CH_2)_3$— | $CH_3$ | $CH_3$ | H | H | H | H |
| 203 | 4-methylphenyl | N-methylpiperazine | NH | —$(CH_2)_4$— | $CH_3$ | $CH_3$ | H | H | H | H |
| 204 | 4-methylphenyl | N-methylpiperazine | NH | —$(CH_2)_5$— | $CH_3$ | $CH_3$ | H | H | H | H |

TABLE 3-continued

Quinazoline Compositions of the Invention

| ID | X | NR$_1$R$_2$ | Y | L | R$_3$ | R$_4$ | R$_5$ | R$_6$ | R$_7$ | R$_8$ |
|---|---|---|---|---|---|---|---|---|---|---|
| 205 | 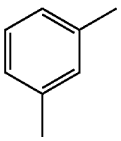 | 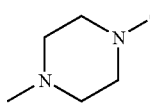 | NH | —(CH$_2$)$_2$— | CH$_3$ | CH$_3$ | H | H | H | H |
| 206 | 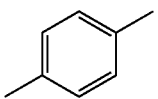 | 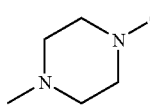 | NH | —(CH$_2$)$_2$— | CH$_2$CH$_3$ | CH$_2$CH$_3$ | H | H | H | H |
| 207 | 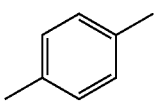 | 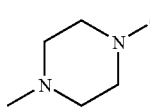 | NH | —(CH$_2$)$_2$— | CH$_3$ | CH$_3$ | H | Cl | H | H |
| 208 | 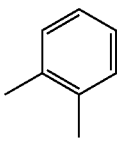 | 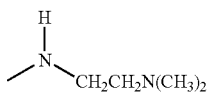 | NH | —(CH$_2$)$_2$— | CH$_3$ | CH$_3$ | H | H | H | H |
| 209 | 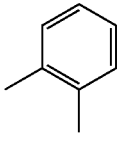 | 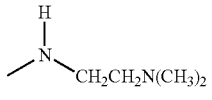 | NH | —(CH$_2$)$_3$— | CH$_3$ | CH$_3$ | H | H | H | H |
| 210 | 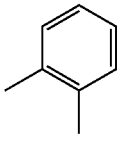 | 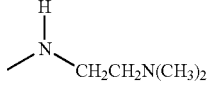 | NH | —(CH$_2$)$_2$— | CH$_3$ | CH$_3$ | H | H | H | H |
| 211 | 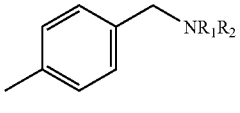 | 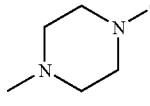 | NH | —(CH$_2$)$_3$— | CH$_3$ | CH$_3$ | H | H | H | H |
| 212 | 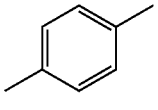 | 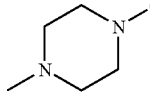 | NH | —(CH$_2$)$_2$— | CH$_3$ | CH$_3$ | H | OCH$_3$ | OCH$_3$ | H |
| 213 | 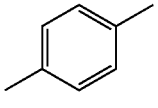 | 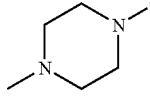 | O | —(CH$_2$)$_2$— | CH$_3$ | CH$_3$ | H | H | H | H |
| 214 | 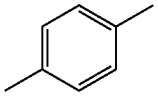 | 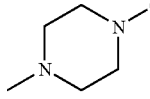 | S | —(CH$_2$)$_2$— | CH$_3$ | CH$_3$ | H | H | H | H |

It has been discovered according to the invention that certain quinazoline compositions can be used to inhibit TLR9 signaling.

In one aspect the invention provides additional novel quinazoline compounds useful in the methods of the invention. Such compounds are referred to herein as CMZ 203-34, CMZ 203-44, CMZ 203-45, CMZ 203-49, CMZ 203-51, CMZ 203-76, CMZ 203-78, CMZ 203-87, CMZ 203-93, and CMZ 203-95. Syntheses for each of these novel compounds are provided in Examples 19-28, respectively.

Certain of these specific compounds have already been tested in vitro and found to inhibit TLR9 signaling. See Example 29. Thus compounds CMZ 203-34, CMZ 203-44, CMZ 203-45, CMZ 203-49, CMZ 203-51, CMZ 203-76, CMZ 203-78, CMZ 203-87, CMZ 203-93, and CMZ 203-95 are believed to be useful in the methods of the invention.

In one aspect the invention provides a method for inhibiting signaling by a TLR. The method according to this aspect of the invention involves contacting a cell expressing a functional TLR with an effective amount of quinazoline composition having structural Formula XIX

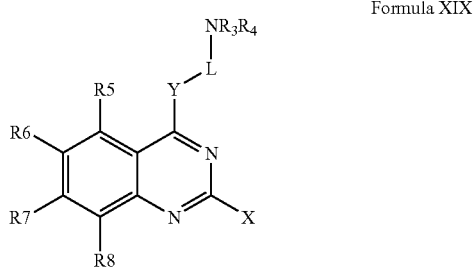

Formula XIX wherein

X is a substituted or unsubstituted aryl, alkyl, heterocyclic or styryl group, optionally attached to the quinazoline by a nitrogen, oxygen, or sulfur atom or by a SO or $SO_2$ group;

Y is absent or is an oxygen atom, a sulfur atom, $CR_9R_{10}$, or $NR_{11}$, where $R_9$, $R_{10}$, and $R_{11}$ are each independently a hydrogen atom or an alkyl, alkenyl, or aryl group, wherein any one of $R_9$, $R_{10}$, and $R_{11}$ optionally is combined with $R_3$ or $R_4$ to form a heterocycle;

L is absent or is a hydrogen atom, an alkyl or alkenyl group containing from 1 to 10 carbons, or an aryl group;

$R_3$ and $R_4$ are each independently a hydrogen atom or an alkyl, alkenyl, or aryl group, wherein $R_3$ and $R_4$ optionally are combined to form a heterocycle; and $R_5$, $R_6$, $R_7$, and $R_8$ are each independently a hydrogen atom, a halogen atom, or an alkyl, alkenyl, aryl, heterocyclic, nitro, cyano, carboxy, ester, ketone, amino, amido, hydroxy, alkoxy, mercapto, thio, sulfoxide, sulfone, or sulfonamido group, wherein any pair of $R_5$, $R_6$, $R_7$, and $R_8$ which are adjacent one another optionally are combined to form a heterocycle or a carbocycle, and pharmaceutically acceptable hydrates and salts thereof, to inhibit signaling by the TLR. The method according to this aspect of the invention can be performed in vitro or it can be performed in vivo. In addition, the cell expressing the functional TLR can, but need not necessarily, be an immune cell. For example, the cell expressing the functional TLR can be a cell transfected with an expression vector that directs expression of the TLR by the cell. In one embodiment the TLR is TLR9 and the method is thus a method for inhibiting intracellular signaling by TLR9.

In addition to compounds 201-214, presented in Table 3, the following additional representative and non-limiting quinazoline compounds, compounds 215-229, presented in Table 4 with reference to Formula XIX, can be used in the method according to this and all other aspects of the invention directed to methods involving use of substituted 4-primary amino quinoline compounds. Additional examples are presented in the Examples below.

TABLE 4

Additional Quinazoline Compositions for Use in Methods of the Invention

| ID | X | Y | L | $R_3$ | $R_4$ | $R_5$ | $R_6$ | $R_7$ | $R_8$ |
|---|---|---|---|---|---|---|---|---|---|
| 201 | 4-methylphenyl-piperazinyl-N-CH₃ | NH | —(CH₂)₂— | CH₃ | CH₃ | H | H | H | H |
| 202 | 4-methylphenyl-piperazinyl-N-CH₃ | NH | —(CH₂)₃— | CH₃ | CH₃ | H | H | H | H |
| 203 | 4-methylphenyl-piperazinyl-N-CH₃ | NH | —(CH₂)₄— | CH₃ | CH₃ | H | H | H | H |
| 204 | 4-methylphenyl-piperazinyl-N-CH₃ | NH | —(CH₂)₅— | CH₃ | CH₃ | H | H | H | H |

TABLE 4-continued

Additional Quinazoline Compositions for Use in Methods of the Invention

| ID | X | Y | L | $R_3$ | $R_4$ | $R_5$ | $R_6$ | $R_7$ | $R_8$ |
|---|---|---|---|---|---|---|---|---|---|
| 205 | 3-(4-methylpiperazin-1-yl)-phenyl (with CH3 on piperazine N) | NH | —(CH$_2$)$_2$— | CH$_3$ | CH$_3$ | H | H | H | H |
| 206 | 4-methylphenyl-piperazinyl-CH3 | NH | —(CH$_2$)$_2$— | CH$_2$CH$_3$ | CH$_2$CH$_3$ | H | H | H | H |
| 207 | 4-methylphenyl-piperazinyl-CH3 | NH | —(CH$_2$)$_2$— | CH$_3$ | CH$_3$ | H | Cl | H | H |
| 208 | 2-methylphenyl-NH-CH$_2$CH$_2$N(CH$_3$)$_2$ | NH | —(CH$_2$)$_2$— | CH$_3$ | CH$_3$ | H | H | H | H |
| 209 | 2-methylphenyl-NH-CH$_2$CH$_2$N(CH$_3$)$_2$ | NH | —(CH$_2$)$_3$— | CH$_3$ | CH$_3$ | H | H | H | H |
| 210 | 2-methylphenyl-NH-(CH$_2$)$_3$N(CH$_3$)$_2$ | NH | —(CH$_2$)$_2$— | CH$_3$ | CH$_3$ | H | H | H | H |
| 211 | 4-methylbenzyl-(4-methylpiperazin-1-yl) | NH | —(CH$_2$)$_3$— | CH$_3$ | CH$_3$ | H | H | H | H |
| 212 | 4-methylphenyl-piperazinyl-CH3 | NH | —(CH$_2$)$_2$— | CH$_3$ | CH$_3$ | H | OCH$_3$ | OCH$_3$ | H |
| 213 | 4-methylphenyl-piperazinyl-CH3 | O | —(CH$_2$)$_2$— | CH$_3$ | CH$_3$ | H | H | H | H |

TABLE 4-continued

Additional Quinazoline Compositions for Use in Methods of the Invention

| ID | X | Y | L | $R_3$ | $R_4$ | $R_5$ | $R_6$ | $R_7$ | $R_8$ |
|----|---|---|---|-------|-------|-------|-------|-------|-------|
| 214 | 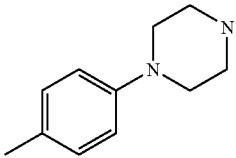 | S | —(CH$_2$)$_2$— | CH$_3$ | CH$_3$ | H | H | H | H |
| 215 | 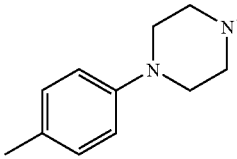 | N(CH$_3$) | —(CH$_2$)$_2$— | CH$_3$ | CH$_3$ | H | H | H | H |
| 216 | 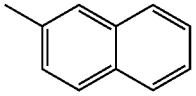 | NH | —(CH$_2$)$_2$— | CH$_3$ | CH$_3$ | H | H | H | H |
| 217 | 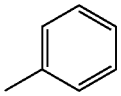 | NH | —(CH$_2$)$_2$— | CH$_3$ | CH$_3$ | H | H | H | H |
| 218 | 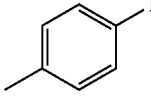 | NH | —(CH$_2$)$_2$— | CH$_3$ | CH$_3$ | H | H | H | H |
| 219 | 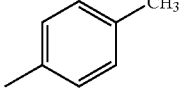 | NH | —(CH$_2$)$_2$— | CH$_3$ | CH$_3$ | H | H | H | H |
| 220 | 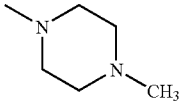 | NH | —(CH$_2$)$_2$— | CH$_3$ | CH$_3$ | H | H | H | H |
| 221 | 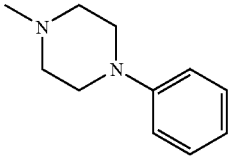 | NH | —(CH$_2$)$_2$— | CH$_3$ | CH$_3$ | H | H | H | H |
| 222 | 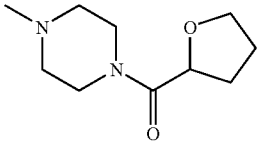 | absent | absent | H | H | H | OCH$_3$ | OCH$_3$ | H |
| 223 | 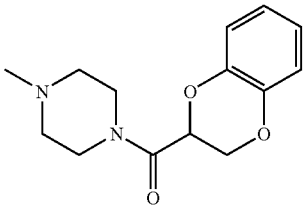 | absent | absent | H | H | H | OCH$_3$ | OCH$_3$ | H |

TABLE 4-continued

Additional Quinazoline Compositions for Use in Methods of the Invention

| ID | X | Y | L | $R_3$ | $R_4$ | $R_5$ | $R_6$ | $R_7$ | $R_8$ |
|---|---|---|---|---|---|---|---|---|---|
| 224 | tolyl | absent | —(CH$_2$)$_3$— | CH$_2$CH$_3$ | CH$_2$CH$_3$ | H | H | H | H |
| 225 | 4-methylpiperazinyl | absent | absent | benzylamino | H | H | H | H | H |
| 226 | morpholinomethyl | absent | absent | benzylamino | H | H | H | H | H |
| 227 | furfurylamino | absent | absent | benzylamino | H | H | H | H | H |
| 228 | 4-(2-hydroxyethyl)-methylpiperazinyl | absent | absent | benzylamino | H | H | H | H | H |
| 229 | benzylamino | absent | absent | H | H | H | H | H | H |

In one aspect the invention provides a method for inhibiting signaling by a TLR. The method according to this aspect of the invention involves contacting an immune cell expressing a functional TLR with (a) an effective amount of a TLR signal agonist to stimulate signaling by the TLR in absence of a quinazoline composition, and (b) an effective amount of a quinazoline composition having structural Formula XIX, as defined above, to inhibit signaling by the TLR in response to the TLR signal agonist compared with the signaling by the TLR in response to the TLR signal agonist in absence of the quinazoline composition. The quinazoline composition in this aspect of the invention can be in the form a hydrate or pharmaceutically acceptable salt. The method according to this aspect of the invention can be performed in vitro or it can be performed in vivo.

Also according to this aspect of the invention, in one embodiment the TLR is TLR9 and the TLR signal agonist is a TLR9 signal agonist, and the method in one embodiment is thus a method of inhibiting intracellular signaling by TLR9 in response to a TLR9 signal agonist. The TLR signal agonist in one embodiment is CpG DNA, for example a CpG ODN such as ODN 2006. The CpG ODN can belong to any class of CpG ODN, including A-class (e.g., ODN 2216), B-class (e.g., ODN 2006), or C-class (e.g., ODN 2395).

In one embodiment the TLR signal agonist is an immune complex that includes a nucleic acid, as described above.

In one aspect the invention provides a method for inhibiting an immune response to an antigenic substance. The method according to this aspect of the invention involves contacting an immune cell expressing a functional Toll-like receptor with (a) an effective amount of an antigenic substance to stimulate an immune response to the antigenic substance in absence of a quinazoline composition, and (b) an effective amount of a quinazoline composition having structural Formula XIX, as defined above, to inhibit an immune response to the antigenic substance compared with the immune response to the antigenic substance in absence of the quinazoline composition. The quinazoline composition in this aspect of the invention can be in the form a hydrate or pharmaceutically acceptable salt. The method according to this aspect of the invention can be performed in vitro or it can be performed in vivo. In one embodiment the immune response is an innate immune response. In one embodiment the immune response includes an adaptive immune response.

In one embodiment the step of contacting an immune cell expressing a functional Toll-like receptor with an effective amount of an antigenic substance to stimulate an immune response to the antigenic substance in absence of a quinazoline composition involves the active step of administering an effective amount of an antigenic substance to stimulate an immune response to the antigenic substance in absence of a quinazoline composition. The antigenic substance can be administered using any effective route or means for administering the antigenic substance to effect the contacting. By way of example, the administering can be by local or systemic injection, inhalation, oral ingestion, topical administration, mucosal administration, or any combination thereof.

In one embodiment the method involves contacting, in a subject, an immune cell expressing a functional Toll-like receptor with (a) an effective amount of an antigenic substance to stimulate an immune response in the subject to the antigenic substance in absence of a quinazoline composition, and (b) an effective amount of a quinazoline composition having structural Formula XVII, as defined above, to inhibit an immune response in the subject to the antigenic substance compared with the immune response to the antigenic substance in absence of the quinazoline composition.

In one embodiment the step of contacting an immune cell expressing a functional Toll-like receptor with an effective amount of an antigenic substance to stimulate an immune response to the antigenic substance in absence of a quinazoline composition is passive. For example, in one embodiment the immune cell is already in contact or has already been in contact with an effective amount of an antigenic substance to stimulate an immune response to the antigenic substance, at the time of or prior to the step of contacting the immune cell expressing a functional Toll-like receptor with an effective amount of a quinazoline composition having structural Formula XVII, as defined above, to inhibit an immune response to the antigenic substance compared with the immune response to the antigenic substance in absence of the quinazoline composition.

The antigenic substance can be an allergen, as described above.

The antigenic substance can be an antigen that is or is derived from an infectious microbial agent, including a bacterium, a virus, a fungus, or a parasite, as described above.

The antigenic substance can be a cancer antigen, as described above.

In one aspect of the invention, a method of treating an autoimmune disorder in a subject is provided. The method according to this aspect of the invention involves the step of administering to a subject having an autoimmune disorder an effective amount of a quinazoline composition having structural Formula XIX, as defined above, to treat the autoimmune disorder. The quinazoline composition in this aspect of the invention can be in the form a hydrate or pharmaceutically acceptable salt. In one embodiment the autoimmune disorder is chosen from systemic lupus erythematosus, rheumatoid arthritis, inflammatory bowel disease, Sjögren's syndrome, polymyositis, vasculitis, Wegener's granulomatosis, sarcoidosis, ankylosing spondylitis, Reiter's syndrome, psoriatic arthritis, and Behçet's syndrome. In one particular embodiment the autoimmune disease is systemic lupus erythematosus. In one particular embodiment the autoimmune disease is rheumatoid arthritis. In one embodiment the subject is a human. The method can also be applied to animal models of any of the autoimmune disorders listed above.

In one embodiment the autoimmune disorder is an immune complex associated disease, as described above.

The quinazoline composition can be administered to the subject by any suitable route of administration, including, without limitation, oral and parenteral. Parenteral routes of administration are as described above with respect to substituted 4-primary amino quinolines.

Assays for Effectiveness

The methods of the invention can be assessed using any of a number of possible readout systems based upon a TLR/IL-1R signal transduction pathway. In some embodiments, the readout for the method is based on the use of native genes or, alternatively, transfected or otherwise artificially introduced reporter gene constructs which are responsive to the TLR/IL-1R signal transduction pathway involving MyD88, TRAF, p38, and/or ERK. Häcker H et al. (1999) *EMBO J.* 18:6973-82. These pathways activate kinases including κB kinase complex and c-Jun N-terminal kinases. Thus reporter genes and reporter gene constructs particularly useful for the assays include, e.g., a reporter gene operatively linked to a promoter sensitive to NF-κB. Examples of such promoters include, without limitation, those for NF-κB, IL-1β, IL-6, IL-8, IL-12 p40, IP-10, CD80, CD86, and TNF-α. The reporter gene operatively linked to the TLR-sensitive promoter can include, without limitation, an enzyme (e.g., luciferase, alkaline phosphatase, β-galactosidase, chloramphenicol acetyltransferase (CAT), etc.), a bioluminescence marker (e.g., green-fluorescent protein (GFP, e.g., U.S. Pat. No. 5,491,084), blue fluorescent protein (BFP, e.g., U.S. Pat. No. 6,486,382), etc.), a surface-expressed molecule (e.g., CD25, CD80, CD86), and a secreted molecule (e.g., IL-1, IL-6, IL-8, IL-12 p40, TNF-α). In certain embodiments the reporter is selected from IL-8, TNF-α, NF-κB-luciferase (NF-κB-luc; Häcker H et al. (1999) *EMBO J.* 18:6973-82), IL-12 p40-luc (Murphy T L et al. (1995) *Mol Cell Biol* 15:5258-67), and TNF-luc (Häcker H et al. (1999) *EMBO J.* 18:6973-82). In assays relying on enzyme activity readout, substrate can be supplied as part of the assay, and detection can involve measurement of chemiluminescence, fluorescence, color development, incorporation of radioactive label, drug resistance, or other marker of enzyme activity. For assays relying on surface expression of a molecule, detection can be accomplished using flow cytometry (FACS) analysis or functional assays. Secreted molecules can be assayed using enzyme-linked immunosorbent assay (ELISA) or bioassays. Many of these and other suitable readout systems are well known in the art and are commercially available.

Reporter Constructs

A cell expressing a functional TLR and useful for the methods of the invention has, in some embodiments, an expression vector including an isolated nucleic acid which encodes a reporter construct useful for detecting TLR signaling. The expression vector including an isolated nucleic acid which encodes a reporter construct useful for detecting TLR signaling can include a reporter gene under control of a promoter response element (enhancer element). In some embodiments the promoter response element is associated with a minimal promoter responsive to a transcription factor believed by the applicant to be activated as a consequence of TLR signaling. Examples of such minimal promoters include, without limitation, promoters for the following genes: AP-1, NF-κB, ATF2, IRF3, and IRF7. These minimal promoters contain corresponding promoter response elements sensitive to AP-1, NF-κB, ATF2, IRF3, and IRF7, respectively. In other embodiments the expression vector including an isolated nucleic acid which encodes a reporter construct useful for detecting TLR signaling can include a gene under control of a promoter response element selected from response elements sensitive to IL-6, IL-8, IL-12 p40 subunit, a type I IFN, RANTES, TNF, IP-10, I-TAC, and interferon-stimulated response element (ISRE). The promoter response element generally will be present in multiple copies, e.g., as tandem repeats. For example, in one reporter construct, coding sequence for luciferase is under control of an upstream 6× tandem repeat of NF-κB response element. In another example, an ISRE-luciferase reporter construct useful in the invention is available from Stratagene (catalog no. 219092) and includes a 5× ISRE tandem repeat joined to a TATA box upstream of a luciferase reporter gene. As discussed further elsewhere herein, the reporter itself can be any gene product suitable for detection by methods recognized in the art. Such methods for detection can include, for example, measurement of spontaneous or stimulated light emission, enzyme activity, expression of a soluble molecule, expression of a cell surface molecule, etc.

Readouts typically involve usual elements of Toll/IL-1R signaling, e.g., MyD88, TRAF, and IRAK molecules, although in the case of TLR3 the role of MyD88 is less clear than for other TLR family members. As demonstrated herein such responses include the induction of a gene under control of a specific promoter such as a NF-κB promoter, increases in particular cytokine levels, increases in particular chemokine levels, etc. The gene under the control of the NF-κB promoter can be a gene which naturally includes an NF-κB promoter or it can be a gene in a construct in which an NF-κB promoter has been inserted. Genes and constructs which include the NF-κB promoter include but are not limited to IL-8, IL-12 p40, NF-κB-luc, IL-12 p40-luc, and TNF-luc.

Increases in cytokine levels can result from increased production, increased stability, increased secretion, or any combination of the forgoing, of the cytokine in response to the TLR-mediated signaling. Cytokines generally include, without limitation, IL-1, IL-2, IL-3, IL-4, IL-5, IL-6, IL-7, IL-10, IL-11, IL-12, IL-13, IL-15, IL-18, IFN-α, IFN-β, IFN-γ, TNF-α, GM-CSF, G-CSF, M-CSF. Th1 cytokines include but are not limited to IL-2, IFN-γ, and IL-12. Th2 cytokines include but are not limited to IL-4, IL-5, and IL-10.

Increases in chemokine levels can result from increased production, increased stability, increased secretion, or any combination of the forgoing, of the chemokine in response to the TLR-mediated signaling. Chemokines of particular significance in the invention include but are not limited to CCL5 (RANTES), CXCL9 (Mig), CXCL10 (IP-10), and CXCL11 (I-TAC), IL-8, and MCP-1.

Administration to a Subject

Some aspects of the invention involve administering an effective amount of a composition to a subject to achieve a specific outcome. The small molecule compositions useful according to the methods of the present invention thus can be formulated in any manner suitable for pharmaceutical use.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the compound can be administered to a subject by any mode allowing the compound to be taken up by the appropriate target cells. "Administering" the pharmaceutical composition of the present invention can be accomplished by any means known to the skilled artisan. Specific routes of administration include but are not limited to oral, transdermal (e.g., via a patch), parenteral injection (subcutaneous, intradermal, intramuscular, intravenous, intraperitoneal, intrathecal, etc.), or mucosal (intranasal, intratracheal, inhalation, intrarectal, intravaginal, etc.). An injection can be in a bolus or a continuous infusion.

For example the pharmaceutical compositions according to the invention are often administered by intravenous, intramuscular, or other parenteral means, or by biolistic "gene-gun" application to the epidermis. They can also be administered by intranasal application, inhalation, topically, orally, or as implants, and even rectal or vaginal use is possible. Suitable liquid or solid pharmaceutical preparation forms are, for example, aqueous or saline solutions for injection or inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer R (1990) Science 249: 1527-33, which is incorporated herein by reference.

The concentration of compounds included in compositions used in the methods of the invention can range from about 1 nM to about 100 µM. Effective doses are believed to range from about 10 picomole/kg to about 100 micromole/kg.

The pharmaceutical compositions are preferably prepared and administered in dose units. Liquid dose units are vials or ampoules for injection or other parenteral administration. Solid dose units are tablets, capsules, powders, and suppositories. For treatment of a patient, depending on activity of the compound, manner of administration, purpose of the administration (i.e., prophylactic or therapeutic), nature and severity of the disorder, age and body weight of the patient, different doses may be necessary. The administration of a given dose can be carried out both by single administration in the form of an individual dose unit or else several smaller dose units. Repeated and multiple administration of doses at specific intervals of days, weeks, or months apart are also contemplated by the invention.

The compositions can be administered per se (neat) or in the form of a pharmaceutically acceptable salt. When used in medicine the salts should be pharmaceutically acceptable, but non-pharmaceutically acceptable salts can conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention optionally include an active ingredient and optionally a pharmaceutically-acceptable carrier. The term "pharmaceutically-acceptable carrier" means one or more compatible solid or liquid fillers, dilutants or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being comingled with the compounds of the present invention, and with each other, in a manner such that there is no interaction which would substantially impair the desired pharmaceutical efficiency.

Compositions suitable for parenteral administration conveniently include sterile aqueous preparations, which can be isotonic with the blood of the recipient. Among the acceptable vehicles and solvents are water, Ringer's solution, phosphate buffered saline, and isotonic sodium chloride solution. In addition, sterile, fixed oils are conventionally employed as a solvent or suspending medium. For this purpose any bland fixed mineral or non-mineral oil may be employed including synthetic mono- or diglycerides. In addition, fatty acids such as oleic acid find use in the preparation of injectables. Carrier formulations suitable for subcutaneous, intramuscular, intraperitoneal, intravenous, etc. administrations can be found in *Remington's Pharmaceutical Sciences*, Mack Publishing Company, Easton, Pa.

The compounds useful in the invention can be delivered in mixtures of more than two such compounds. A mixture can further include one or more adjuvants in addition to the combination of compounds.

A variety of administration routes is available. The particular mode selected will depend, of course, upon the particular compound selected, the age and general health status of the subject, the particular condition being treated, and the dosage required for therapeutic efficacy. The methods of this invention, generally speaking, can be practiced using any mode of administration that is medically acceptable, meaning any mode that produces effective levels of response without causing clinically unacceptable adverse effects. Preferred modes of administration are discussed above.

The compositions can conveniently be presented in unit dosage form and can be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di-and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) difflusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

The invention will be further described in the following examples, which do not limit the scope of the invention described in the claims.

EXAMPLES

Example 1

In Vitro Screening of a Library of Small Molecules for Inhibitors of Human TLR9

Candidate small molecules for initial screening were obtained from a commercially available library of 880 off-patent small molecules selected for structural diversity and proven bioavailability in humans (Prestwick Chemical Library). Human embryonic kidney HEK293 cells stably transfected with a human TLR9 (hTLR9) expression vector were incubated overnight in the presence of 50 nM CpG ODN 2006 (i.e., the $EC_{50}$ concentration of ODN 2006) and selected small molecule candidate compounds at different concentrations ranging from $5\times10^{-7}$ M to $5\times10^{-5}$ M. TLR9 activity was assayed in terms of induction of a 6× NF-κB-luciferase reporter construct cotransfected in the cells. Results were measured as fold induction over baseline luciferase activity measured in the absence of ODN 2006 and compared to fold induction over baseline in the presence of the $EC_{50}$ concentration of ODN 2006 alone. From this initial screening a number of small molecules were identified as lead compounds and were categorized by structure and activity. Additional screening was performed in like manner using additional small molecules selected from another library or specifically prepared for this purpose. Results of some of these assays are presented in FIG. 1 and in Tables 5-16.

The method is described in greater detail as follows. The cells for each individual cell clone (hTLR3-NFκB-293, hTLR7-NFκB-293, hTLR8-NFκB-293 and hTLR9-NFκB-293) were counted and seeded one day before the stimulation at $1.5\times10^4$ cells per well in 96-well cell culture plates. To become adherent the cells were incubated after seeding overnight at 37° C. in 5% $CO_2$ humidified air.

The screen for each compound was performed at the same time for all of the receptors TLR3, TLR7, TLR8 and TLR9. Up to fifteen test compounds, each assayed in duplicate at each of three different final concentrations (0.5 μg/ml, 5 μg/ml, and 50 μg/ml), were used for 16 h cell stimulation on a single multiwell culture plate. A 4× final concentration master plate was created to prepare the different test compounds before they were added to the cells.

Controls were added as duplicates individually for each cell clone on the cell culture plate. Positive controls were used as follows (final concentrations): 50 μg/ml poly(I:C) for hTLR3-NFκB-293; 8 μM resiquimod (R848) for hTLR7-NFκB-293; 30 μM R848 for hTLR8-NFκB-293; and 2.5 μM CpG-ODN 2006 for hTLR9-NFκB-293. Media alone was used as negative control. After addition of controls and small molecules, the cell clones were additionally stimulated with the $EC_{50}$ concentration of the appropriate receptor-specific ligand.

To calculate the baseline response to the $EC_{50}$ concentration of the appropriate receptor-specific ligand, wells H3 and H6 did not receive receptor-specific ligand. The mean value of wells H2 and H5 (each with cells and $EC_{50}$ concentration of the appropriate receptor-specific ligand) divided by the mean of wells H3 and H6 (each with cells alone) yielded the baseline response (i.e., fold induction of luciferase activity) to $EC_{50}$ concentration of the appropriate receptor-specific ligand.

After 16 h stimulation the supernatant was removed and the cells treated with lysis buffer and stored at −80° C. before measuring.

An agonist screen was performed in parallel with the antagonist screen just described. The procedure was comparable to the antagonist screen except there was no addition of $EC_{50}$ concentration of receptor-specific ligand. The outcome of this screen reflected agonistic and toxicity effects.

Graphical Ranking System

For each screen result a graphical documentation was performed. A numerical score, describing the graphical results, was determined for each compound. For positive compounds either for antagonists or agonists or synergists the screen has been repeated at least twice.

Antagonists

The baseline result (measured with addition of the $EC_{50}$ concentration of the receptor-specific ligand) for each cell culture plate was measured as described above. Antagonistic effects were measured by down regulation compared to the baseline. Antagonists were scored as follows:

I3: compounds for which there was clear down regulation at 0.5 μg/ml, 5 μg/ml, and 50 μg/ml;

I2: compounds for which there was clear down regulation at 5 μg/ml and 50 μg/ml;

I1: compounds for which there was clear down regulation only at 50 μg/ml;

—: compounds for which there was no clear down regulation even at 50 μg/ml.

Agonists

To detect agonist activity the cells were treated in the above described manner but without adding the $EC_{50}$ concentration of receptor-specific ligand after treatment of the cells with small molecules. Usually the baseline in the agonist screen is taken to be 1 because these cells have not been additionally stimulated with the $EC_{50}$ concentration of the receptor-specific ligand. Agonist activity was present when there was above-baseline activity.

Agonists were scored as follows:

For compounds with highest agonist activity at 0.5 μg/ml,

−1: compounds for which there was a greater than 5-fold induction compared to baseline;

−2: compounds for which there was a 2- to 5-fold induction compared to baseline;

−3: compounds for which there was a less than 2-fold induction compared to baseline.

For compounds with highest agonist activity at 5 μg/ml, 0.25: compounds for which there was a greater than 5-fold induction compared to baseline;

0.5: compounds for which there was a 2- to 5-fold induction compared to baseline;

0.75: compounds for which there was a less than 2-fold induction compared to baseline.

For compounds with highest agonist activity at 50 μg/ml,

1: compounds for which there was a greater than 5-fold induction compared to baseline;

2: compounds for which there was a 2- to 5-fold induction compared to baseline;

3: compounds for which there was a less than 2-fold induction compared to baseline.

Toxicity

Measuring of "toxicity" of the small molecules was performed by analysing below-baseline activity within the agonist screen. "Toxicity" can have different explanations—either differences between the cell clones, the compound are effecting the signal transduction pathway or the TLR within the cell clone, or the compounds do really have a toxic effect on the cells.

Each compound was screened for "toxicity" on each of the four cell lines. Usually the baseline in the agonist screen is taken to be 1 because these cells have not been additionally stimulated with the $EC_{50}$ concentration of the receptor-specific ligand. Apparent toxicity was scored as follows:

T3: compounds for which there was clear down regulation at 0.5 μg/ml, 5 μg/ml, and 50 μg/ml;

T2: compounds for which there was clear down regulation at 5 μg/ml and 50 μg/ml;

T1: compounds for which there was clear down regulation only at 50 μg/ml.

Example 2

In Vitro Screening of a Library of Small Molecules for Inhibitors of Human TLR8

Candidate small molecules for initial screening were identified in an assay similar to that in Example 1 except HEK293 cells were stably transfected with a human TLR8 (hTLR8) expression vector and incubated overnight in the presence of 500 nM R848 ($EC_{50}$ of R848 for TLR8) and selected small molecule candidate compounds at different concentrations ranging from $5\times10^{-7}$ M to $5\times10^{-5}$ M. TLR8 activity was assayed in terms of induction of a 6× NF-κB-luciferase reporter construct cotransfected in the cells. Results were expressed as fold induction over baseline luciferase activity measured in the absence of R848. From this initial screening a number of small molecules were identified as lead compounds and were categorized by structure and activity. Additional screening was performed in like manner using additional small molecules selected from another library or specifically prepared for this purpose. Results of some of these assays are presented in Tables 5-16. Scoring is reported as above but as applied to TLR8.

Example 3

In Vitro Screening of a Library of Small Molecules for Inhibitors of Human TLR7

Candidate small molecules for initial screening were identified in an assay similar to that in Example 1 except HEK293 cells were stably transfected with a human TLR7 (hTLR7) expression vector and incubated overnight in the presence of 2 μM R848 ($EC_{50}$ of R848 for TLR7) and selected small molecule candidate compounds at different concentrations ranging from $5\times10^{-7}$ M to $5\times10^{-5}$ M. TLR7 activity was assayed in terms of induction of a 6× NF-κB-luciferase reporter construct cotransfected in the cells. Results were expressed as fold induction over baseline luciferase activity measured in the absence of R848. From this initial screening a number of small molecules were identified as lead compounds and were categorized by structure and activity. Additional screening was performed in like manner using additional small molecules selected from another library or specifically prepared for this purpose. Results of some of these assays are presented in Tables 5-16. Scoring is reported as above but as applied to TLR7.

Example 4

In Vitro Screening of a Library of Small Molecules for Inhibitors of Human TLR3

Candidate small molecules for initial screening were identified in an assay similar to that in Example 1 except HEK293 cells were stably transfected with a human TLR3 (hTLR3) expression vector and incubated overnight in the presence of 2.5 μg/ml poly(I:C) ($EC_{50}$ of poly(I:C) for TLR3) and selected small molecule candidate compounds at different concentrations ranging from $5 \times 10^{-7}$ M to $5 \times 10^{-5}$ M. TLR3 activity was assayed in terms of induction of a 6× NF-κB-luciferase reporter construct cotransfected in the cells. Results were expressed as fold induction over baseline luciferase activity measured in the absence of poly(I:C). From this initial screening a number of small molecules were identified as lead compounds and were categorized by structure and activity. Additional screening was performed in like manner using additional small molecules selected from another library or specifically prepared for this purpose. Results of some of these assays are presented in Tables 5-16. Scoring is reported as above but as applied to TLR3.

In the data presented in Tables 5-17 below, it should be recognized that at least certain compounds can conform to more than a single Formula.

TABLE 5

Exemplary Compounds of Formula II and Their Inhibitory Effect on Select TLRs

| ID | structure |
|---|---|
| 564 | *Chiral structure* |
| 904 | *structure* |
| 614 | *structure* |
| 613 | *structure* |

TABLE 5-continued
Exemplary Compounds of Formula II and Their Inhibitory Effect on Select TLRs
455 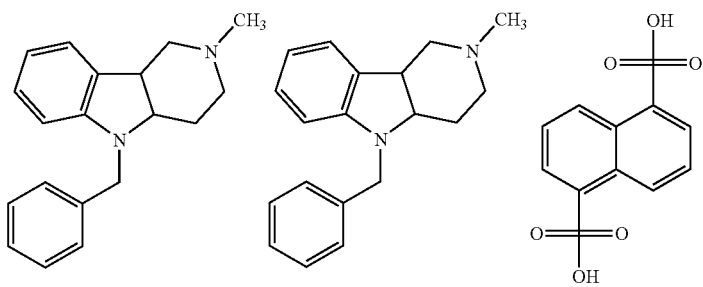
568 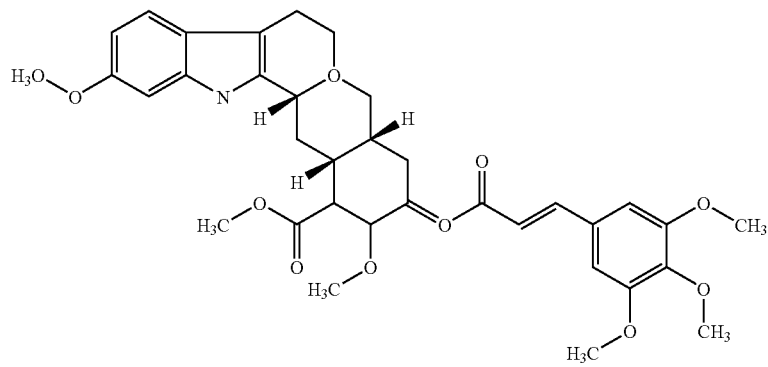
619 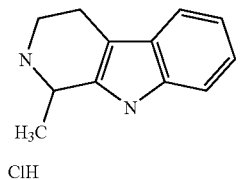
ClH
620 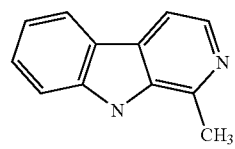
ClH
621 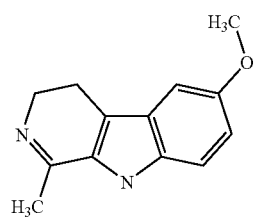

TABLE 5-continued
Exemplary Compounds of Formula II and Their Inhibitory Effect on Select TLRs
875
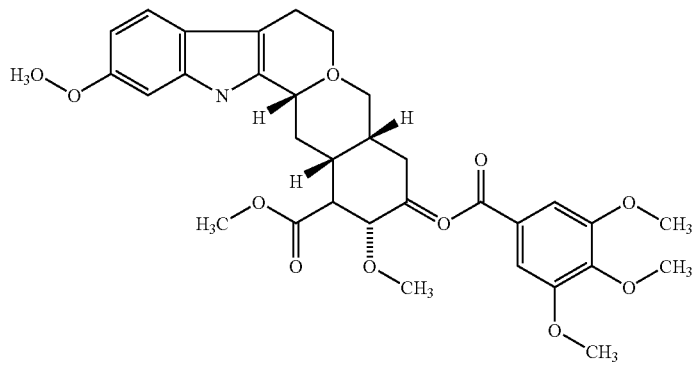
878
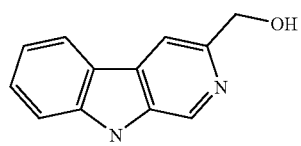
612
1050
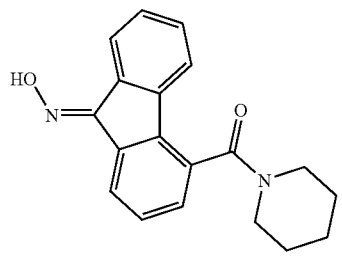
685
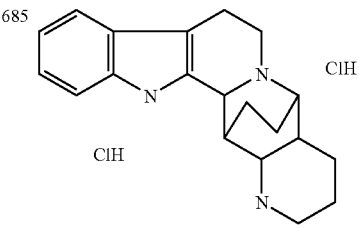
593 Chiral
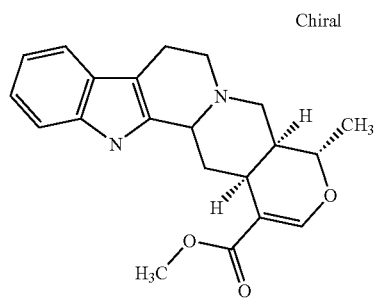

TABLE 5-continued
Exemplary Compounds of Formula II and Their Inhibitory Effect on Select TLRs
939
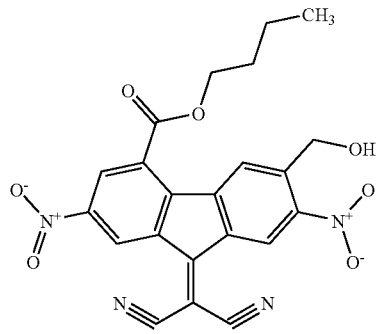
470
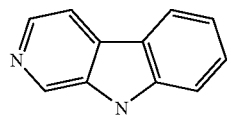
1039
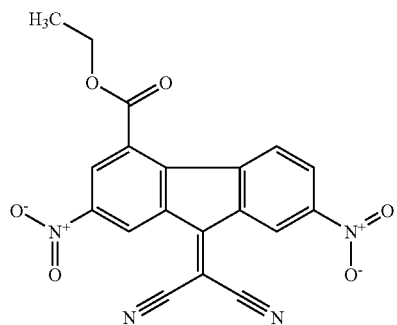
636    Chiral
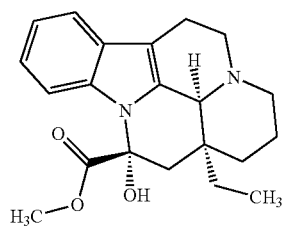
1241
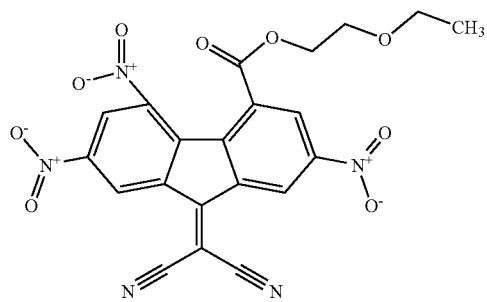

TABLE 5-continued

Exemplary Compounds of Formula II and Their Inhibitory Effect on Select TLRs

607 Chiral

918

944

890

1132

1243

| ID | chemical name | hTLR3 | hTLR7 | hTLR8 | hTLR9 |
|---|---|---|---|---|---|
| 564 | Syrosingopine | 13 | 11 | 12 | 13 |
| 904 | | 12 | 12 | 13 | 13 |
| 614 | Ellipticine | 12 | 13 | 11 | 13 |
| 613 | Harmine hydrochloride | 12 | 13 | 13 | 13 |
| 455 | Mebhydroline 1,5 naphtalenedisulfonate | — | — | — | 12 |
| 568 | Rescinnamin | — | — | — | 12 |
| 619 | Eleagnine hydrochloride (R,S) | — | — | — | 12 |
| 620 | Harmane hydrochloride | — | — | — | 12 |

TABLE 5-continued

Exemplary Compounds of Formula II and Their Inhibitory Effect on Select TLRs

| | | | | | |
|---|---|---|---|---|---|
| 621 | Methoxy-6-harmalan | — | — | — | 12 |
| 875 | Reserpine | — | — | — | 12 |
| 878 | 3-Hydroxymethyl-beta-carboline | — | — | — | 12 |
| 612 | Harmol hydrochloride monohydrate | 11 | 11 | 11 | 12 |
| 1050 | | 12 | 12 | 11 | 12 |
| 685 | Nitrarine dihydorchloride | — | — | — | 11 |
| 593 | Tetrahydroalstonine | — | 11 | — | 11 |
| 939 | | 11 | 11 | — | 11 |
| 470 | Norharman | 11 | 11 | 11 | 11 |
| 1039 | | — | 11 | 11 | 11 |
| 636 | Epivincamine | 11 | — | — | — |
| 1241 | | 11 | — | — | — |
| 607 | Eburnamonine | — | 11 | — | — |
| 918 | | — | 11 | — | — |
| 944 | | 11 | 11 | — | — |
| 890 | | — | 11 | 11 | — |
| 1132 | | 11 | 11 | 11 | — |
| 1243 | | — | 11 | 11 | — |

TABLE 6

Exemplary Compounds of Formula III and Their Inhibitory Effect on Select TLRs

| ID | structure | chemical name | hTLR3 | hTLR7 | hTLR8 | hTLR9 |
|---|---|---|---|---|---|---|
| 149 | 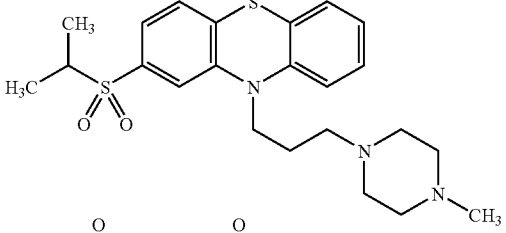 | Thioproperasine dimesylate | — | — | — | 13 |
| 53 | 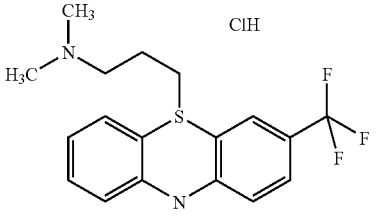 | Triflupromazine hydrochloride | 11 | 11 | 11 | 13 |
| 576 | 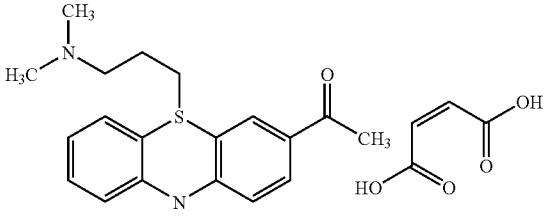 | Acetopromazine maleate salt | 11 | — | — | 12 |

TABLE 6-continued

Exemplary Compounds of Formula III and Their Inhibitory Effect on Select TLRs

| ID | structure | chemical name | hTLR3 | hTLR7 | hTLR8 | hTLR9 |
|---|---|---|---|---|---|---|
| 64 | 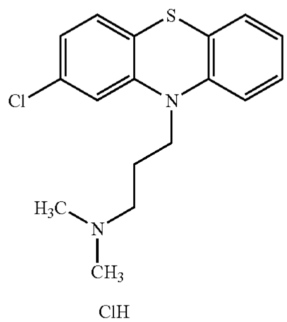 | Chlorpromazine hydrochloride | 11 | 11 | 11 | 12 |
| 693 | 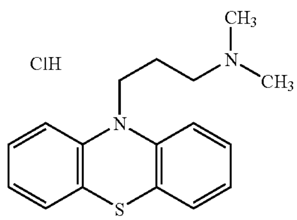 | Promazine hydrochloride | — | 12 | — | 12 |
| 399 | 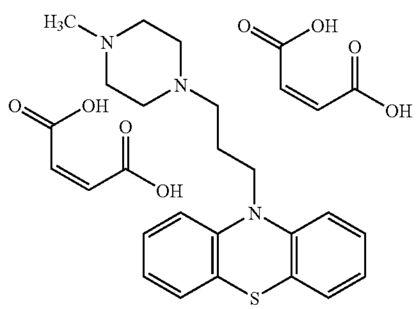 | Prochlorperazine dimaleate | 12 | 12 | 11 | 12 |
| 529 | 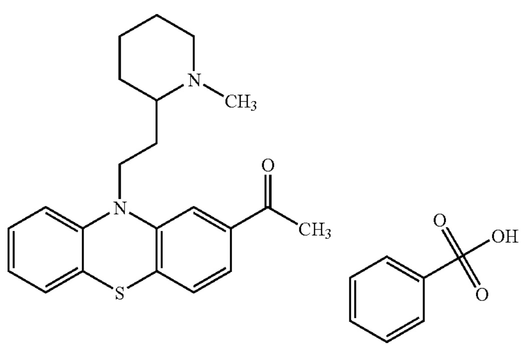 | Mesoridazine besylate | — | — | — | 11 |
| 125 | 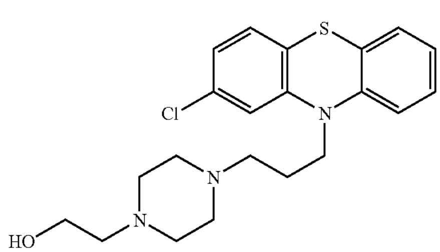 | Perphenazine | — | — | 11 | 11 |

TABLE 6-continued
Exemplary Compounds of Formula III and Their Inhibitory Effect on Select TLRs
| ID | structure | chemical name | hTLR3 | hTLR7 | hTLR8 | hTLR9 |
|---|---|---|---|---|---|---|
| 840 | 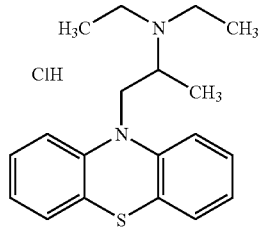 | Ethopropazine hydrochloride | — | — | 11 | 11 |
| 797 | 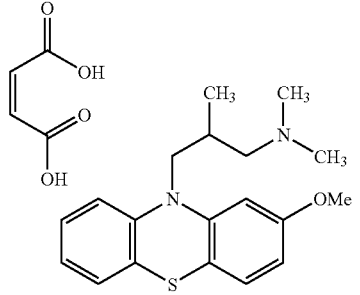 | Methotrimeprazine maleat salt | 11 | — | 11 | — |
| 313 | 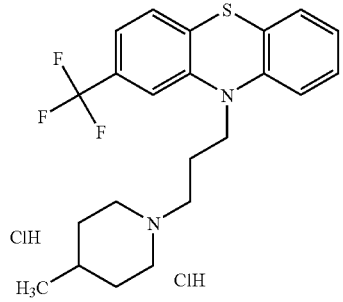 | Trifluoperazine dihydrochloride | — | 11 | 11 | 11 |
| 842 | 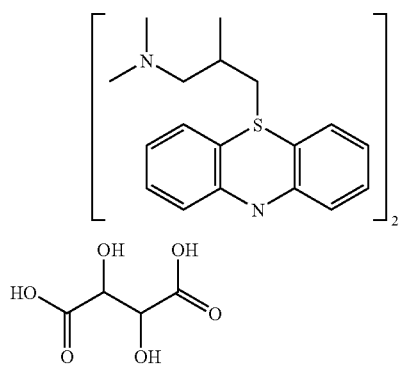 | Trimeprazine tartrate | — | — | 11 | — |

TABLE 7

Exemplary Compounds of Formula IV and Their Inhibitory Effect on Select TLRs

| ID | structure | chemical name | hTLR3 | hTLR7 | hTLR8 | hTLR9 |
|---|---|---|---|---|---|---|
| 413 | 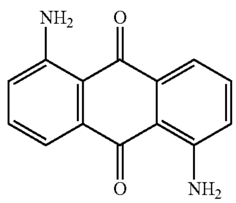 | Anthraquinone,1,5-diamino | 11 | — | 11 | 13 |
| 43 | 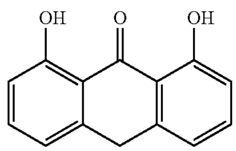 | Anthralin | — | — | 12 | 13 |
| 348 | 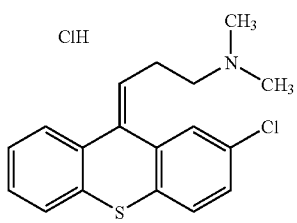 | Chlorprothixene hydrochloride | 11 | 11 | 11 | 12 |
| 491 | 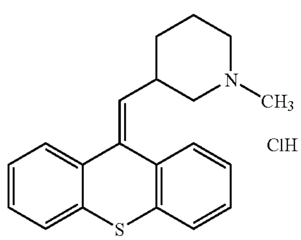 | Metixene hydrochloride | 12 | 11 | 11 | 12 |
| 1337 | 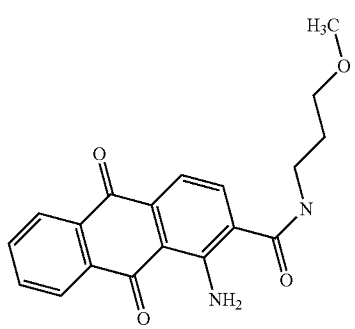 | | 11 | 11 | 11 | 12 |
| 1042 | 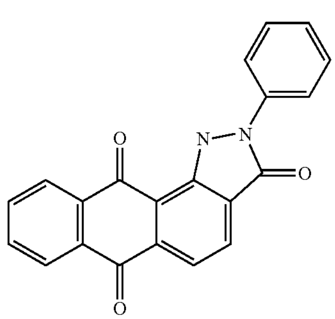 | | 11 | 12 | 13 | 12 |

TABLE 7-continued

Exemplary Compounds of Formula IV and Their Inhibitory Effect on Select TLRs

| ID | structure | chemical name | hTLR3 | hTLR7 | hTLR8 | hTLR9 |
|---|---|---|---|---|---|---|
| 1158 | 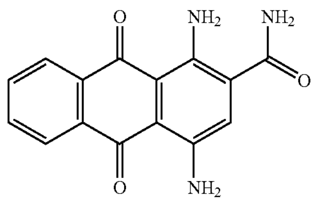 | | — | — | — | 11 |
| 1015 | 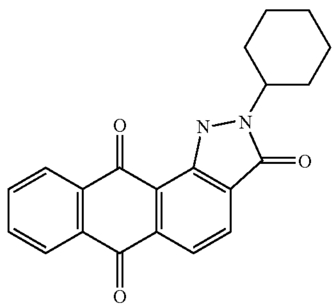 | | — | — | 11 | 11 |
| 1287 | 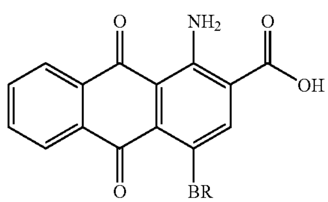 | | — | — | 11 | 11 |
| 294 | 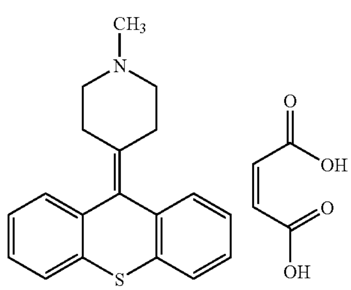 | Pimethixene maleate | 11 | 11 | 11 | 11 |
| 340 | 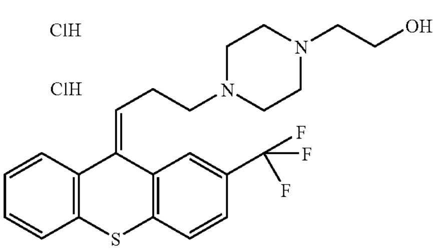 | Flupentixol dihydrochloride cis-(Z) | 11 | 11 | 11 | 11 |
| 346 | 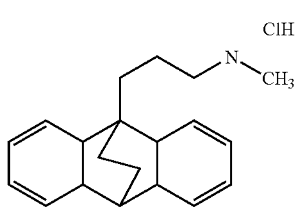 | Maprotiline hydrochloride | 11 | 11 | 11 | 11 |

TABLE 7-continued

Exemplary Compounds of Formula IV and Their Inhibitory Effect on Select TLRs

| ID | structure | chemical name | hTLR3 | hTLR7 | hTLR8 | hTLR9 |
|---|---|---|---|---|---|---|
| 917 | 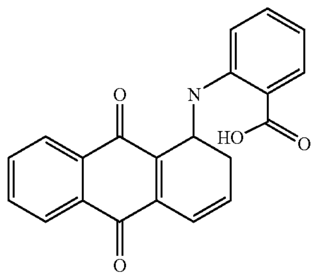 | | 12 | 11 | — | — |

TABLE 8

Exemplary Compounds of Formula V and Their Inhibitory Effect on Select TLRs

| ID | structure | chemical name | hTLR3 | hTLR7 | hTLR8 | hTLR9 |
|---|---|---|---|---|---|---|
| 72 | 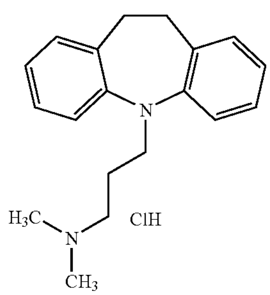 | Imipramine hydrochloride | — | — | — | 13 |
| 109 | 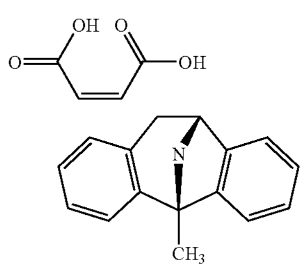 | Dizocilpine maleate | — | — | — | 13 |
| 488 | 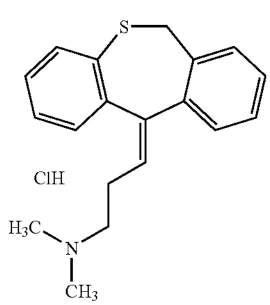 | Dosulepin hydrochloride | 11 | — | — | 12 |

TABLE 8-continued
Exemplary Compounds of Formula V and Their Inhibitory Effect on Select TLRs
| ID | structure | chemical name | hTLR3 | hTLR7 | hTLR8 | hTLR9 |
|---|---|---|---|---|---|---|
| 74 | 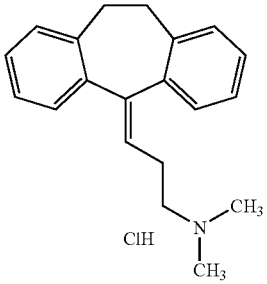 | Amitryptiline hydrochloride | — | 11 | — | 12 |
| 343 | 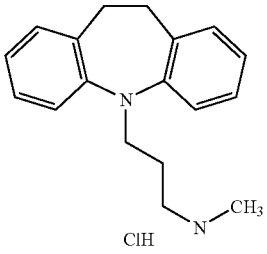 | Desipramine hydrochloride | 11 | 12 | 11 | 12 |
| 1013 | 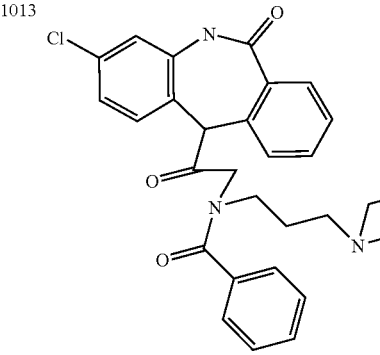 | | — | — | — | 11 |
| 1352 | 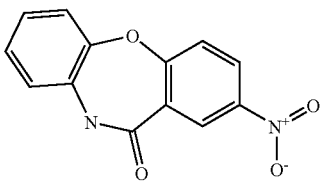 | | — | 13 | — | 11 |
| 99 | 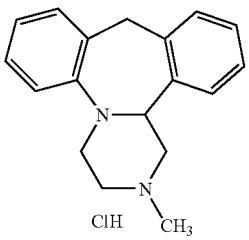 | Mianserine hydrochloride | 11 | — | — | — |

TABLE 9

Exemplary Compounds of Formula VI and Their Inhibitory Effect on Select TLRs

| ID | structure | chemical name | hTLR3 | hTLR7 | hTLR8 | hTLR9 |
|---|---|---|---|---|---|---|
| 239 | 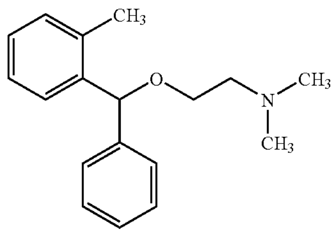 | Orphenadrine hydrochloride | — | — | — | 13 |
| 229 | 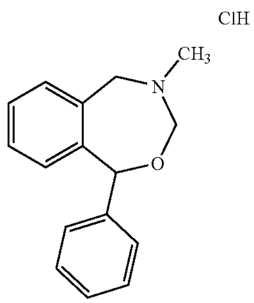 | Nefopam hydrochloride | — | — | — | 12 |
| 707 | 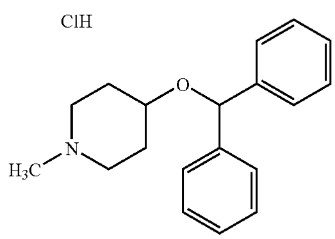 | Diphenylpyraline hydrochloride | — | 11 | — | 12 |
| 793 | 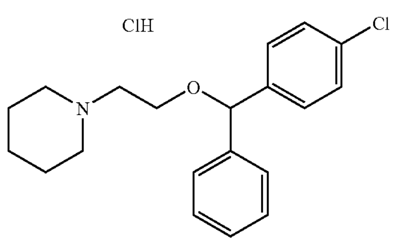 | Cloperastine hydrochloride | 11 | 11 | — | 12 |
| 957 | 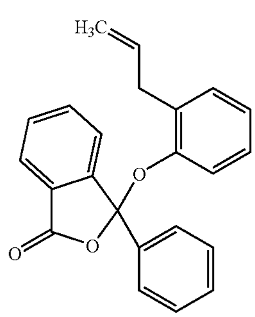 | | 12 | 11 | — | 12 |

TABLE 9-continued

Exemplary Compounds of Formula VI and Their Inhibitory Effect on Select TLRs

| ID | structure | chemical name | hTLR3 | hTLR7 | hTLR8 | hTLR9 |
|---|---|---|---|---|---|---|
| 1161 | 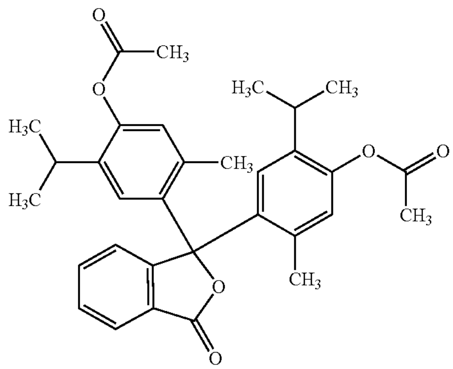 | | 12 | 12 | 12 | 12 |
| 65 | 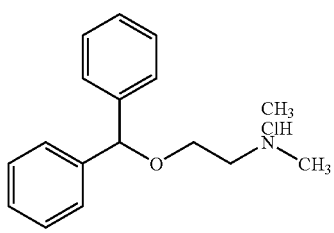 | Diphenhydramine hydrochloride | — | — | — | 11 |
| 970 | 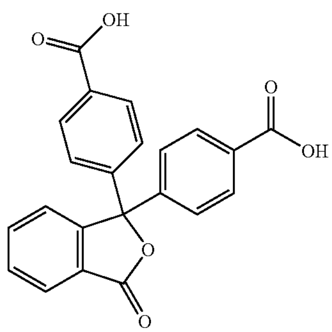 | | — | — | — | 11 |
| 306 | 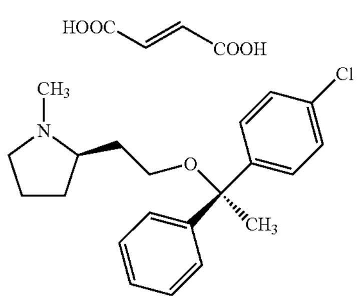 | Clemastine fumarate | 11 | 12 | 11 | 11 |
| 1308 | 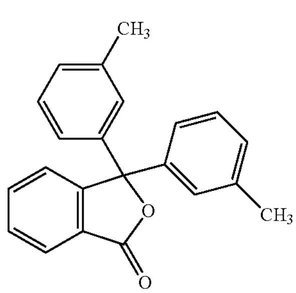 | | 12 | 12 | 12 | 11 |

TABLE 9-continued

Exemplary Compounds of Formula VI and Their Inhibitory Effect on Select TLRs

| ID | structure | chemical name | hTLR3 | hTLR7 | hTLR8 | hTLR9 |
|---|---|---|---|---|---|---|
| 974 | 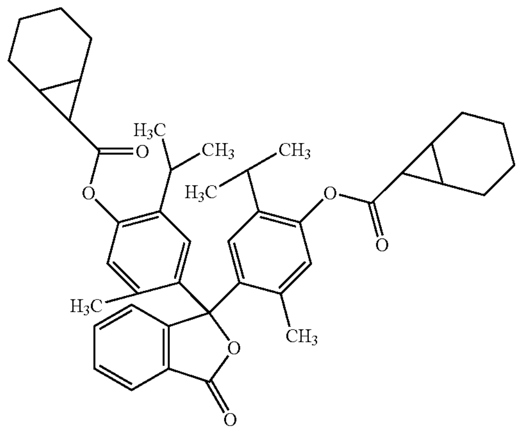 | | 11 | 11 | 11 | — |
| 386 | 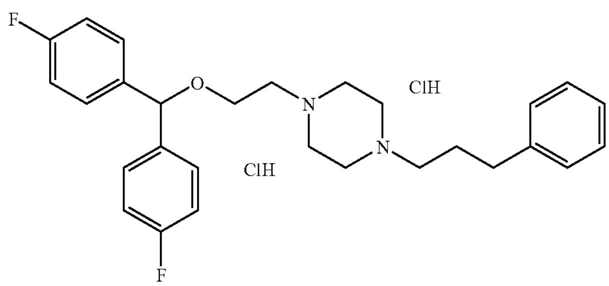 | GBR 12909 hydrochloride | 11 | 11 | 12 | — |

TABLE 10

Exemplary Compounds of Formula VII and Their Inhibitory Effect on Select TLRs

| ID | structure | chemical name | hTLR3 | hTLR7 | hTLR8 | hTLR9 |
|---|---|---|---|---|---|---|
| 312 | 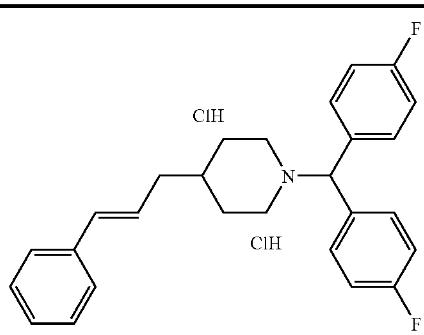 | Flunarizine hydrochloride | 11 | — | — | 12 |
| 457 | 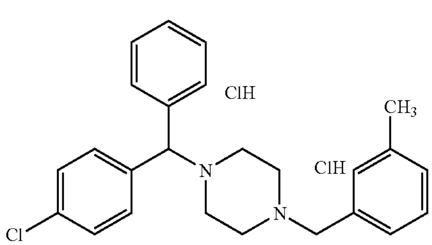 | Meclozine dihydrochloride | — | — | — | 11 |

TABLE 10-continued

Exemplary Compounds of Formula VII and Their Inhibitory Effect on Select TLRs

| ID | structure | chemical name | hTLR3 | hTLR7 | hTLR8 | hTLR9 |
|---|---|---|---|---|---|---|
| 510 | 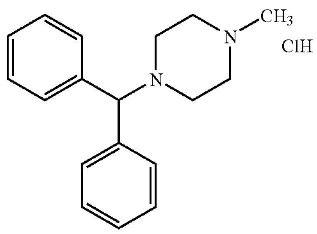 | Cyclizine hydrochloride | — | — | — | 11 |
| 133 | 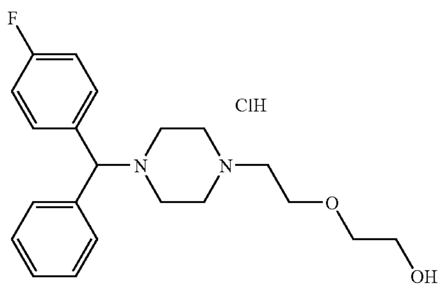 | Hydroxyzine dihydrochloride | 11 | 11 | — | 11 |
| 267 | 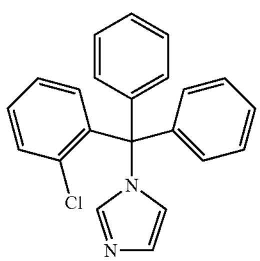 | Clotrimazole | — | 12 | 12 | — |

TABLE 11

Exemplary Compounds of Formula VIII and Their Inhibitory Effect on Select TLRs

| ID | structure | chemical name | hTLR3 | hTLR7 | hTLR8 | hTLR9 |
|---|---|---|---|---|---|---|
| 822 | 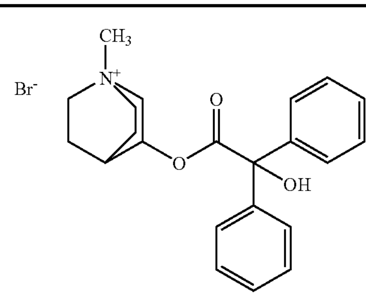 | Clidinium bromide | — | — | — | 12 |

TABLE 11-continued
Exemplary Compounds of Formula VIII and Their Inhibitory Effect on Select TLRs
| ID | structure | chemical name | hTLR3 | hTLR7 | hTLR8 | hTLR9 |
|---|---|---|---|---|---|---|
| 138 | 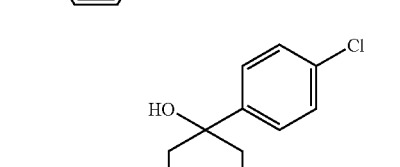 | Terfenadine | 11 | 11 | 11 | 12 |
| 144 | 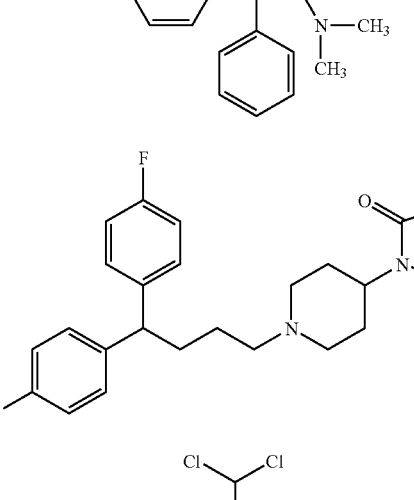 | Loperamide hydrochloride | 11 | 11 | 11 | 12 |
| 308 | 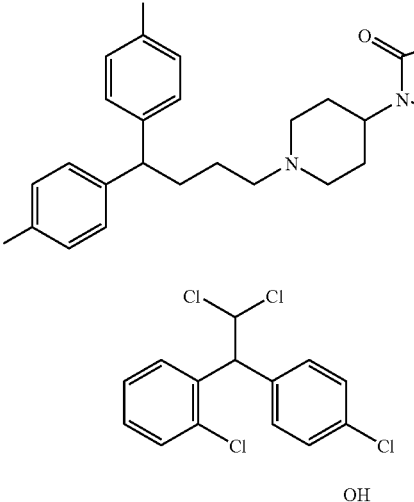 | Pimozide | 12 | 11 | 11 | 12 |
| 833 | 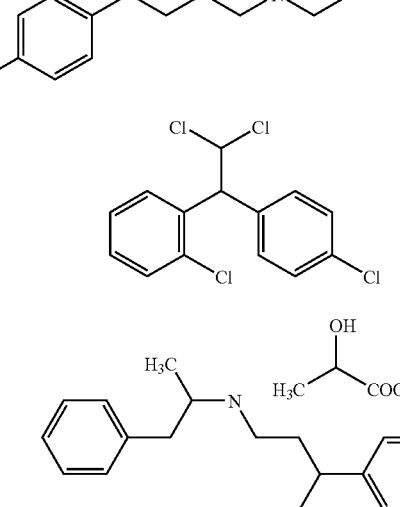 | Mitotane | 11 | 11 | 11 | 12 |
| 560 | 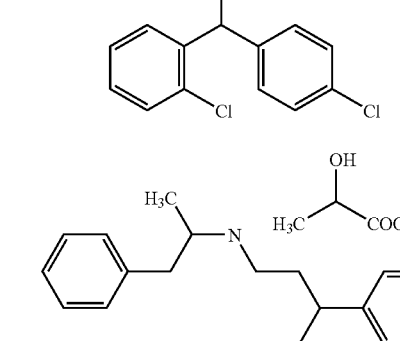 | Prenylamine lactate | — | 12 | — | 12 |

TABLE 11-continued
Exemplary Compounds of Formula VIII and Their Inhibitory Effect on Select TLRs
| ID | structure | chemical name | hTLR3 | hTLR7 | hTLR8 | hTLR9 |
|---|---|---|---|---|---|---|
| 93 | 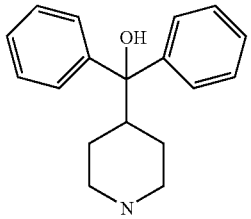 | Azacyclonol | — | — | — | 11 |
| 108 | 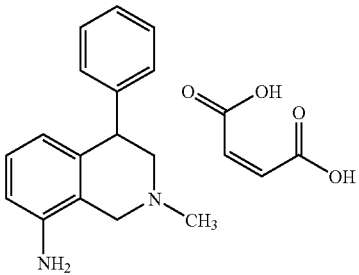 | Nomifensine maleate | — | — | — | 11 |
| 799 | 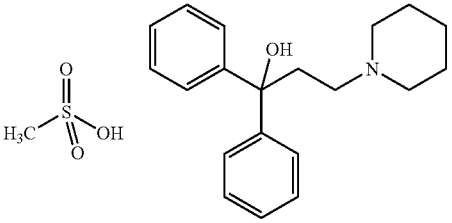 | Pridinol methanesulfonate salt | — | — | — | 11 |
| 381 | 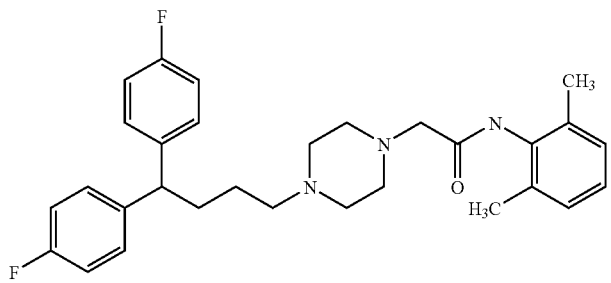 | Lidoflazine | 11 | 11 | 11 | 11 |
| 778 | 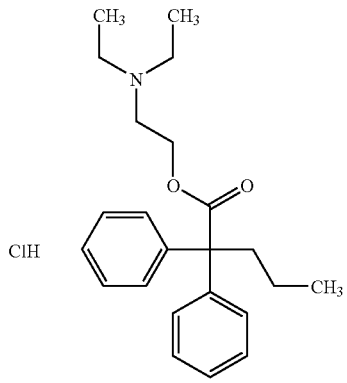 | Proadifen hydrochloride | 11 | 11 | 11 | 11 |

TABLE 11-continued

Exemplary Compounds of Formula VIII and Their Inhibitory Effect on Select TLRs

| ID | structure | chemical name | hTLR3 | hTLR7 | hTLR8 | hTLR9 |
|---|---|---|---|---|---|---|
| 884 | 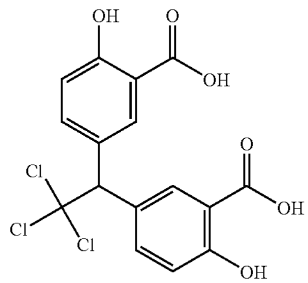 | | — | 11 | 11 | — |
| 270 | 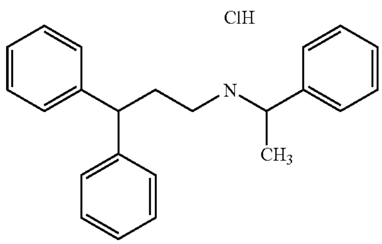 | Fendiline hydrochloride | 11 | 11 | 12 | — |
| 965 | 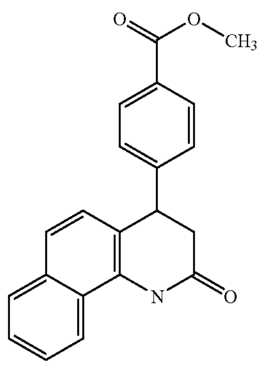 | | 12 | 12 | — | — |
| 1187 | 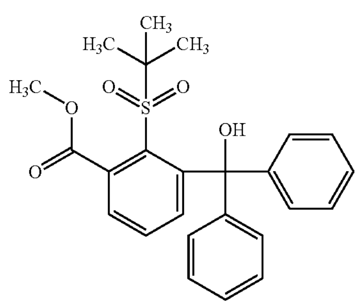 | | 12 | 12 | 11 | — |
| 267 | 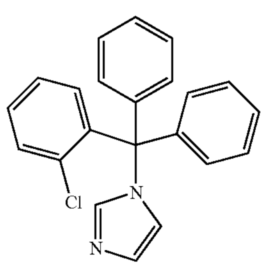 | Clotrimazole | — | 12 | 12 | — |

TABLE 12

Exemplary Compounds of Formula IX and Their Inhibitory Effect on Select TLRs

| ID | structure | chemical name | hTLR3 | hTLR7 | hTLR8 | hTLR9 |
|---|---|---|---|---|---|---|
| 751 | 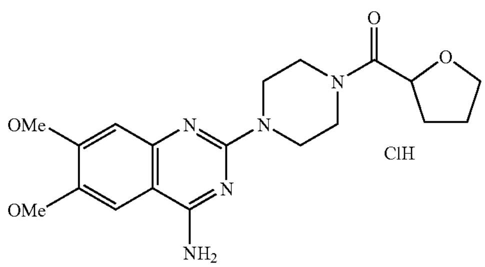 | Terazosin hydrochloride | — | — | — | 13 |
| 858 | 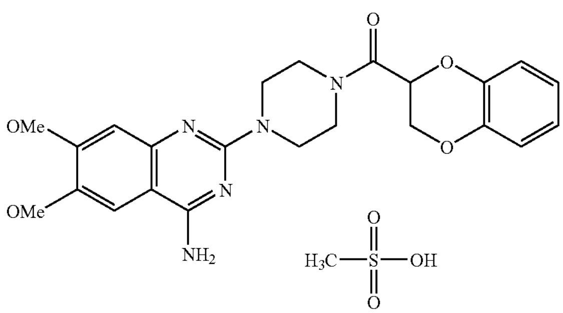 | Doxazosin mesylate | — | — | — | 13 |
| 2000 | 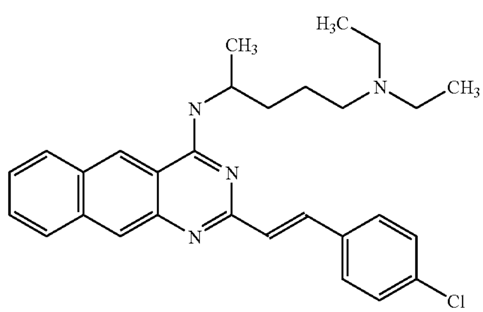 | | 12 | 13 | 11 | 13 |
| 2001 | 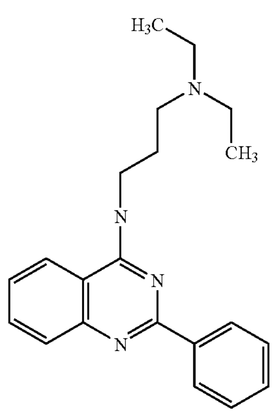 | | 11 | 11 | 0.75 | 13 |

TABLE 13

Exemplary Compounds of Formula X and Their Inhibitory Effect on Select TLRs

| ID | structure | chemical name | hTLR3 | hTLR7 | hTLR8 | hTLR9 |
|---|---|---|---|---|---|---|
| 431 | 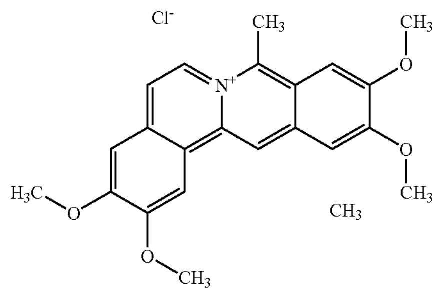 | Coralyne chloride hydrate | — | — | — | 13 |
| 792 | 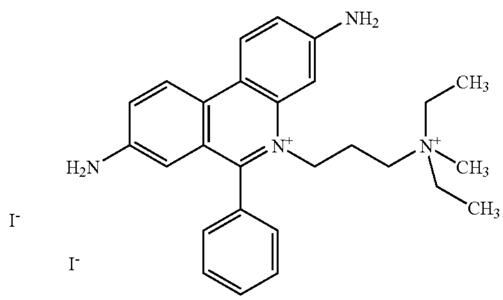 | Propidium iodide | 12 | — | — | 12 |
| 583 | 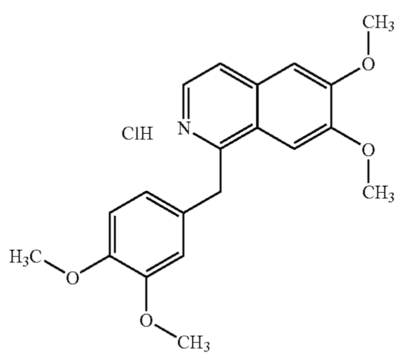 | Papaverine hydrochloride | — | 11 | — | 12 |
| 830 | 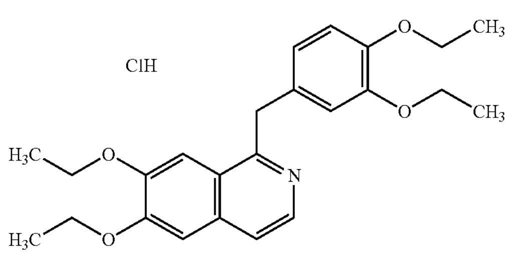 | Ethaverine hydrochloride | — | 11 | 11 | 11 |
| 586 | 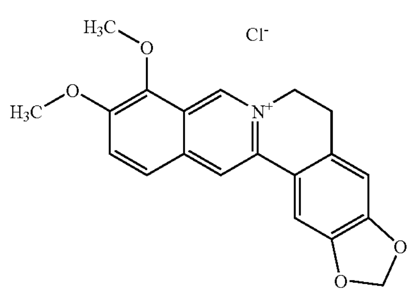 | Berberine chloride | 11 | — | 12 | — |

TABLE 14

Exemplary Compounds of Formula XI and Their Inhibitory Effect on Select TLRs

| ID | structure | chemical name | hTLR3 | hTLR7 | hTLR8 | hTLR9 |
|---|---|---|---|---|---|---|
| 1320 | 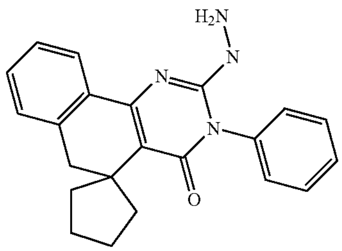 | | — | — | — | 13 |
| 891 | 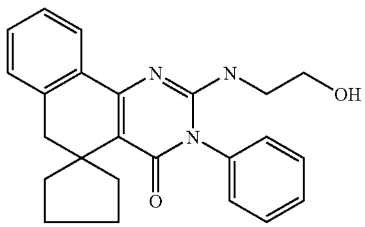 | | 11 | 11 | — | 11 |
| 926 | 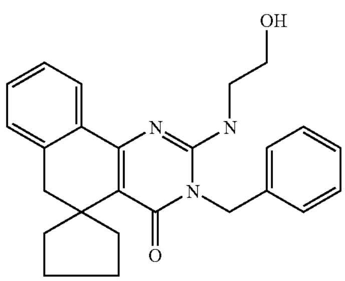 | | 12 | 11 | 11 | 11 |
| 1137 | 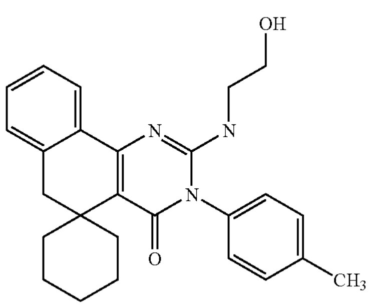 | | 13 | 12 | 11 | 11 |
| 1213 | 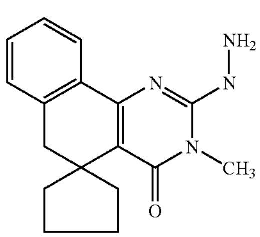 | | — | 11 | — | — |
| 1322 | 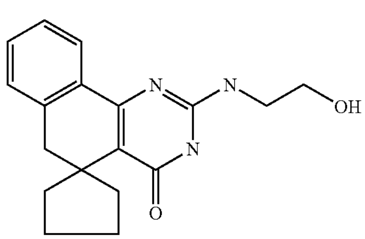 | | 11 | 11 | — | — |

TABLE 14-continued

Exemplary Compounds of Formula XI and Their Inhibitory Effect on Select TLRs

| ID | structure | chemical name | hTLR3 | hTLR7 | hTLR8 | hTLR9 |
|---|---|---|---|---|---|---|
| 1248 | 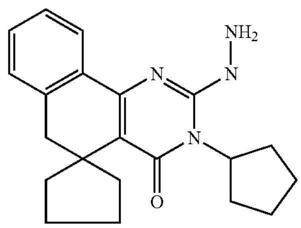 | | — | 11 | 11 | — |

TABLE 15

Exemplary Compounds of Formula XII and Their Inhibitory Effect on Select TLRs

| ID | structure | chemical name | hTLR3 | hTLR7 | hTLR8 | hTLR9 |
|---|---|---|---|---|---|---|
| 600 | 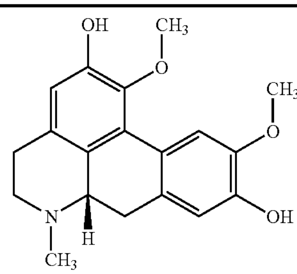 | Boldine | — | — | — | 12 |
| 101 | 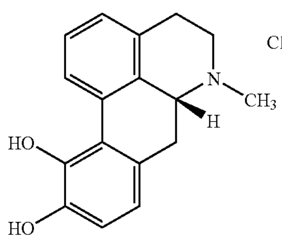 | Apomorphine hydrochloride (R, —) | — | — | 11 | 12 |
| 669 | 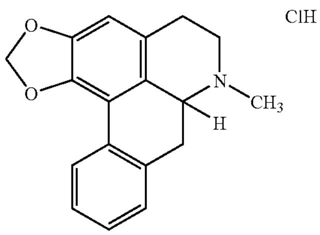 | Remerine hydrochloride | — | 11 | — | — |

TABLE 16

Exemplary Compounds of Formula XIII and Their Inhibitory Effect on Select TLRs

| ID | structure | chemical name | hTLR3 | hTLR7 | hTLR8 | hTLR9 |
|---|---|---|---|---|---|---|
| 990 | 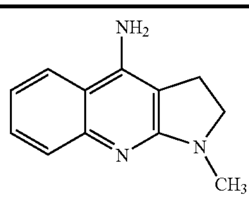 | | — | — | — | 13 |

TABLE 16-continued

Exemplary Compounds of Formula XIII and Their Inhibitory Effect on Select TLRs

| ID | structure | chemical name | hTLR3 | hTLR7 | hTLR8 | hTLR9 |
|---|---|---|---|---|---|---|
| 1185 | 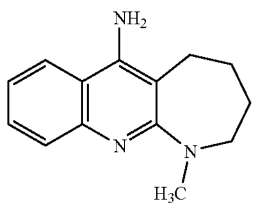 | | — | — | — | 13 |
| 1003 | 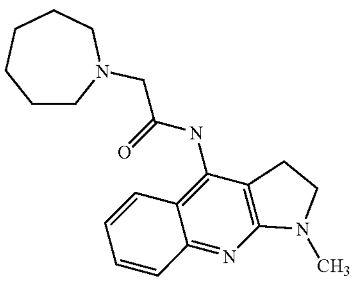 | | 11 | 11 | — | 13 |
| 1091 | 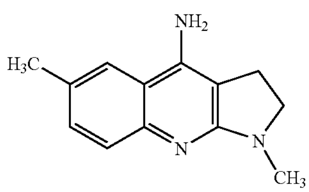 | | 11 | 11 | 11 | 13 |
| 1142 | 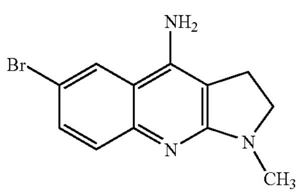 | | 11 | 11 | 11 | 13 |
| 1217 | 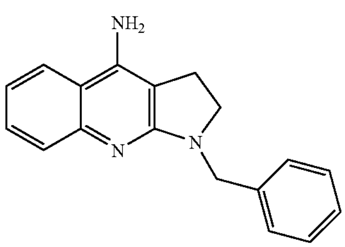 | | 12 | 13 | 11 | 13 |
| 1212 | 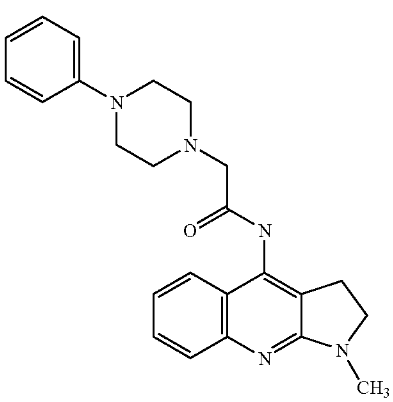 | | — | 11 | — | 12 |

TABLE 16-continued

Exemplary Compounds of Formula XIII and Their Inhibitory Effect on Select TLRs

| ID | structure | chemical name | hTLR3 | hTLR7 | hTLR8 | hTLR9 |
|---|---|---|---|---|---|---|
| 1244 | 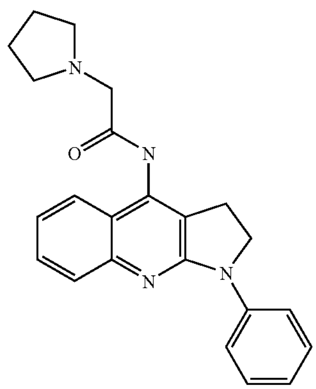 | | 11 | 11 | 11 | 12 |
| 1334 | 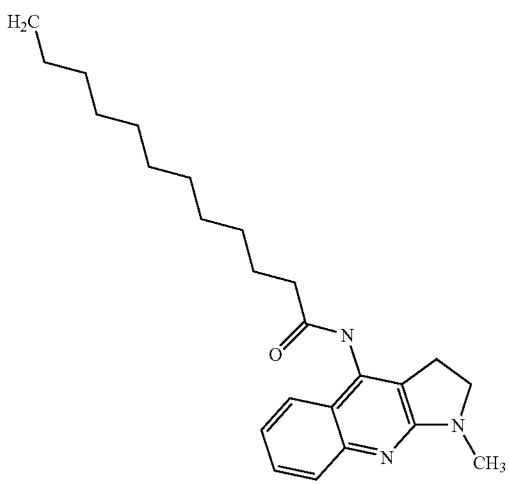 | | — | — | — | 11 |
| 1224 | 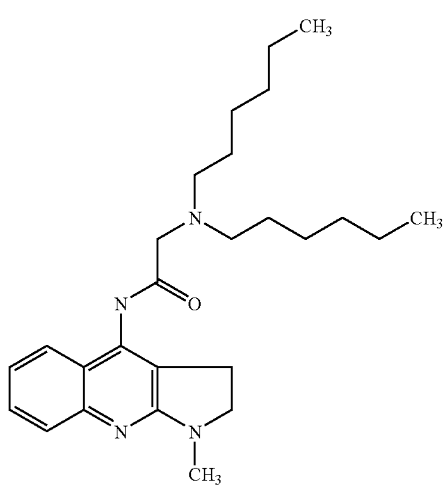 | | 12 | 12 | 12 | 11 |

TABLE 17

Exemplary Compounds of Formula XIV and Their Inhibitory Effect on Select TLRs

| ID | structure | chemical name | hTLR3 | hTLR7 | hTLR8 | hTLR9 |
|---|---|---|---|---|---|---|
| 807 | 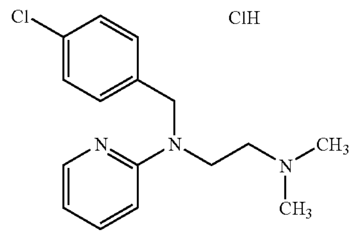 | Chloropyramine hydrochloride | — | — | — | 12 |
| 1163 | 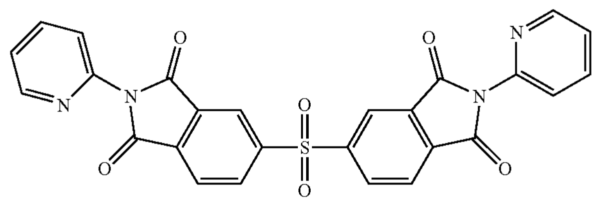 | | 11 | 11 | 11 | 11 |
| 1367 | 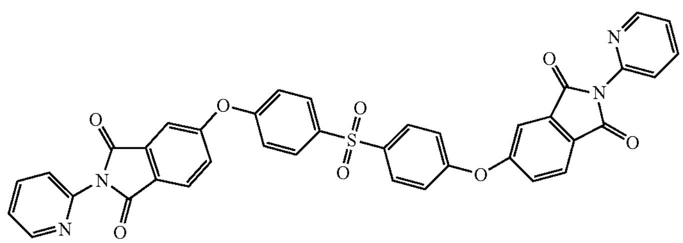 | | 12 | 11 | 11 | — |

Example 5

In Vivo Screening of Selected Small Molecules

Experimental mice are administered known amounts of candidate small molecules and a source of PAMP or other suitable TLR ligand, e.g., CpG nucleic acid. Negative control mice receive the source of PAMP or other suitable TLR ligand, e.g., CpG nucleic acid, alone. After an appropriate period, blood samples are obtained from control and experimental mice and evaluated for serum concentration of cytokine using a suitable method, e.g., enzyme-linked immunosorbent assay (ELISA). Alternatively or in addition, peripheral blood mononuclear cells (PBMC) are isolated from both groups of animals and assessed for expression of activation marker using a suitable technique such as fluorescence activated cell sorting (FACS). Control and experimental results are compared in pairwise fashion. Reduced expression of activation marker or reduced concentration of cytokine in an experimental animal compared to a negative control animal indicates the small molecule inhibits TLR-mediated signaling in response to a ligand for the TLR. Increased expression of activation marker or increased concentration of cytokine in an experimental animal compared to a negative control animal indicates the small molecule promotes TLR-mediated signaling in response to a ligand for the TLR.

Example 6

In Vivo Screening of Selected Small Molecules

Experimental mice are administered candidate small molecules. Negative control mice are administered carrier alone. After administration or small molecule or carrier alone, PBMC are isolated and then exposed in vitro to CpG nucleic acid under conditions in which the PBMC, in the absence of small molecule, are stimulated to express an activation marker such as CD86 or secrete a product such as cytokine (e.g., IFN-α, IL-6, TNF-α) or chemokine (e.g., IP-10). The expression of the activation marker or the secretion of the product is quantified using FACS, ELISA, or other suitable method, and comparison is made between results obtained with and without the small molecule. Reduced expression of activation marker or reduced concentration of cytokine in an experimental animal compared to a negative control animal indicates the small molecule inhibits TLR-mediated signaling in response to a ligand for the TLR. Increased expression of activation marker or increased concentration of cytokine in an experimental animal compared to a negative control animal indicates the small molecule promotes TLR-mediated signaling in response to a ligand for the TLR.

Example 7

Human TLR9 Antagonism by 4-Primary Amino Quinolines

Stably co-transfecting the human TLR9 receptor (hTLR9) and an NF-κB promoter-driven luciferase gene into HEK-293 cells created the cell line hTLR9-NFkB-293. hTLR9-NFkB-293 cells were counted and seeded at $1.5 \times 10^4$ cells per well in 96-well cell culture plates one day before assaying and cultured at 37° C./5% $CO_2$. The day of the assay, antagonist was added at 50 μM, 5.0 μM or 0.5 μM. The cells were then stimulated with the EC50 dose of the TLR9 agonist, CpG-ODN 2006, and cultured for 16 h in a humidified incubator at 37° C. The culture supernatant was removed and the cells were treated with lysis buffer and stored at −80° C. before measuring luciferase activity. The luciferase readout was measured according to manufacturer's instructions using a luciferase assay system available from Promega, USA. Results are summarized in Table 18. The antagonist dose listed in Table 18 is the minimum effective dose (μM) for blockade of the TLR9 agonist. As evident from the results presented in Table 18, the minimum effective dose (μM) for blockade of the TLR9 agonist was 0.5 μM or 5 μM for all of the compounds tested, as measured by this three-point assay.

TABLE 18

Human TLR9 Antagonism by 4-Amino-Quinolines.

| Compound number | structure | chemical name | antagonist dose |
| --- | --- | --- | --- |
| 936 | 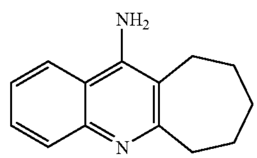 | 7,8,9,10-Tetrahydro-6H-cyclohepta[b]quinolin-11-ylamine | 0.5 μM |
| 990 (122) | 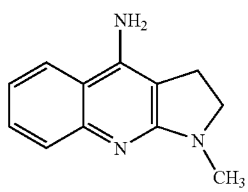 | 1-Methyl-2,3-dihydro-1H-pyrrolo[2,3-b]quinolin-4-ylamine | 0.5 μM |
| 1091 (123) | 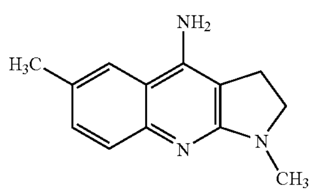 | 1,6-Dimethyl-2,3-dihydro-1H-pyrrolo[2,3-b]quinolin-4-ylamine | 0.5 μM |
| 1142 (124) | 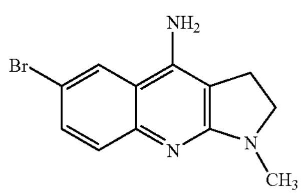 | 6-Bromo-1-methyl-2,3-dihydro-1H-pyrrolo[2,3-b]quinolin-4-ylamine | 0.5 μM |
| 1185 (125) | 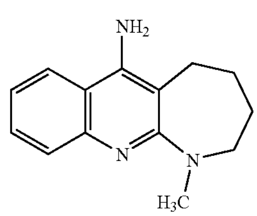 | 1-Methyl-2,3,4,5-tetrahydro-1H-azepino[2,3-b]quinolin-6-ylamine | 0.5 μM |
| 1201 | 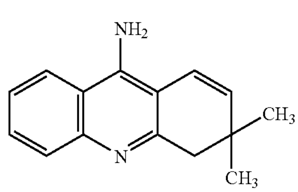 | 3,3-Dimethyl-3,4-dihydro-acridin-9-ylamine | 0.5 μM |

TABLE 18-continued

Human TLR9 Antagonism by 4-Amino-Quinolines.

| Compound number | structure | chemical name | antagonist dose |
|---|---|---|---|
| 1217 (126) | 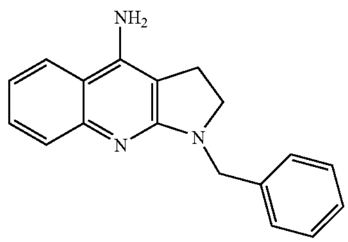 | 1-Benzyl-2,3-dihydro-1H-pyrrolo[2,3-b]quinolin-4-ylamine | 0.5 μM |
| 1552 (127) | 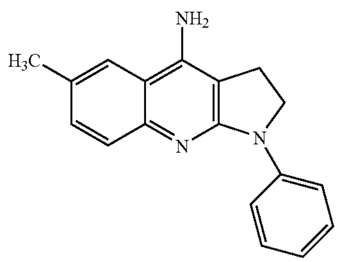 | 6-Methyl-1-phenyl-2,3-dihydro-1H-pyrrolo[2,3-b]quinolin-4-ylamine | 0.5 μM |
| 1553 (128) | 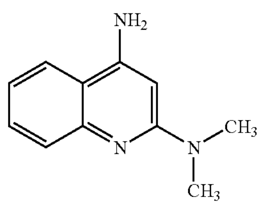 | N*2*,N*2*-Dimethyl-quinoline-2,4-diamine | 0.5 μM |
| 1595 | 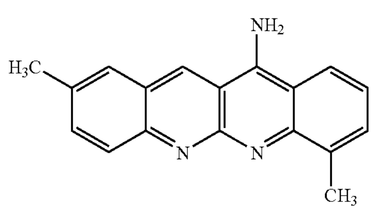 | 2,7-Dimethyl-dibenzo[b,g][1,8]naphthyridin-11-ylamine | 0.5 μM |
| 1690 | 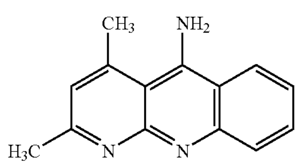 | 2,4-Dimethyl-benzo[b][1,8]naphthyridin-5-ylamine | 0.5 μM |
| 1727 | 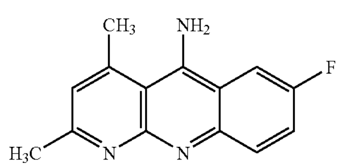 | 7-Fluoro-2,4-dimethyl-benzo[b][1,8]naphthyridin-5-ylamine | 0.5 μM |
| 329 | 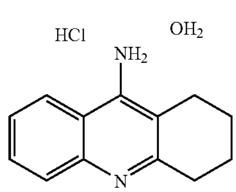 | 1,2,3,4-Tetrahydro-acridin-9-ylamine Tacrine hydrochloride hydrate | 5.0 μM |

TABLE 18-continued

Human TLR9 Antagonism by 4-Amino-Quinolines.

| Compound number | structure | chemical name | antagonist dose |
|---|---|---|---|
| 1061 | 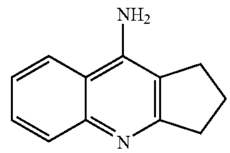 | 2,3-Dihydro-1H-cyclopenta[b]quinolin-9-ylamine | 5.0 μM |
| 1227 | 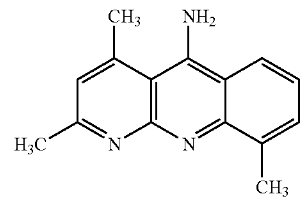 | 2,4,9-Trimethyl-benzo[b][1,8]naphthyridin-5-ylamine | 5.0 μM |
| 1286 | 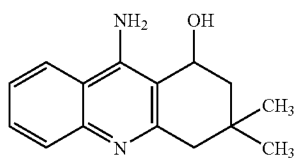 | 9-Amino-3,3-dimethyl-1,2,3,4-tetrahydro-acridin-1-ol | 5.0 μM |
| 1674 | 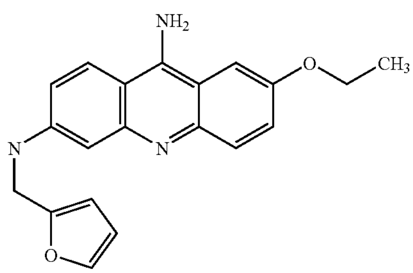 | 7-Ethoxy-N*3*-furan-2-ylmethyl-acridine-3,9-diamine | 5.0 μM |

Example 8

Human TLR9 Antagonism by Quinazolines hTLR9-NFkB-293 cells were counted and seeded at $1.5\times 10^4$ cells per well in 96-well cell culture plates one day before assaying and cultured at 37° C./5% $CO_2$, as described in Example 7. The day of the assay, antagonist was added at varying concentrations starting at 50 μM with a 1/5 to 1/6 dilution for 7 steps. The cells were then stimulated with the EC50 dose of the TLR9 agonist, CpG-ODN 2006, and cultured for 16 h in a humidified incubator at 37° C. The culture supernatant was removed and the cells were treated with lysis buffer and stored at −80° C. before measuring luciferase activity as described in Example 7. Sigmoidal antagonism curves were generated and the inhibitor concentration at which 50% of the agonist response was blocked (IC50) calculated. Results shown in Table 19 under the heading hTLR9 are the IC50 dose (μM) for blockade of a CpG ODN-generated signal in hTLR9-NFkB-293 cells.

Alternatively, TLR9 ligand antagonism in human peripheral blood mononuclear cells (PBMC) was monitored. Peripheral blood buffy coat preparations from healthy male and female human donors were obtained from the Blood Bank of the University of Düsseldorf (Germany) and from these, PBMC were purified by centrifugation over Ficoll-Hypaque (Sigma). The purified PBMC were resuspended in RPMI 1640 culture medium supplemented with 5% (v/v) heat-inactivated human AB serum (Bio Whittaker, Belgium) or 10% (v/v) heat-inactivated fetal calf serum (FCS), 1.5 mM L-glutamine, 100 U/ml penicillin and 100 μg/ml streptomycin (all from Sigma). Fresh PBMC at a concentration of $3\times 10^6$/ml to $5\times 10^6$/ml were added to 96-well round-bottomed plates (150 μl/well). After cell plating, antagonist was added at varying concentrations starting at 50 μM with a 1/5 to 1/6 dilution for 7 steps. The cells were then stimulated with the TLR9 agonist, CpG-ODN 2006, and cultured for 16 h in a humidified incubator at 37° C. Culture supernatants were collected and, if not used immediately, frozen at −20° C. until required. Interleukin 6 (IL-6) in the supernatants was quantitatively assessed using commercially available ELISA Kits (IL6, Diaclone, USA). Sigmoidal antagonism curves were generated and IC50 calculated. Results shown in Table 19 under the heading IL-6 are the IC50 dose (μM) for blockade of CpG ODN-generated IL-6 production by human PBMC.

//
TABLE 19

Antagonism of TLR9 Signal Agonist CpG ODN 2006 by Quinazolines

| Compound number | Structure | Chemical name | hTLR9 | IL-6 |
|---|---|---|---|---|
| CMZ 203-34 (201) | 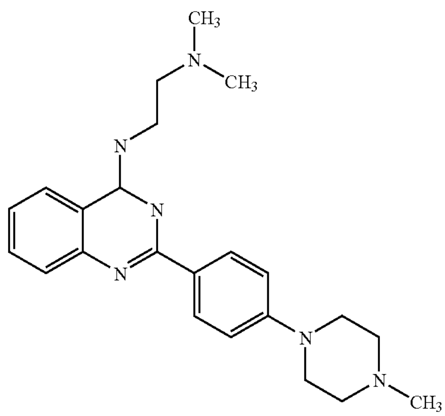 | N,N-dimethyl-N'-{2-[4-(4-methyl-piperazin-1-yl)-phenyl]-3,4-dihydro-quinazoline-4-yl}-ethane-1,2,-diamine | 0.003 | 0.05 |
| CMZ 203-78 | 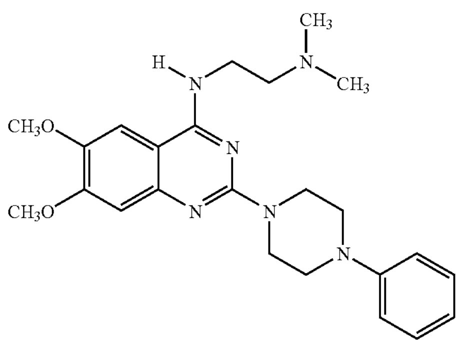 | N'-[6,7-Dimethoxy-2-(4-phenyl-piperazin-1-yl)-quinazolin-4-yl]-N,N-dimethyl-ethane-1,2-diamine | 0.003 | 0.008 |
| CMZ 203-76 | 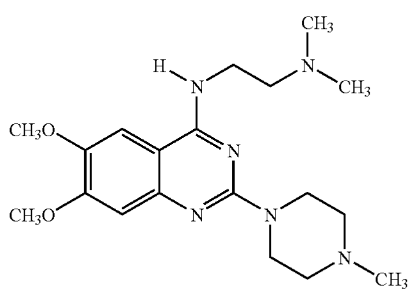 | N'-[6,7-Dimethoxy-2-(4-methyl-piperazin-1-yl)-quinazolin-4-yl]-N,N-dimethyl-ethane-1,2-diamine | 0.003 | 0.221 |
| CMZ 203-87 | 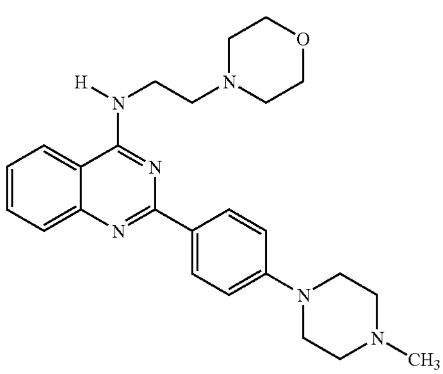 | | 0.02 | ND |

TABLE 19-continued

Antagonism of TLR9 Signal Agonist CpG ODN 2006 by Quinazolines

| Compound number | Structure | Chemical name | hTLR9 | IL-6 |
|---|---|---|---|---|
| CMZ 203-44 | 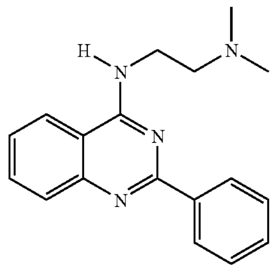 | N,N-Dimethyl-N'-(2-phenyl-quinazolin-4-yl)-ethane-1,2-diamine | 2.4 | 4.0 |
| CMZ 203-49 (213) | 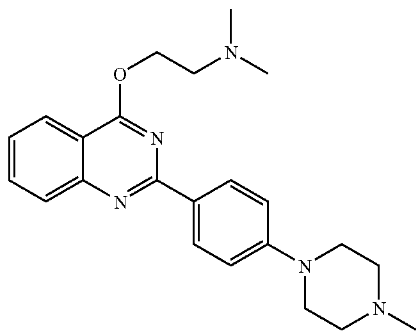 | Dimethyl-(2-{2-[4-(4-methyl-piperazin-1-yl)-phenyl]-quinazolin-4-yloxy}-ethyl)-amine | 2.4 | 0.6 |
| CMZ 203-51 | 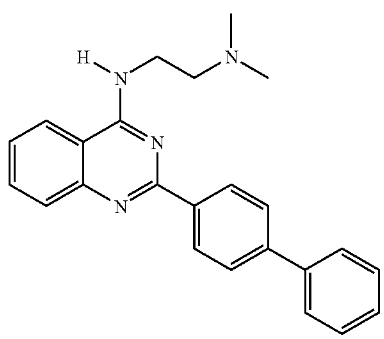 | N'-(2-Biphenyl-4-yl-quinazolin-4-yl)-N,N-dimethyl-ethane-1,2-diamine | 5.2 | 6.6 |
| CMZ 203-90 | 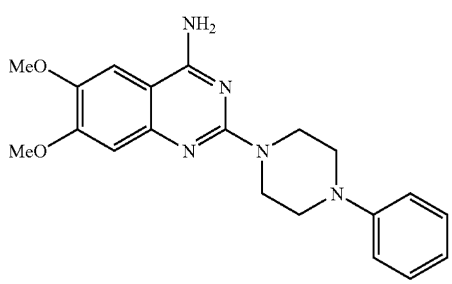 | | 5.43 | ND |
| CMZ 203-45 | 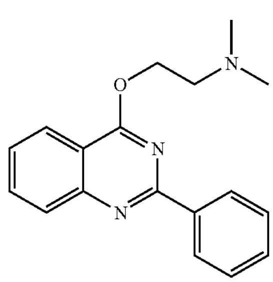 | Dimethyl-[2-(2-phenyl-quinazolin-4-yloxy)-ethyl]-amine | 29 | ND |

TABLE 19-continued

Antagonism of TLR9 Signal Agonist CpG ODN 2006 by Quinazolines

| Compound number | Structure | Chemical name | hTLR9 | IL-6 |
|---|---|---|---|---|
| CMZ 203-93 | 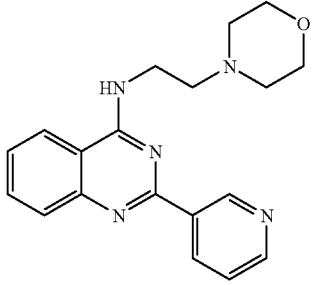 | | ND | ND |
| CMZ 203-95 | 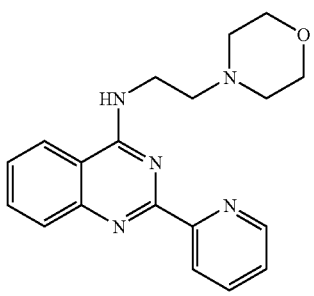 | | ND | ND |

ND: No Data.

Example 9

Reduced In Vivo Toxicity of Quinazoline Compounds Compared with a Structurally Similar Quinoline Female BALB/c mice (n=3 per group) were given a single intraperitoneal bolus injection of CMZ 203-43 (1.0 or 4.0 mg), CMZ 203-34 (1.0 or 4.0 mg) or CMZ 203-49 (1.0 or 4.0 mg) in a volume of 0.2 ml. Compound CMZ 203-43 has the structural formula

CMZ 203-43

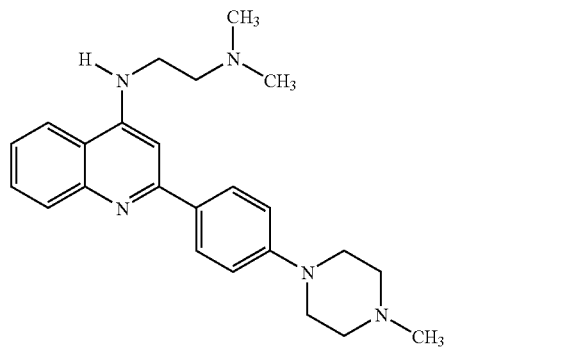

Other mice received 10% dimethyl sulfoxide (DMSO) in an identical manner. Animals were weighed immediately prior to injection (day 1) and then daily until day 5. On day 5, blood was collected by cardiac puncture and analyzed for hematological and biochemical parameters. Animals were monitored daily for morbidity and mortality. Results are shown in FIG. 2 and FIG. 3.

Figure 2A:
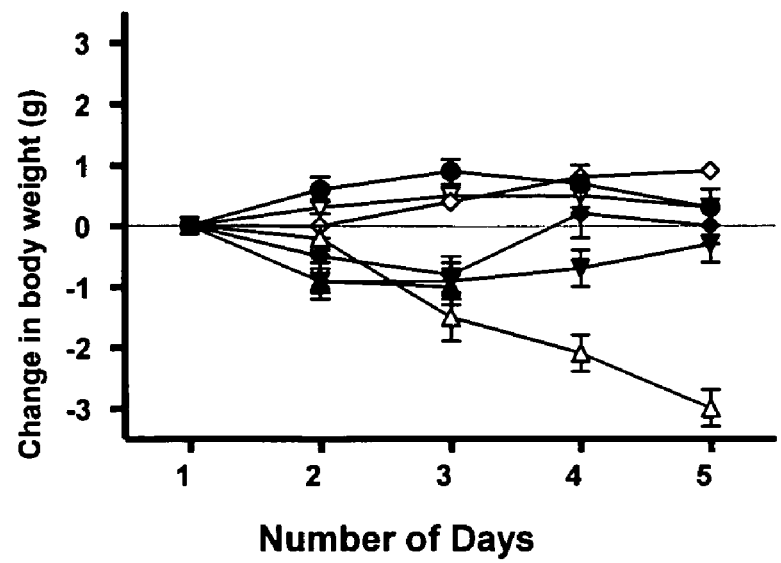
FIG. 2A shows change in mean body weight (grams) and FIG. 2B shows mean body weight (grams) over 5 days for mice treated with dimethysulfoxide (DMSO) control (closed circles), compound CMZ 203-43 (also referred to herein as 203-43) administered at 1 mg and 4 mg (open and closed triangles, respectively), compound CMZ 203-34 at 1 mg and 4 mg (open and closed diamonds, respectively), and compound CMZ 203-49 at 1 mg and 4 mg (open and closed inverted triangles, respectively). N=3 for each treatment group. The group receiving CMZ 203-43 at 4 mg were sick and had to be sacrificed on day 3.
Figure 2B:
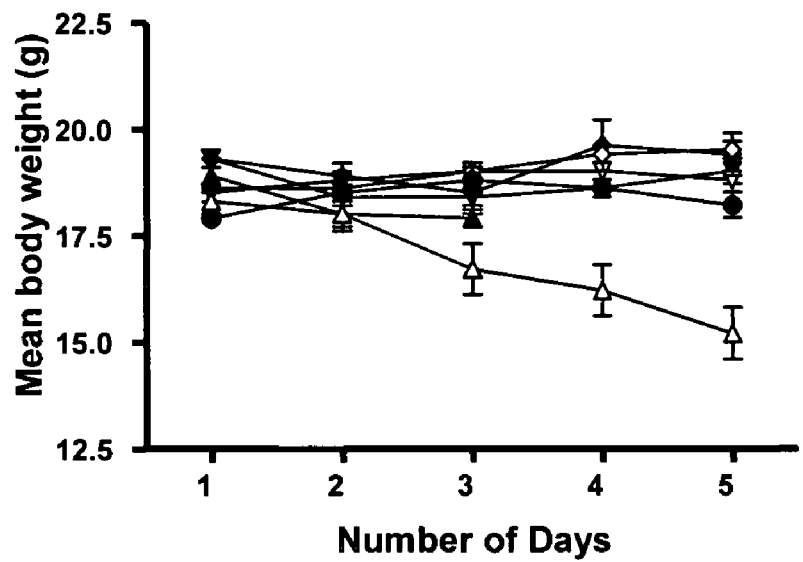

FIG. 2A shows change in body weight (relative to body weight prior to first injection)±standard error of the means for different groups. FIG. 2B shows mean body weight±standard error of the means for different groups. Mice receiving 1.0 mg CMZ 203-43 had significant weight loss, while mice receiving quinazoline at either dose did not. All of the mice receiving 4.0 mg CMZ 203-43 group were dead on day 4. Necropsy of mice in the 4.0 mg CMZ 203-43 group revealed bowel obstruction.

Figure 3:
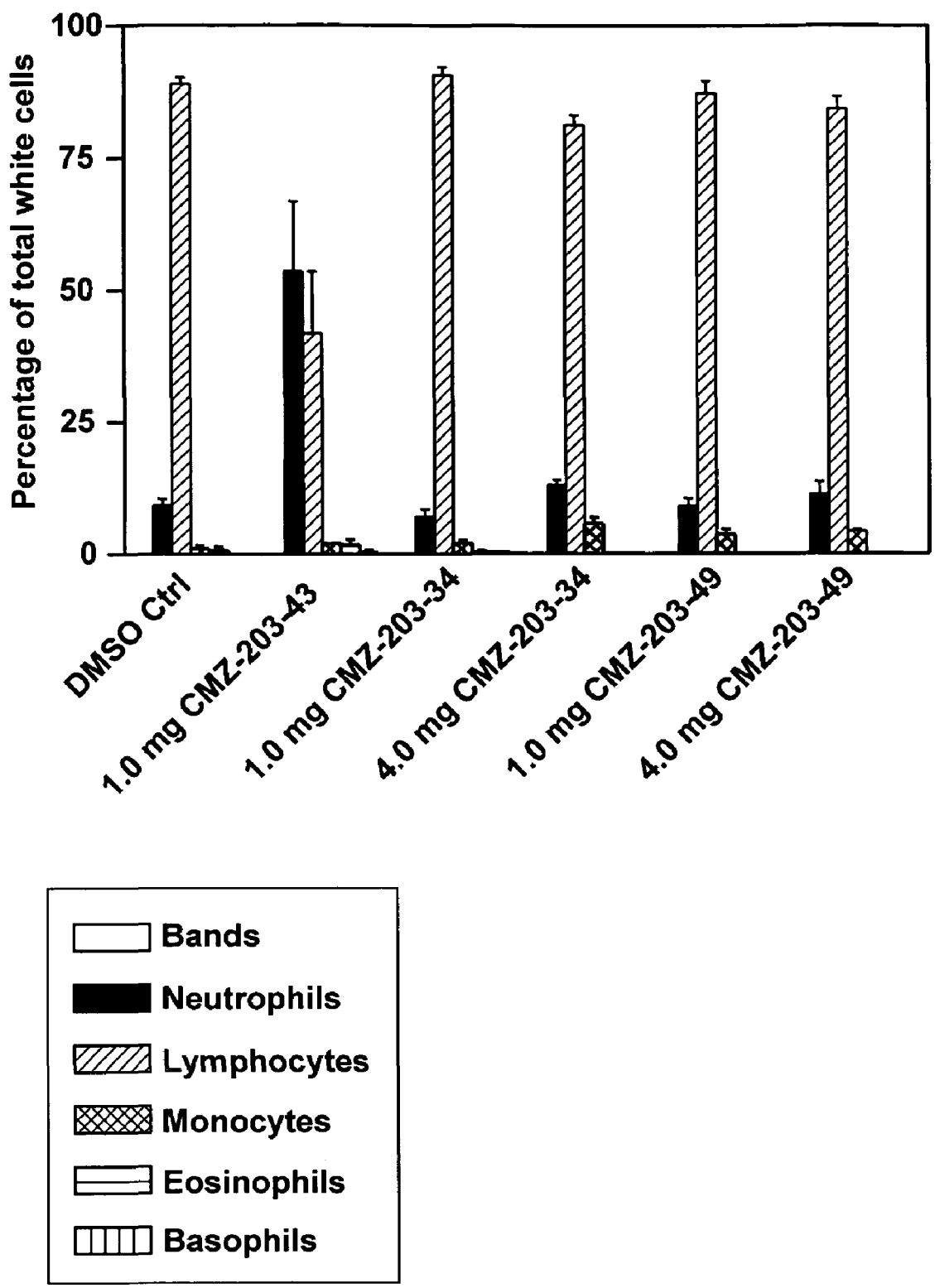
FIG. 3 is a bar graph depicting total and differential white blood cell counts in mice measured five days after administration of a single intraperitoneal dose of specific quinoline and quinazoline compounds. N=3 for each treatment group.

FIG. 3 shows white blood cell (WBC) differential as mean percentage of total white cells±standard error of the means for different groups. Mice treated with 1.0 mg CMZ 203-43 had a significant neutrophilia while mice receiving quinazoline at either dose did not. Data for mice treated with 4.0 mg CMZ 203-43 was not available because all these mice were dead before day 5.

Example 10

Figure 4:
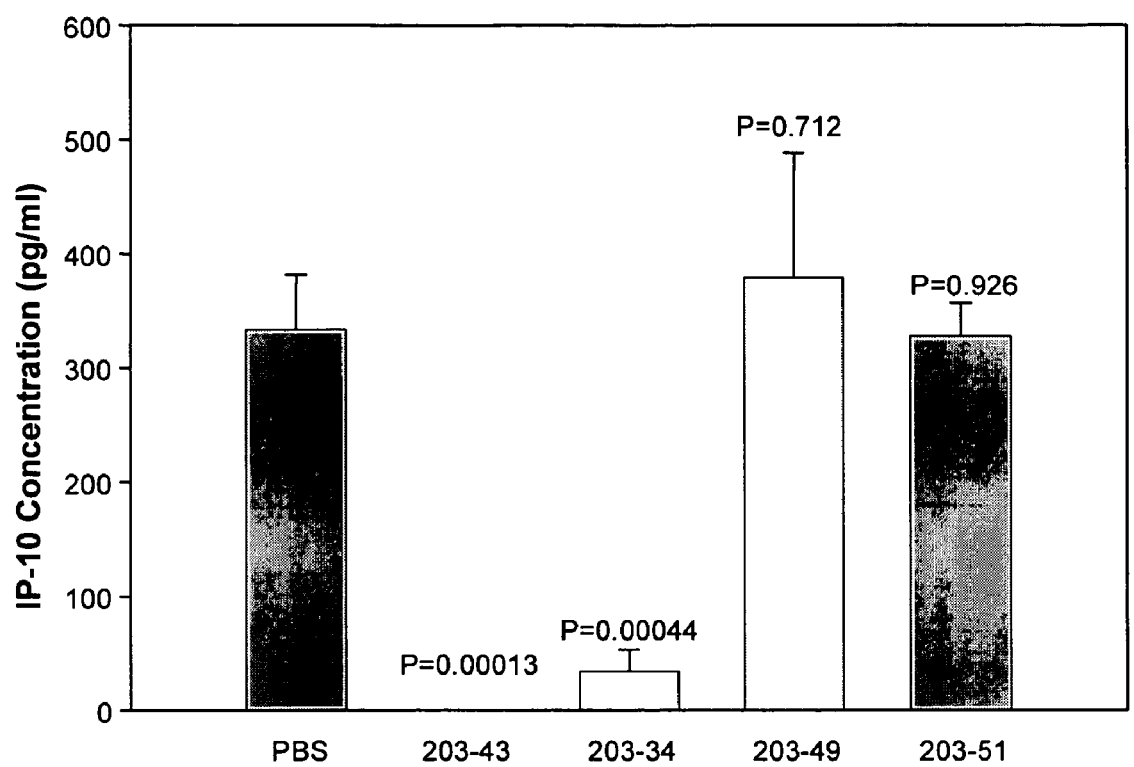
FIG. 4 is a bar graph depicting in vivo inhibition of IP-10 induction (pg/ml) by CpG ODN 2006 following pretreatment with PBS control or a quinoline compound (203-43) or various indicated quinazoline compounds (203-34, 203-49, or 203-51). N=5 for each group.

In Vivo Inhibition of IP-10 by 4-Primary Amino Quinoline and by Quinazolines BALB/c mice (n=5) were pretreated with intraperitoneal injection of 40 µg quinoline 203-43, quinazoline 203-34, 203-49, or 203-51, or with 100 µl of sterile phosphate buffered saline (PBS) control. One hour after the injection, mice were injected subcutaneously with 100 µg CpG ODN 2006. Animals were bled at 3 hr post injection with CpG ODN 2006 and IP-10 levels in plasma measured by IP-10-specific enzyme-linked immunosorbent assay (ELISA). Results are presented in FIG. 4. Serum IP-10 concentration was significantly reduced in mice pretreated with 203-43 (p=0.00013 versus PBS control) or 203-34 (p=0.00044 versus PBS control).

Example 11

In Vivo Inhibition of TNF-α by 4-Primary Amino Quinoline and by Quinazolines

Figure 5:
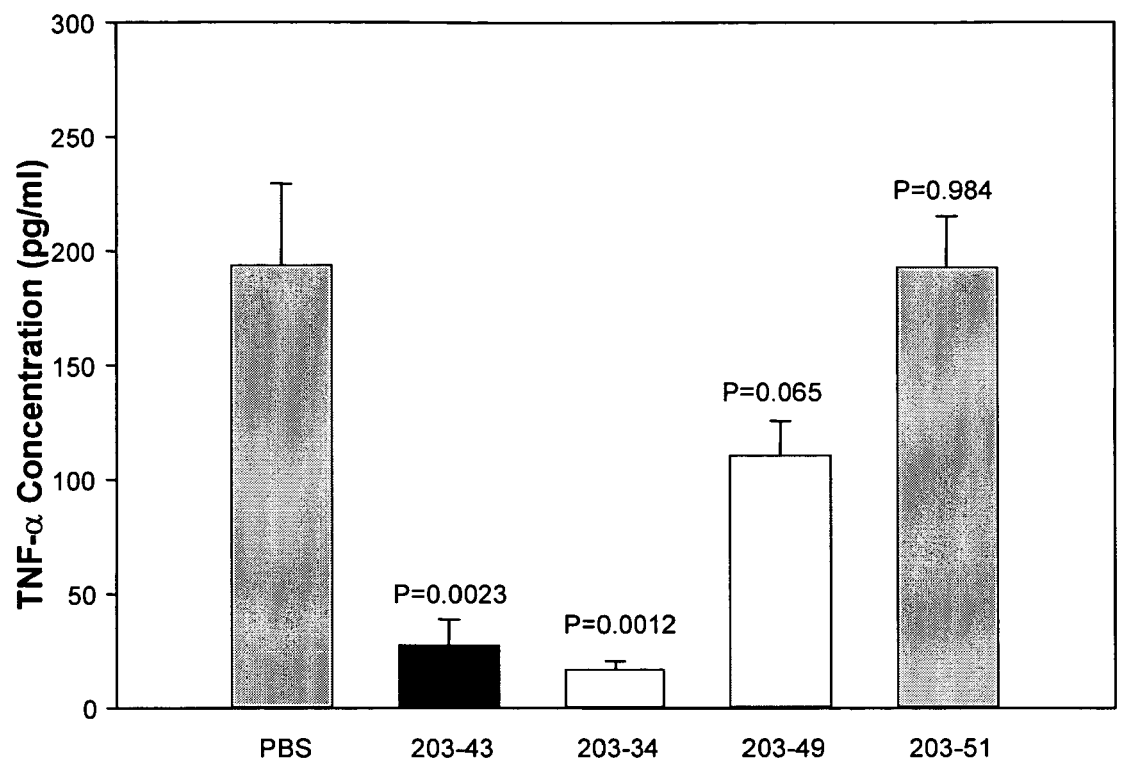
FIG. 5 is a bar graph depicting in vivo inhibition of TNF-α induction (pg/ml) by CpG ODN 2006 following pretreatment with PBS control or a quinoline compound (203-43) or various indicated quinazoline compounds (203-34, 203-49, or 203-51). N=5 for each group.

Groups of BALB/c mice treated as in Example 10 were also analyzed for TNF-α. Animals were bled at 1 hr post injection with CpG ODN 2006 and TNF-α levels in plasma measured by TNF-α-specific ELISA. Results are presented in FIG. 5. Serum TNF-α concentration was significantly reduced in mice pretreated with 203-43 (p=0.0023 versus PBS control) or 203-34 (p=0.0012 versus PBS control). Mice treated with 203-49 showed a trend toward reduced serum TNF-α concentration.

Example 12

Synthesis of CMZ 203-84

A mixture of 4-fluorobenzophenone (16 gm, 0.08 moles) and N-methylpiperazine (14 gm, 0.14 moles) was stirred and refluxed for 20 hours in water containing sodium carbonate (12.7 gm, 0.12 moles). After cooling, the mixture was extracted with ethyl acetate (200 mL). The organic phase was washed with water (100 mL) and was then extracted with 10% hydrochloric acid solution (3×50 mL). The combined acid extracts were washed with ethyl acetate (100 mL) and were then made basic by the addition of 40% sodium hydroxide solution. The solid aminobenzophenone was extracted into ethyl acetate (200 mL) and the extracts were washed with brine. The ethyl acetate was evaporated under vacuum to give the product as a white solid in a yield of 7.0 gm, 33%.

Example 13

Synthesis of CMZ 203-85

A mixture of the benzophenone (15 gm, 0.056 moles) and powdered sodium hydroxide (15 gm) in ethanol (150 mL) was stirred and heated to reflux. The heat was removed and zinc dust (15 gm) was added in portions at a rate that kept the mixture at reflux. After the addition was complete, the mixture was heated at reflux for one hour. The reaction mixture was allowed to cool and was then filtered to remove zinc. The zinc was washed with ethanol (20 mL) and the combined filtrates were added to water (500 mL). The crystalline white product was isolated by filtration, washed with water and dried. The carbinol was obtained in a yield of 12.1 gm, 80%.

CMZ 203-85

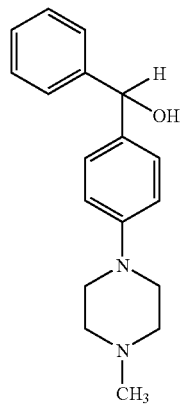
270.37

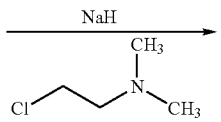

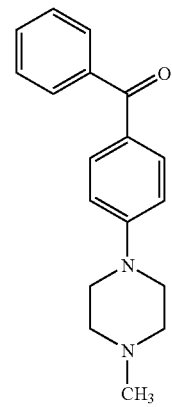
268.35

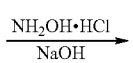

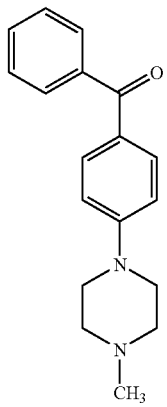
295.38

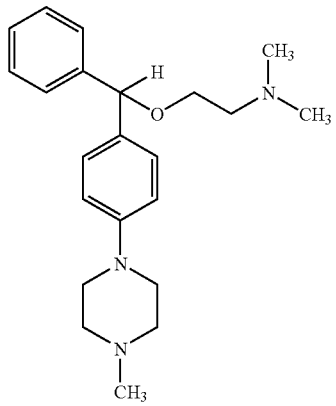
353.50

A solution of the carbinol (1.13 gm, 4.18×10⁻³ moles) in NMP (10 mL) was stirred under nitrogen as a sodium hydride dispersion (0.336 gm of 60%, 8.36×10⁻³ moles) was added. This mixture was stirred at 65° C. until hydrogen evolution stopped. Then 2-(dimethylamino)ethyl chloride hydrochloride (0.602 gm, 4.18×10⁻³ moles) was added and stirring at 65° C. was continued for one hour. The addition of identical portions of sodium hydride dispersion and 2-(dimethylamino)ethyl chloride hydrochloride was done twice more at one hour intervals. After the last addition, the mixture was stirred and heated for two hours and then cooled. The mixture was poured into 10% sodium hydroxide solution (200 mL) and this suspension was extracted with methylene chloride (2×100 mL). The combined extracts were washed with 10% sodium hydroxide solution (100 mL) and were then stripped under vacuum to give the crude product contaminated with some NMP as well as a small amount of starting material. The product was purified by chromatography on silica using 20% methanol in methylene chloride to elute the impurities. The product was then eluted with 20% methanol in methylene chloride containing 1% diethylamine. The yield of CMZ 203-85 was 0.540 gm, 37% as a light brown oil.

Example 14

Synthesis of CMZ 203-88

The benzophenone (4.65 gm, 0.0173 moles) and hydroxylamine hydrochloride (1.89 gm, 0.027 moles) were combined in ethanol (25 mL). To this mixture was added 40% sodium hydroxide solution (8.7 gm, 0.087) moles. The resulting mixture was stirred at reflux until TLC (silica, 10% methanol in methylene chloride) showed that the reaction had gone to completion (about 30 minutes). After cooling, a solution of sodium bicarbonate (20 gm) in water (300 mL) was added and the precipitated solid was isolated by filtration. After washing with water and drying, there was obtained 4.85 gm (95%) of CMZ 203-88 as a white solid.

Example 15

Synthesis of CMZ 203-88-1

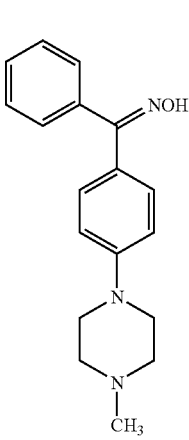

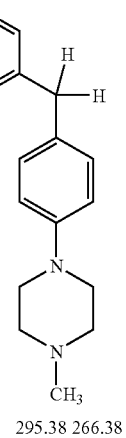
295.38   266.38

A solution of the oxime (1.0 gm, 3.39×10⁻³ moles) in ethanol (20 mL) was stirred at reflux in the presence of 10% palladium on carbon (200 mg). To this mixture was added 90% formic acid (0.35 gm, 6.77×10⁻³ moles) dropwise. Upon complete addition of the formic acid, the reaction mixture was heated at reflux for 30 minutes. The mixture was cooled and filtered free of the catalyst and the filtrates were stripped under vacuum. The residual oil quickly solidified to provide CMZ 203-88-1 in quantitative yield.

Example 16

Synthesis of CMZ 203-89

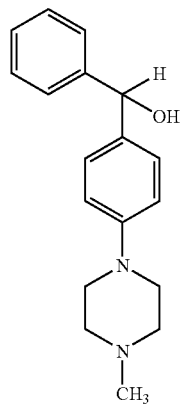

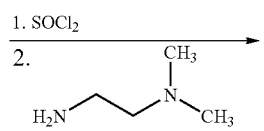

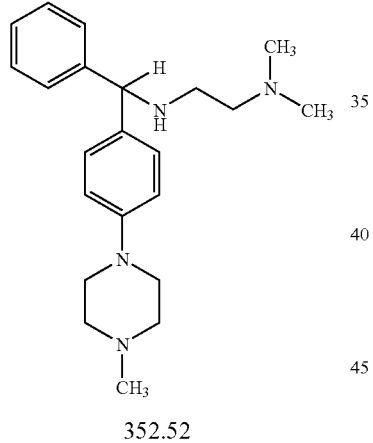

A solution of the carbinol (1.4 gm, 5.0×10$^{-3}$ moles) in DMF (10 mL) and methylene chloride (20 mL) was stirred as thionyl chloride (0.6 gm, 5.0×10$^{-3}$ moles) was slowly added. After stirring at room temperature for 30 minutes, N,N-dimethylethylenediamine (0.88 gm, 1.0×10$^{-3}$ moles) was added dropwise to the hazy solution. This mixture was stirred at room temperature for 30 minutes and was then poured into 5% sodium hydroxide solution (400 mL). This mixture was extracted with methylene chloride (2×100 mL) and the combined extracts were washed with 5% sodium hydroxide solution (200 mL). After drying over magnesium sulfate the extracts were filtered and stripped under vacuum to give an oil. The product was purified by chromatography on silica using 20% methanol in methylene chloride to elute the impurities. The product was then eluted with 20% methanol in methylene chloride containing 1% diethylamine. The yield of CMZ 203-89 was 0.588 gm, 33.4% as a light brown oil.

Example 17

Synthesis of CMZ 203-91

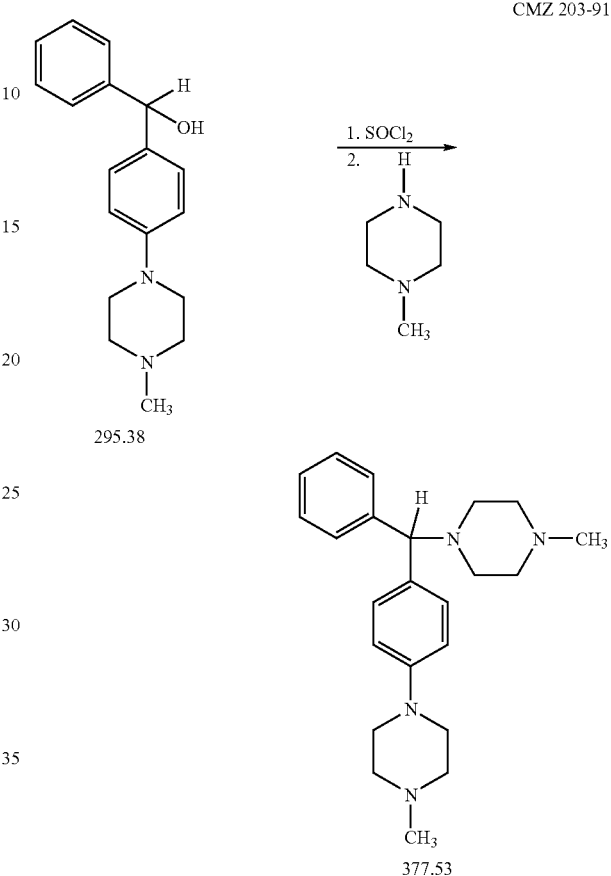

A solution of the carbinol (0.6 gm, 2.03×10$^{-3}$ moles) in DMF (5 mL) was stirred as thionyl chloride (0.242 gm, 2.03× 10$^{-3}$ moles) was slowly added. After stirring at room temperature for 30 minutes, N-methylpiperazine (0.400 gm, 4.0× 10$^{-3}$ moles) was added dropwise to the solution. This mixture was stirred at room temperature for 30 minutes and was then poured into 5% sodium hydroxide solution (200 mL). This suspension was extracted with methylene chloride (2×100 mL) and the combined extracts were washed with water (100 mL). The extracts were stripped under vacuum to give an oil. The product was purified by chromatography on silica using 20% methanol in methylene chloride to elute the impurities. The product was then eluted with 20% methanol in methylene chloride containing 1% diethylamine. The yield of CMZ 203-91 was 0.58 gm, 77% as an oil which crystallized upon standing.

Example 18

Human TLR9 Antagonism by Novel Diarylmethane Compounds of the Invention hTLR9-NFkB-293 cells were counted and seeded at 1.5× 10$^4$ cells per well in 96-well cell culture plates one day before assaying and cultured at 37° C./5% CO$_2$, as described in Example 7. The day of the assay, antagonist was added at varying concentrations starting at 50 μM with a 1/5 to 1/6 dilution for 7 steps. The cells were then stimulated with the EC50 dose of the TLR9 agonist, CpG-ODN 2006, and cultured for 16 h in a humidified incubator at 37° C. The culture supernatant was removed and the cells were treated with lysis buffer and stored at −80° C. before measuring luciferase activity as described in Example 7. Sigmoidal antagonism curves were generated and the inhibitor concentration at which 50% of the agonist response was blocked (IC50) calculated. Results shown in Table 20 under the heading hTLR9 are the IC50 dose (μM) for blockade of a CpG ODN-generated signal in hTLR9-NFkB-293 cells.

TABLE 20

Human TLR9 Antagonism by Novel Diarylmethane Compounds of the Invention

| ID | Structure | hTLR9 |
|---|---|---|
| CMZ 203-84 | 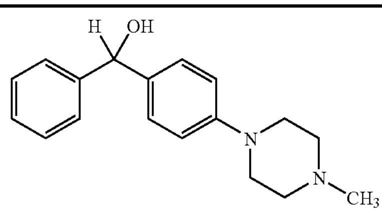 | 25.56 |
| CMZ 203-85 | 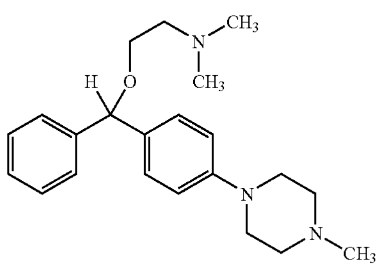 | 0.372 |
| CMZ 203-88 | 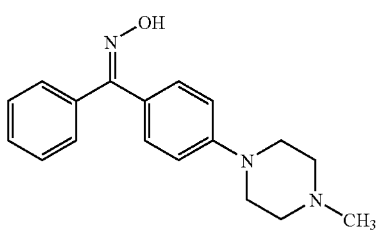 | 11.56 |
| CMZ 203-88-1 | 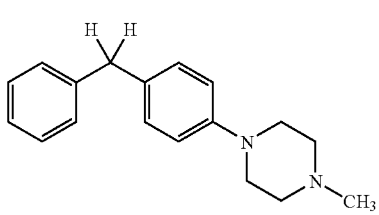 | 12.01 |
| CMZ 203-89 | | 0.241 |
| CMZ 203-91 | | 3.95 |

Example 19

Synthesis of CMZ 203-34

Step 1.

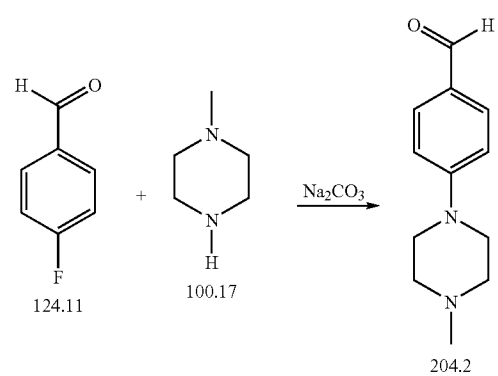

A mixture of 4-fluorobenzaldehyde (10 gm, 0.08 moles) and N-methylpiperazine (14 gm, 0.14 moles) in water (80 mL) containing sodium carbonate (12.7 gm, 0.12 moles) was stirred and refluxed for 21 hours. After cooling, the mixture was poured into a separatory funnel containing water (200 mL) and the oily product was extracted into methylene chloride (3×50 mL). The combined extracts were washed with water and were then stripped under vacuum. The product, which was isolated as an oil, solidified into a tan solid upon cooling. The solid product was triturated in hexane and isolated by filtration. After drying, there was obtained 14.9 gm (91%) of N-(4-formylphenyl)-N'-methylpiperazine as an off white solid.

Step 2.

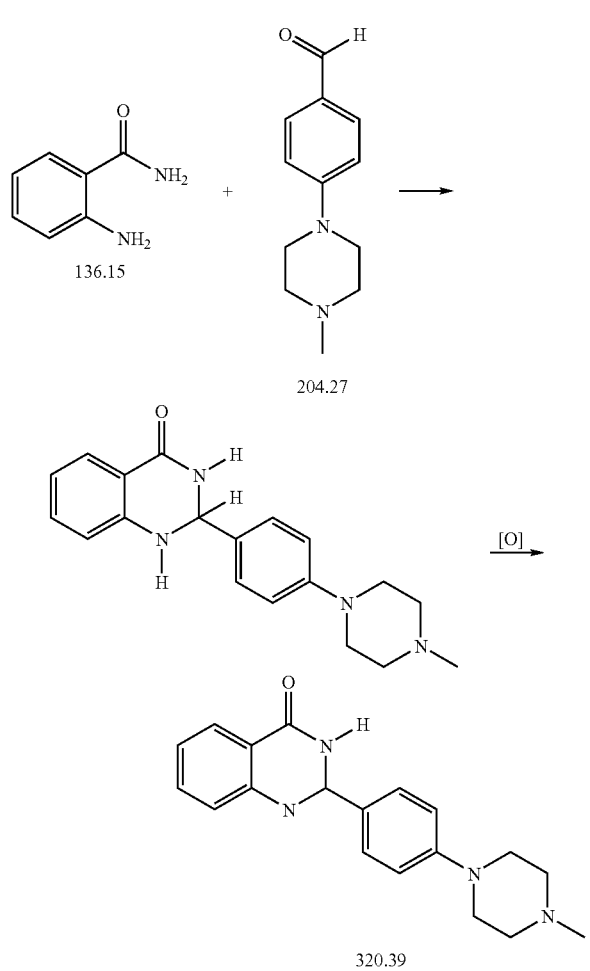

Anthranilamide (9.94 gm, 0.073 moles) and N-(4-formylphenyl)-N'-methylpiperazine (14.9 gm, 0.073 moles) were combined in NMP (100 mL). This mixture was stirred and warmed until dissolution was complete. To the warm solution was added p-toluenesulfonic acid monohydrate (2.0 gm) after which the solution was heated at 100° C. for 30 minutes.

Acetic acid (50 mL) was added and the mixture was stirred and heated at 100° C. for an additional 30 minutes. Chloranil (17.9 gm, 0.073 moles) was added in portions over a period of approximately two minutes. The dark solution was heated at 100° C. for 10 minutes. The solution was cooled to room temperature and was diluted with water (500 mL) and tert-butylmethyl ether (TBME, 500 mL). The mixture was stirred and made basic by the addition of solid sodium carbonate. After stirring for 15 minutes the precipitated product was isolated by filtration. The crude product was re-suspended in warm water, stirred for 5 minutes and collected by filtration. After washing with water followed by TBME, the solid was air dried. The dried quinazolinone was recrystallized from n-butanol to give 11.1 gm (50%) of product as colorless needles.

Step 3.

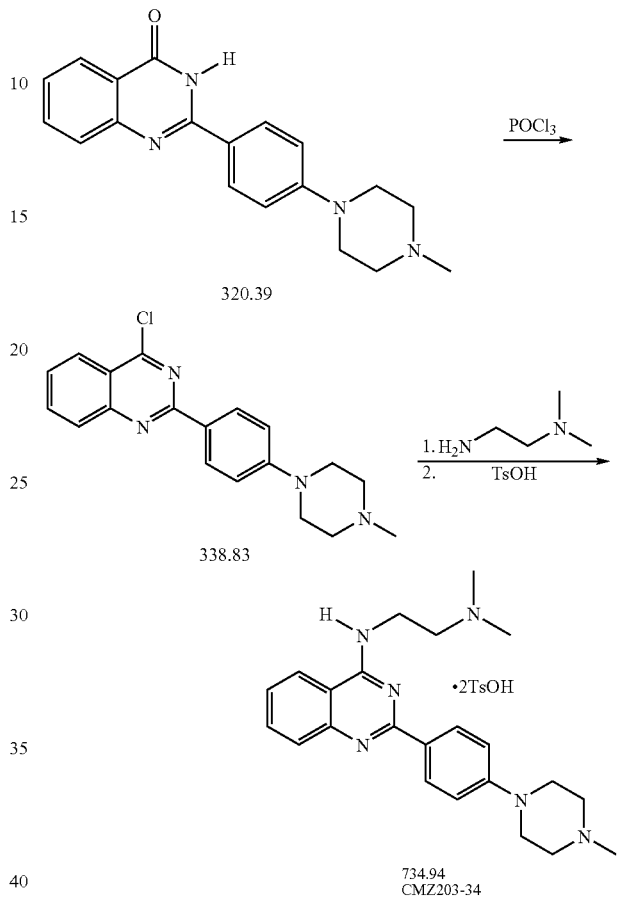

The quinazolinone (2.4 gm, $7.5 \times 10^{-3}$ moles) was added in portions with stirring to phosphorous oxychloride (10 mL). This mixture was warmed to 80° C. to give a red solution from which solid began to precipitate. The mixture was stirred at 80° C. for 15 minutes and was then heated briefly to reflux. Upon cooling the slurry was slowly added to a cold, stirred solution of 10% sodium carbonate (650 mL). After stirring for 15 minutes, the solid chloroquinazoline was extracted into chloroform (2×150 mL). The combined extracts were washed with brine and then dried over magnesium sulfate. The solution was filtered to remove the drying agent and the filtrates were stripped under vacuum to give a yellow solid. N-methylpyrrolidinone (NMP, 20 mL) was added and the solid was dissolved by warming. N,N-dimethylethylenediamine (1.32 gm, 0.015 moles) was added and the solution was then warmed at 100° C. for 30 minutes. After cooling, the NMP solution was diluted with water (200 mL) and concentrated ammonium hydroxide (50 mL). The product, which had precipitated, was extracted into methylene chloride (2×100 mL). The extracts were combined, dried over magnesium sulfate and then, after filtration, were stripped to give the product as a light brown oil. This was purified by chromatography on silica using 10% methanol in methylene chloride as eluent. In this manner 600 mg ($1.54 \times 10^{-3}$ moles) of pure quinazoline was isolated as an oil. This was dissolved in t-butylmethyl ether (TBME, 50 mL) and was stirred as a solution of toluenesulfonic acid monohydrate (584 mg, $3.1 \times 10^{-3}$ moles) dissolved in TBME (50 mL) was added. The solid bis-tosylate salt was isolated by filtration, washed with TBME and dried to give 1.0 gm of the product as a yellow solid.

Example 20

Synthesis of CMZ 203-44 ture was isolated by filtration. The salt was washed with ethanol and dried. The yield was 1.77 gm, (96% from crude).

Example 21

Synthesis of CMZ 203-45

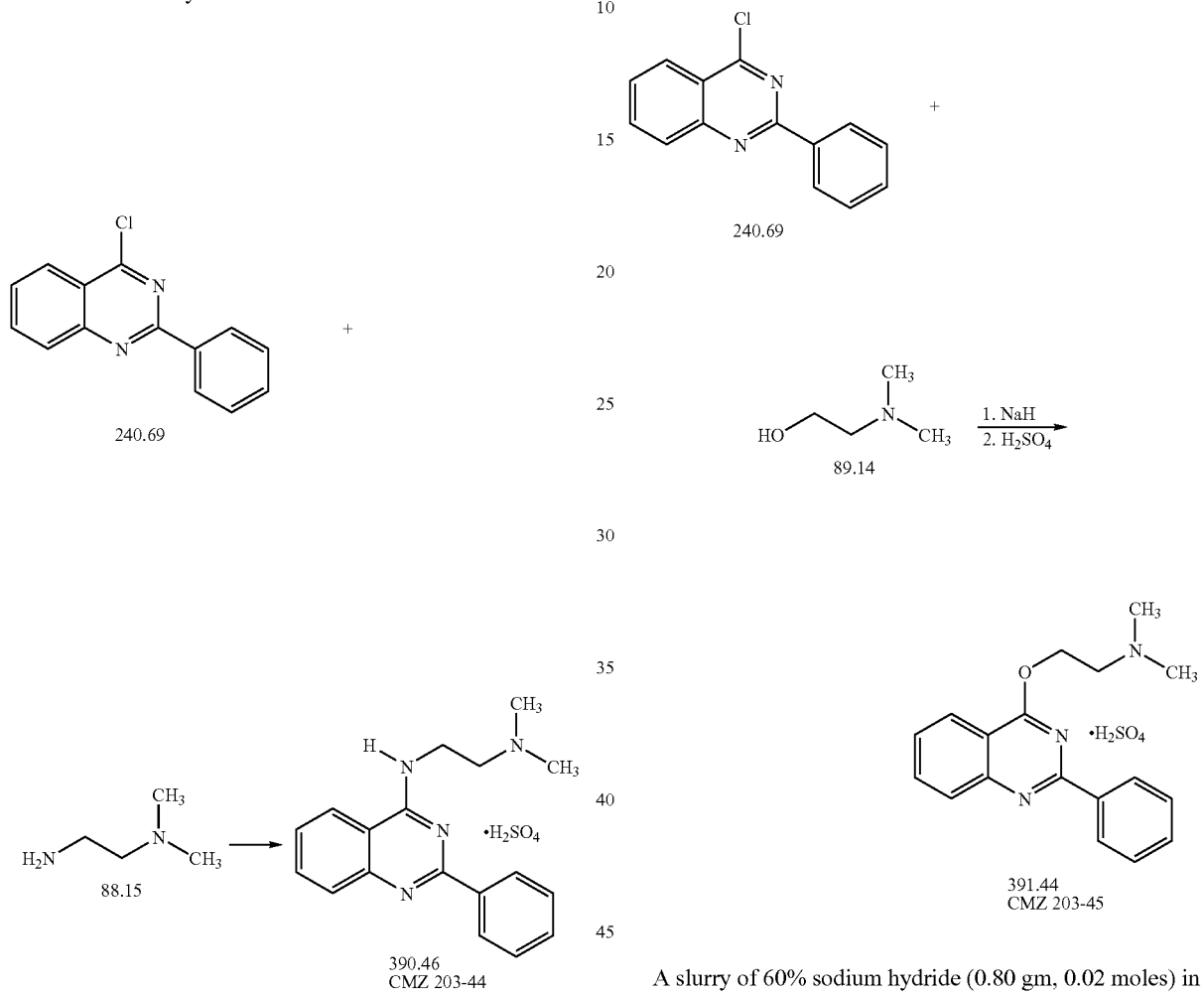

N,N-dimethylethylenediamine (3.5 gm, 0.04 moles) and 2-phenyl-4-chloroquinazoline (2.4 gm, 0.01 moles) were combined in n-butanol (50 mL) and were brought to reflux. Once reflux had been achieved, TLC (silica, 10% methanol in dichloromethane) showed that the reaction was complete. The solution was cooled and stripped. The residue was dissolved in t-butylmethyl ether (TBME) and the solution was washed with water. After drying over magnesium sulfate the solution was filtered and stripped to give 1.37 gm (0.0047 moles, 47%) of the crude product as an oil. This was dissolved in ethanol (25 mL) and was treated with a solution of concentrated sulfuric acid (0.46 gm, 0.0047 moles) dissolved in ethanol (5 mL). The crystalline sulfate salt began to separate within a few seconds and after 30 minutes at room tempera- A slurry of 60% sodium hydride (0.80 gm, 0.02 moles) in NMP (50 mL) was stirred under nitrogen as N,N-dimethylethanolamine (1.96 gm, 0.022 moles, 2.2 mL) was slowly added via syringe. After the amine had been added the solution was stirred at 30° C. for 10 minutes after which 2-phenyl-4-chloroquinazoline (2.4 gm, 0.01 moles) was added in a single portion. Stirring was continued at 40° C. for 30 minutes after which TLC (silica, 10% methanol in methylene chloride) showed that the reaction had gone to completion. The solution was cooled and poured into water (250 mL). The product was extracted into methylene chloride (3×50 mL). After drying over magnesium sulfate the solution was filtered and stripped to give the crude product as an oil. This was dissolved in ethanol (20 mL) and was treated with a solution of concentrated sulfuric acid (0.85 gm, 0.0087 moles) dissolved in ethanol (10 mL). The crystalline sulfate salt separated slowly and after 60 minutes at room temperature was isolated by filtration. The salt was washed with ethanol and dried. The yield was 1.37 gm, (40% based on the sulfuric acid).

Example 22

Synthesis of CMZ 203-49

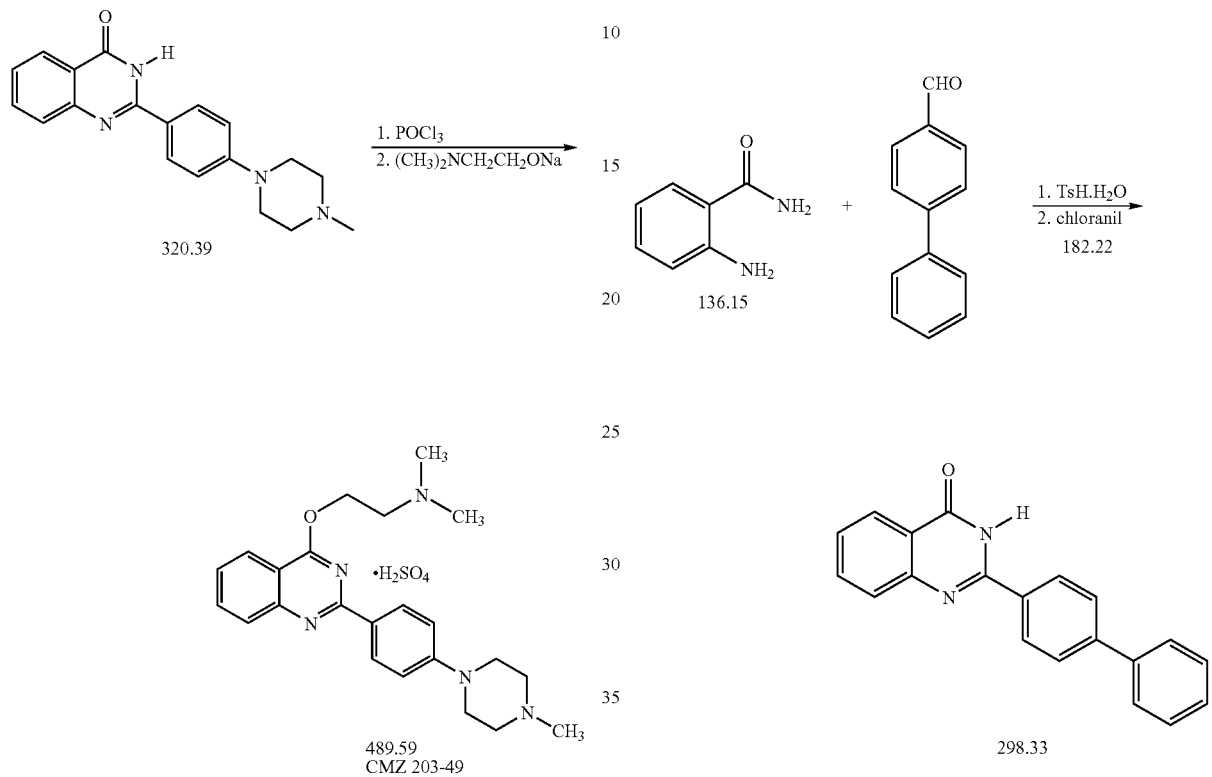

The quinazolinone (3.2 gm, 0.01 moles) was added in portions with stirring to phosphorous oxychloride (10 mL). This mixture was refluxed for 30 minutes. The orange slurry was cooled and TBME (100 mL) was added. After stirring for 10 minutes the chloroquinazoline was isolated by filtration and added to a solution of the sodium salt of N,N-dimethylaminoethanol in NMP (50 mL). The solution of the sodium salt of N,N-dimethylaminoethanol in NMP was prepared as follows. A slurry of 60% sodium hydride (2.1 gm, 0.05 moles) in NMP (50 mL) was stirred under nitrogen as N,N-dimethylethanolamine (4.9 gm, 0.055 moles) was slowly added via syringe. After the amine had been added the solution was stirred at 30° C. for 10 minutes. This mixture was stirred at 100° C. for 30 minutes. The cooled solution was added to methylene chloride (150 mL) and this solution was extracted with water (3×150 mL). The methylene chloride solution was stripped and the residue was dissolved in ethanol (50 mL). To this solution was added concentrated sulfuric acid (0.8 gm, 0.008 moles) dissolved in ethanol (5 mL). The solid salt which separated was isolated by filtration, washed with ethanol and TBME and dried. The yield was 1.3 gm, 23%.

Example 23

Synthesis of CMZ 203-51

Step 1.

A solution of anthranilamide (6.8 gm, 0.05 moles) and biphenylcarboxaldehyde (9.1 gm, 0.05 moles) in DMF (100 mL) was stirred as p-toluenesulfonic acid monohydrate (1.0 gm) was added. A yellow solution formed which quickly changed to a thick slurry as the dihydroquinazoline precipitated. The slurry was heated to 100° C. which caused most of the solid to dissolve. To this hot mixture was added chloranil (12.3 gm, 0.05 moles) in portions over a 2 minute period. A dark solution formed from which the product began to crystallize. The mixture was heated to boiling to provide a dark solution. Upon cooling, the quinazolinone crystallized as colorless needles. The product was isolated by filtration, washed well with DMF and acetone, and then dried. The yield was 11.9 gm, 80%.

Step 2.

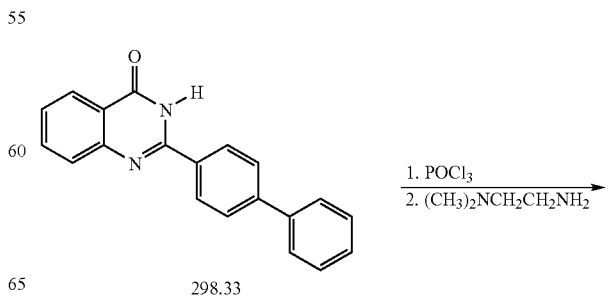

-continued

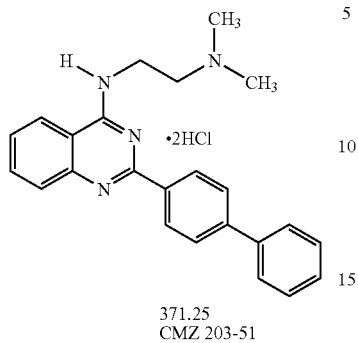

371.25
CMZ 203-51

Phosphorous oxychloride (12 mL) and the biphenylquinazoline (2.98 gm, 0.01 moles) were stirred together and refluxed for one hour. The excess phosphorous oxychloride was removed by distillation and the oily yellow residue was placed under aspirator vacuum to remove traces of phosphorous oxychloride. The resulting yellow solid was triturated in hexane which was removed by decantation. To the yellow solid was added n-butanol (50 mL) and N,N-dimethylethylenediamine (6 mL). This solution was stirred and refluxed for 30 minutes. The butanol solution was cooled and poured into a separatory funnel containing TBME (200 mL) and 10% aqueous hydrochloric acid (200 mL). The funnel was vigorously shaken after which the layers were allowed to separate. The aqueous layer was isolated and the flask in which it was collected was scratched with a glass rod. The product began to immediately separate as a pale yellow solid. After 30 minutes at room temperature the product was isolated by filtration and was washed with a small amount of cold water. After drying there was obtained 3.64 gm (82%) of product as a pale yellow solid.

Example 24

Synthesis of CMZ 203-76

Step 1.

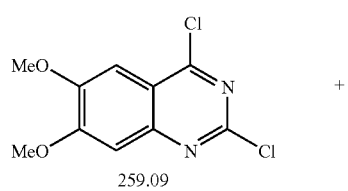

259.09

-continued

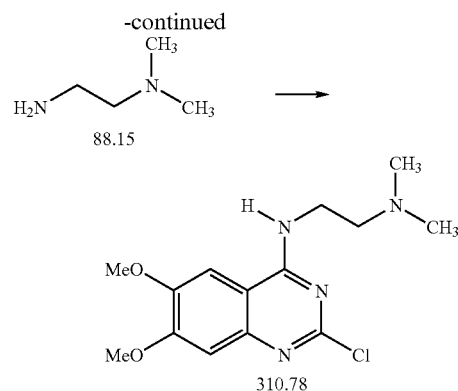

88.15

310.78

A solution of 2,4-dichloro-6,7-dimethoxyquinazoline (5.2 gm, 0.02 moles) and N,N-dimethylethylenediamine (1.76 gm, 0.02 moles) in methylene chloride (65 mL) was stirred at room temperature for 2 hours. To the slurry that had formed another portion of N,N-dimethylethylenediamine (1.76 gm, 0.02 moles) was added forming a clear solution. This solution was stirred at room temperature overnight. The solution was poured into 10% sodium carbonate solution (200 mL) causing the product to separate as a solid. The solid was isolated by filtration and then washed with water followed by methylene chloride. This solid was recrystallized from 2-propanol to give 2.6 gm (42%) of the purified product as a white crystalline solid.

Step 2.

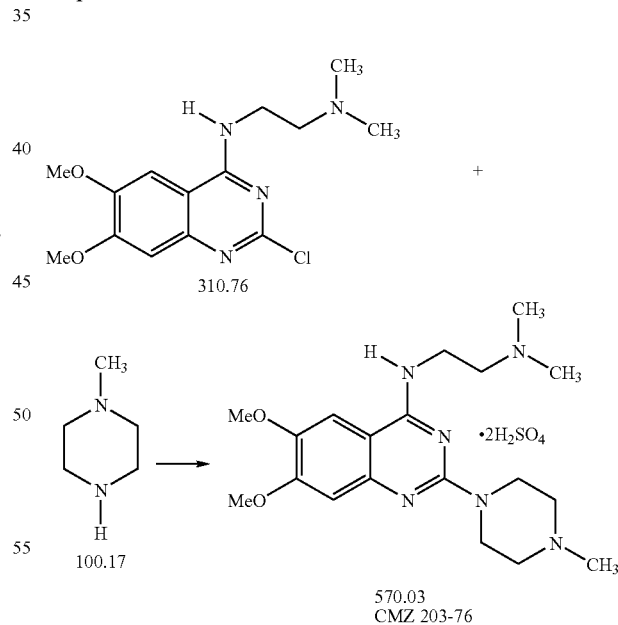

310.76

100.17

570.03
CMZ 203-76

A mixture of the chloroquinazoline (930 mg, 0.003 moles) and N-methylpiperazine (5 mL) was heated at 100° C. for 3 hours. The solution was cooled and stripped under vacuum. n-Butanol (10 mL) was added and the solution was again stripped under vacuum to remove residual N-methyl piperazine. The residue was dissolved in ethanol (20 mL) and a solution of sulfuric acid (0.59 gm, 0.006 moles) in ethanol (5 mL) was added. The mixture was refluxed for one minute and then cooled. The product was isolated by filtration, washed with ethanol followed by TBME and then dried. The yield was 0.85 gm, (50%).

Example 25

Synthesis of CMZ 203-78

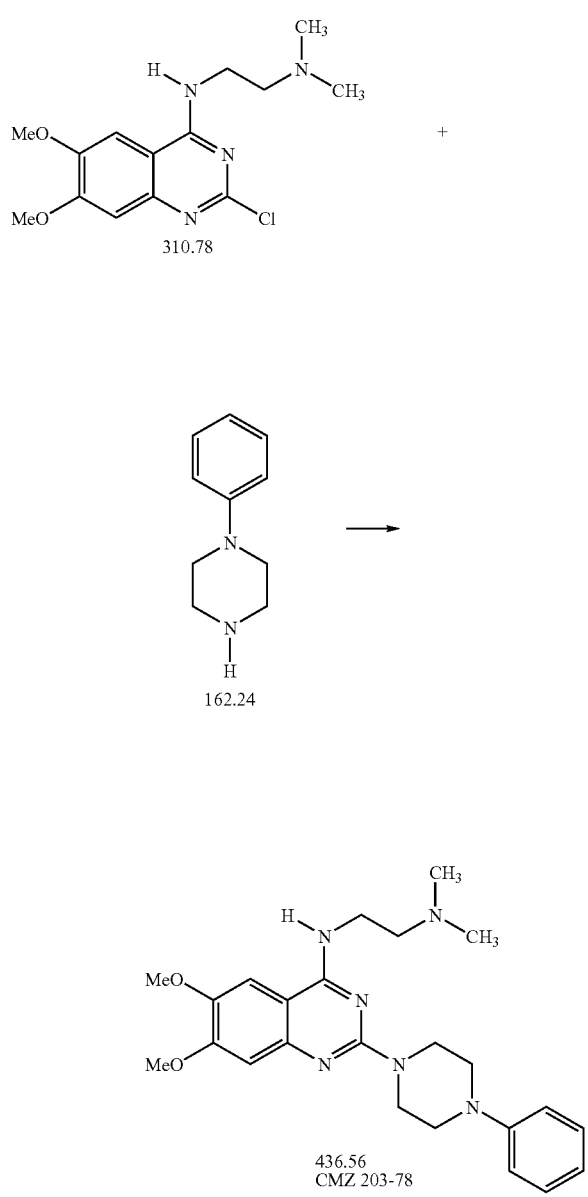

436.56
CMZ 203-78

A mixture of the chloroquinazoline (1.55 gm, 0.005 moles) and N-phenylpiperazine (1.6 gm, 0.01 moles) in n-butanol (5 mL) was heated at 100° C. for 2 hours. The resulting slurry was diluted with n-Butanol (15 mL) and the mixture was heated to boiling to give a clear solution. Upon cooling a solid separated which was isolated by filtration. The solid was stirred in warm water for 15 minutes to remove a small amount of N-phenyl-piperazine. The product was isolated by filtration, washed with warm water and dried to provide 1.0 gm (46%) of the product as a white solid.

Example 26

Synthesis of CMZ 203-87

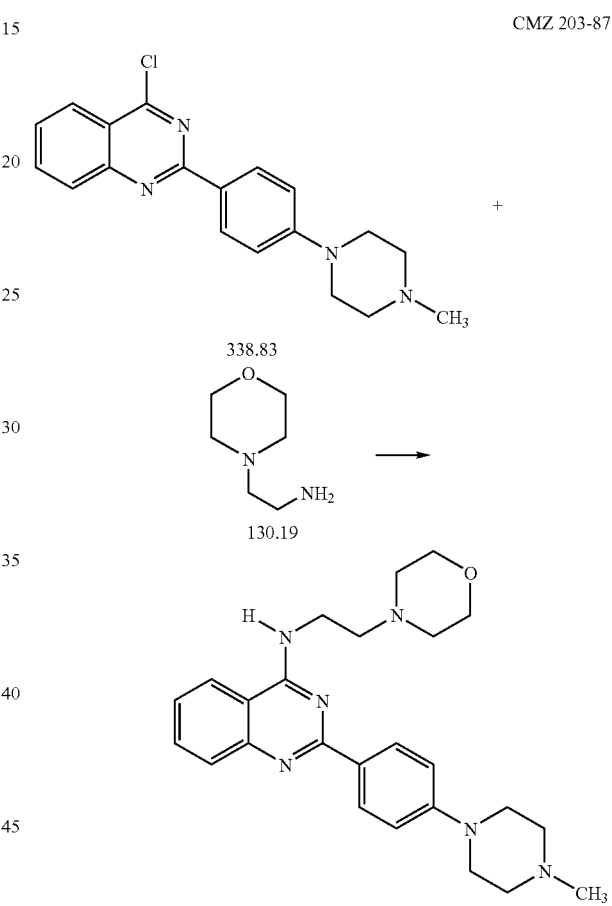

432.56

A mixture of the 4-chloroquinazoline (2.74 gm, $8.0 \times 10^{-3}$ moles) and N-aminoethyl-morpholine (2.10 gm, $1.6 \times 10^{-2}$ moles) in ethanol (25 mL) was refluxed for 2 hours. The reaction mixture was cooled and poured into water (200 mL) containing ammonia (50 mL of 28%) and the precipitated product was extracted into methylene chloride (3×100 mL). The combined extracts were washed with water (200 mL) and then dried over magnesium sulfate. After filtering to remove the drying agent the solution was stripped under vacuum to give the crude product as a tan solid. This solid was dissolved in warm methylene chloride (10 mL) and the solution was diluted with warm hexane (20 mL). Upon cooling, the product crystallized as a tan solid. This was isolated by filtration, the solid washed with 30% methylene chloride in hexane and dried. The yield was 1.2 gm, (35%).

Example 27

Synthesis of CMZ 203-93

Step 1.

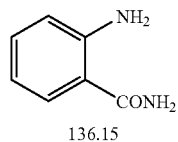
136.15

+

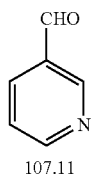 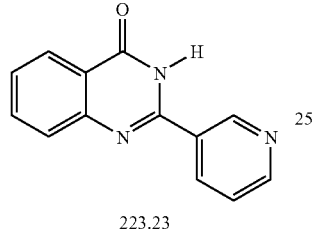
107.11
223.23

To a solution of anthranilamide (13.6 gm, 0.10 moles) and 3-pyridinecarboxaldehyde (10.7 gm, 0.10 moles) in NMP (100 mL) and acetic acid (50 mL) was added p-toluenesulfonic acid monohydrate (2.0 gm). This solution was stirred at 50° C. for 30 minutes at which point chloranil (24.6 gm, 0.10 moles) was added in portions through a funnel during one minute. The dark solution was stirred and cooled to room temperature which caused the quinazolinone to crystallize. The solid was isolated by filtration, washed with acetone/NMP (1:1) followed by acetone. After drying, the crude product was recrystallized from n-butanol (200 mL) and NMP (90 mL). The quinazolinone was isolated as tan fibrous crystals in a yield of 10.6 gm, 47.5%.

Step 2.

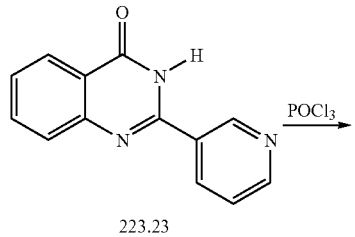
223.23

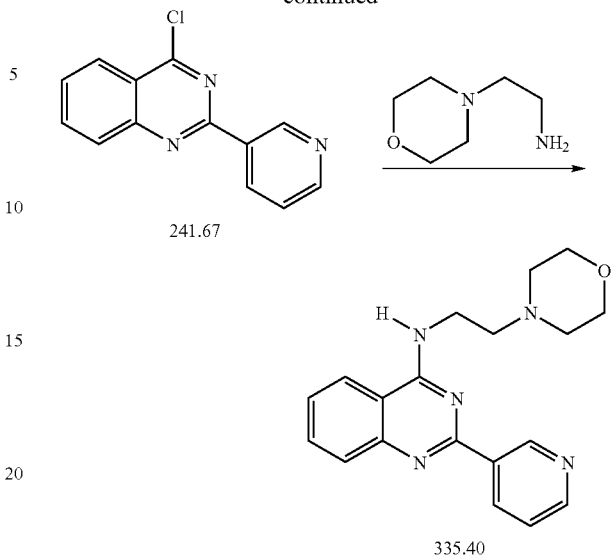
241.67

335.40

A portion of the quinazolinone (4.46 gm, 0.02 moles) was refluxed in phosphorous oxychloride (20 mL) for one hour. After cooling, the solution was carefully poured into cold 20% sodium carbonate solution (500 mL). The solid chloroquinazoline was isolated by filtration, washed with water and dissolved in methylene chloride (400 mL). The solution was dried over magnesium sulfate, filtered and stripped to give the chloroquinazoline as a pale yellow solid in a yield of 3.7 gm, 76.5%. The 4-chloroquinazoline (3.7 gm, 0.015 moles) was refluxed in ethanol with N-2-aminoethylmorpholine (3.99 gm, 0.031 moles) for one hour. Once cooled, the solution was stripped and the residue was dissolved in water (400 mL). The solution was made basic by the addition of sodium carbonate and the product was extracted into methylene chloride (2×100 mL). The combined extracts were washed with water (50 mL) and were then dried over magnesium sulfate. After filtration, the extracts were stripped to give the product as a tan solid. The solid was recrystallized from ethyl acetate (25 mL) and hexane (50 mL). The product, 203-93 was isolated as an off white solid in a yield of 2.86 gm, 56.0%.

Example 28

Synthesis of CMZ 203-95

Step 1.

CMZ 203-93

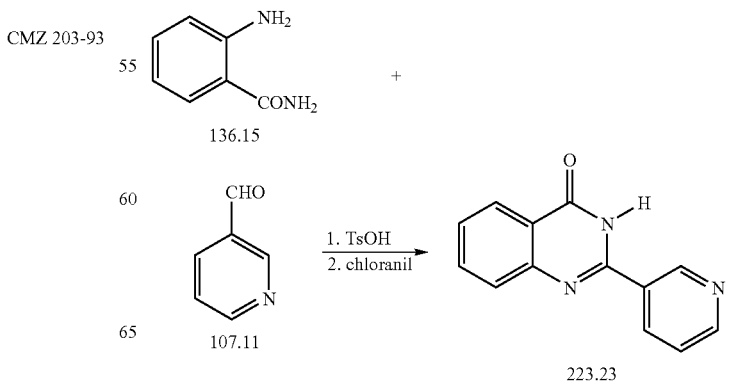

To a solution of anthranilamide (13.6 gm, 0.10 moles) and 2-pyridinecarboxaldehyde (10.7 gm, 0.10 moles) in methanol (250 mL) and acetic acid (25 mL) was added p-toluenesulfonic acid monohydrate (2.0 gm). This solution was stirred at 50° C. for 30 minutes at which point chloranil (24.6 gm, 0.10 moles) was added in portions through a funnel during one minute. The funnel was washed with NMP (25 mL). This mixture was heated to reflux for 5 minutes. The dark solution was stirred and cooled to room temperature which caused the quinazolinone to crystallize. The solid was isolated by filtration, washed with acetone. After drying, the crude product was recrystallized twice from n-butanol. A small amount of tetrachlorohydroquinone will co-crystallize under these conditions. It can be removed by stirring the solid in warm 5% sodium carbonate solution. The quinazolinone was isolated as a tan solid in a yield of 9.5 gm, 43%.

Step 2.

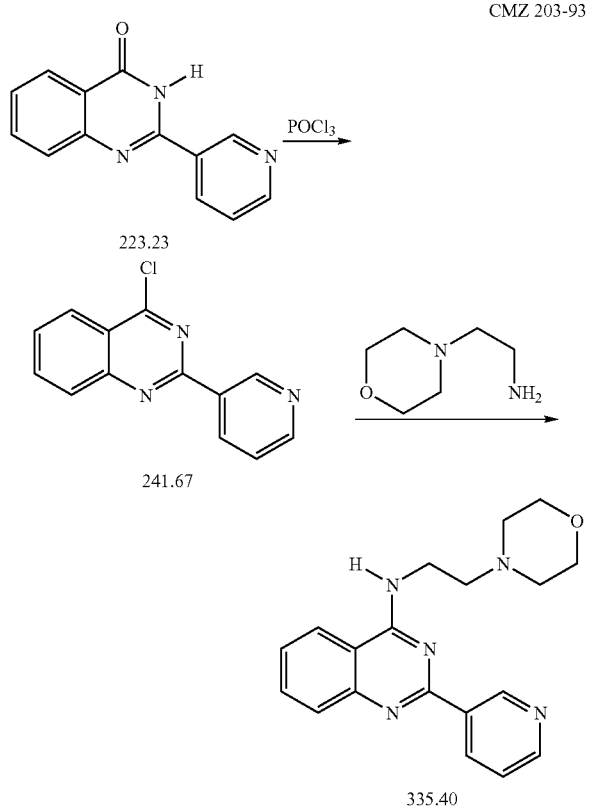

CMZ 203-93

A portion of the quinazolinone (4.46 gm, 0.02 moles) was refluxed in phosphorous oxychloride (20 mL) for 30 minutes. After cooling, the solution was carefully poured into cold water (500 mL). This solution was neutralized by the addition of 40% sodium hydroxide solution which caused the chloroquinazoline to separate as a white solid. The solid chloroquinazoline was isolated by filtration, washed with water and dissolved in methylene chloride (300 mL). The solution was dried over magnesium sulfate, filtered and stripped to give the chloroquinazoline as a pale yellow solid in a yield of 2.75 gm, 57%. The 4-chloroquinazoline (2.75 gm, 0.0114 moles) was refluxed in ethanol with N-2-aminoethylmorpholine (2.97 gm, 0.0228 moles) for one 30 minutes. Once cooled, the solution was poured into 10% sodium hydroxide solution (200 mL) and the product was extracted into methylene chloride (3×1100 mL). The combined extracts were washed with 110% sodium hydroxide (1150 mL) and were then dried over magnesium sulfate. After filtration, the extracts were stripped to give the product as a tan solid. The solid was recrystallized from n-butanol (10 mL) and hexane (20 mL). The product, 203-95 was isolated as an off white solid in a yield of 1.32 gm, 34.5%.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

We claim:

1. A quinazoline compound having a structural formula

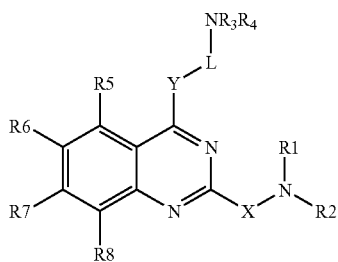

Formula XVIII wherein

X is an aryl or heterocyclic group, provided that if X is a phenyl group, $NR_1R_2$ is part of a heterocycle or is a diamine $NR_{13}(CH_2)_n NR_{14}R_{15}$, wherein n is an integer from 2 to 6, inclusive, and $R_{13}$, $R_{14}$, and $R_{15}$ are each independently a hydrogen atom or an alkyl group;

$R_1$ and $R_2$ are each independently a hydrogen atom or an alkyl, alkenyl, alkylamino, or aryl group, wherein $R_1$ and $R_2$ optionally are combined to form a heterocycle;

Y is a sulfur atom, $CR_9R_{10}$, or $NR_{11}$, where $R_9$, $R_{10}$, and $R_{11}$ are each independently a hydrogen atom or an alkyl, alkenyl, or aryl group, wherein any one of $R_9$, $R_{10}$, and $R_{11}$ optionally is combined with $R_3$ or $R_4$ to form a heterocycle;

L is an alkyl or alkenyl group containing from 1 to 10 carbons or is an aryl group;

R_3 and R_4 are each independently a hydrogen atom or an alkyl, alkenyl, or aryl group, wherein R_3 and R_4 optionally are combined to form a heterocycle; and R_5, R_6, R_7, and R_8 are each independently a hydrogen atom, a halogen atom, or an alkyl, alkenyl, aryl, heterocyclic, nitro, cyano, carboxy, ester, ketone, amino, amido, hydroxy, alkoxy, mercapto, thio, sulfoxide, sulfone, or sulfonamido group, wherein any pair of $R_5$, $R_6$, $R_7$, and $R_8$ which are adjacent one another optionally are combined to form a heterocycle or a carbocycle, and pharmaceutically acceptable hydrates and salts thereof.

2. The quinazoline composition of claim 1, wherein
$R_6$ and $R_7$ are each independently a halogen atom or an alkoxy group.

3. The quinazoline composition of claim 1, wherein
$R_6$ and $R_7$ are each independently a chlorine atom or a methoxy group.

4. The quinazoline composition of claim 1, wherein
X is an aryl group;
$NR_1R_2$ is a heterocyclic amine or $NR_{13}(CH_2)_nNR_{14}R_{15}$, wherein n is an integer from 2 to 6, inclusive, and $R_{13}$, $R_{14}$, and $R_{15}$ are each independently a hydrogen atom or an alkyl group;
Y is $NR_{11}$ where $R_{11}$ is a hydrogen atom or an aryl or alkyl group;
L is absent or is a $C_2$-$C_6$ alkyl group;
$R_3$ and $R_4$ are each independently a hydrogen atom or an alkyl group, wherein $R_3$ and $R_4$ optionally are combined to form a heterocycle; and
$R_5$, $R_6$, $R_7$, and $R_8$ are each independently a hydrogen atom, a halogen atom, or an alkoxy group,
and pharmaceutically acceptable hydrates and salts thereof.

5. The quinazoline compound of claim 4, wherein
$NR_1R_2$ is a substituted or unsubstituted piperazino or morpholino group or is the diamine $NR_{13}(CH_2)_nNR_{14}R_{15}$, wherein n is an integer from 2 to 6, inclusive, $R_{13}$ is a hydrogen atom, and $R_{14}$, and $R_{15}$ are each independently an alkyl group;
Y is NH; and
L is a $C_2$-$C_6$ alkyl-group,
and pharmaceutically acceptable hydrates and salts thereof.

6. The quinazoline compound of claim 5, wherein
$NR_1R_2$ is substituted or unsubstituted piperazino or morpholino group; and $R_3$ and $R_4$ are each independently a methyl or ethyl group or $R_3$ and $R_4$ optionally are combined to form a morpholino group,
and pharmaceutically acceptable hydrates and salts thereof.

7. The quinazoline compound of claim 6, wherein
$NR_1R_2$ is N-methylpiperazine;
L is —$CH_2CH_2$—;
$R_3$ and $R_4$ are each a methyl group; and
$R_5$, $R_6$, $R_7$, and $R_8$ are each a hydrogen atom,
and pharmaceutically acceptable hydrates and salts thereof.

8. The quinazoline compound of claim 6, wherein
$NR_1R_2$ is N-methylpiperazine;
L is —$CH_2CH_2$—;
$R_3$ and $R_4$ are combined as a morpholino group; and
$R_5$, $R_6$, $R_7$, and $R_8$ are each a hydrogen atom,
and pharmaceutically acceptable hydrates and salts thereof.

9. The quinazoline compound having a structural formula

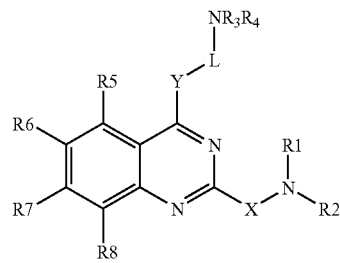

Formula XVIII wherein
X is absent;
$NR_1R_2$ is N-phenylpiperazine;
Y is NH;
L is —$CH_2CH_2$;
$R_3$ and $R_4$ are each a methyl group;
$R_6$ and $R_7$ are each a methoxy group; and
$R_5$ and $R_8$ are each a hydrogen atom,
and pharmaceutically acceptable hydrates and salts thereof.

* * * * *

SEQUENCE LISTING

<160> NUMBER OF SEQ ID NOS: 4

<210> SEQ ID NO 1
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 1

```
tcgtcgtttt gtcgttttgt cgtt                                          24

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2
gggggacgat cgtcggggggg                                              20

<210> SEQ ID NO 3
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 3
tcgtcgtttt cggcgcgcgc cg                                            22

<210> SEQ ID NO 4
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (2)..(2)
<223> OTHER INFORMATION: m5c
<220> FEATURE:
<221> NAME/KEY: modified_base
<222> LOCATION: (5)..(5)
<223> OTHER INFORMATION: m5c
<220> FEATURE:
<221> NAME/KEY: modified_base
<222> LOCATION: (13)..(13)
<223> OTHER INFORMATION: m5c
<220> FEATURE:
<221> NAME/KEY: modified_base
<222> LOCATION: (21)..(21)
<223> OTHER INFORMATION: m5c

<400> SEQUENCE: 4
tcgtcgtttt gtcgttttgt cgtt                                          24
```